US012637713B2

(12) United States Patent
Barad et al.

(10) Patent No.: US 12,637,713 B2
(45) Date of Patent: *May 26, 2026

(54) METHODS AND SYSTEMS FOR PHASING SEQUENCING STRANDS AND LONG-RANGE SEQUENCING

(71) Applicant: Ultima Genomics, Inc., Newark, CA (US)

(72) Inventors: Omer Barad, Mazkeret Batya (IL);
Mark Pratt, Bozeman, MT (US);
Eliane Trepagnier, Oakland, CA (US);
Yoav Etzioni, Tel Aviv (IL); Florian Oberstrass, Redwood City, CA (US);
Gilad Almogy, Palo Alto, CA (US);
Dumitru Brinza, Montara, CA (US)

(73) Assignee: Ultima Genomics, Inc., Fremont, CA (US)

( * ) Notice: Subject to any disclaimer, the term of this patent is extended or adjusted under 35 U.S.C. 154(b) by 475 days.

This patent is subject to a terminal disclaimer.

(21) Appl. No.: 18/035,073

(22) PCT Filed: Nov. 3, 2021

(86) PCT No.: PCT/US2021/072218
§ 371 (c)(1),
(2) Date: May 2, 2023

(87) PCT Pub. No.: WO2022/099270
PCT Pub. Date: May 12, 2022

(65) Prior Publication Data
US 2023/0407385 A1 Dec. 21, 2023

Related U.S. Application Data

(60) Provisional application No. 63/109,822, filed on Nov. 4, 2020.

(51) Int. Cl.
*C12Q 1/68* (2018.01)
*C12Q 1/6874* (2018.01)

(52) U.S. Cl.
CPC ................................ *C12Q 1/6874* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 5,714,320 A | 2/1998 | Kool | |
| 8,364,417 B2 | 1/2013 | Chen | |
| 8,772,473 B2 | 7/2014 | Huang | |
| 9,428,807 B2 | 8/2016 | Hubbell | |
| 9,587,274 B2 | 3/2017 | Chen | |
| 9,817,944 B2 | 11/2017 | Kural | |
| 10,192,024 B2 | 1/2019 | Chen | |
| 10,344,328 B2 | 7/2019 | Barbee | |
| 11,220,709 B2 | 1/2022 | Oberstrass et al. | |
| 11,220,710 B2 | 1/2022 | Oberstrass et al. | |
| 11,459,609 B2 | 10/2022 | Pratt et al. | |
| 11,462,300 B2 | 10/2022 | Bartov et al. | |
| 11,578,363 B2 | 2/2023 | Oberstrass et al. | |
| 11,763,915 B2 | 9/2023 | Etzioni et al. | |
| 12,209,278 B2 * | 1/2025 | Pratt ..................... | G16B 30/00 |
| 2009/0053724 A1 | 2/2009 | Roth | |
| 2010/0093986 A1 | 4/2010 | Zwick et al. | |
| 2010/0173303 A1 | 7/2010 | Ronaghi et al. | |
| 2011/0270533 A1 | 11/2011 | Zhang | |
| 2012/0252682 A1 | 10/2012 | Zhou et al. | |
| 2013/0090860 A1 | 4/2013 | Sikora | |
| 2013/0281306 A1 | 10/2013 | Rigatti et al. | |

(Continued)

FOREIGN PATENT DOCUMENTS

| | | |
|---|---|---|
| KR | 2018-0055905 A | 5/2018 |
| WO | 98/44152 A1 | 10/1998 |

(Continued)

OTHER PUBLICATIONS

Ali, M.M. et al. (2014). "Rolling Circle Amplification: A Versatile Tool For Chemical Biology, Materials Science and Medicine," Chem. Soc. R?ev. 43:3324, 19 pages.
Chaisson, M.J. et al. (2009). "De Novo Fragment Assembly With Short Mate Paired Reads: Does The Read Length Matter?," Genome Research 19:336-346.
Dean et al. (2001). "Rapid Amplification Of Plasmid And Phage DNA Using Phi29 DNA Polymerase And Multiply-Primed Rolling Circle Amplification," Genome Research 11:1095-1099.
Depristo, M.A. et al. (May 2011, e-pub. Nov. 1, 2011). "A Framework For Variation Discovery And Genotyping Using Next-Generation DNA Sequencing Data," Nature Genetics 43(5):491-498, 20 pages.
Hwang, S. et al. (Dec. 7, 2015). "Systematic Comparison Of Variant Calling Pipelines Using Gold Standard Personal Exome Variants," Sci Rep. 5(17875):1-8.

(Continued)

*Primary Examiner* — Kenneth R Horlick
(74) *Attorney, Agent, or Firm* — MORRISON & FOERSTER LLP

(57) ABSTRACT

Described herein are methods synchronizing sequencing primers within a sequencing cluster and methods of generating long-range sequencing reads. The methods can include hybridizing primers to polynucleotide copies within a sequencing cluster; extending the primers through a first region of the polynucleotide copies using labeled nucleotides according to a sequencing flow order; extending the primers through a second region of the polynucleotide copies using one or more re-phasing flow steps that each include at least two different types of nucleotide bases; and extending the primers through a third region of the polynucleotide copies using labeled nucleotides according to the sequencing cycle. The rephasing flow steps may be initiated after a predetermined number of sequencing flow steps, after a measured sequencing signal strength falls below a predetermined sequencing signal strength threshold, or a measured sequencing signal-to-noise ratio falls below a sequencing signal-to-noise ratio threshold.

20 Claims, 26 Drawing Sheets

Specification includes a Sequence Listing.

(56) References Cited

U.S. PATENT DOCUMENTS

| | | |
|---|---|---|
| 2014/0052381 A1 | 2/2014 | Utiramerur |
| 2014/0315724 A1 | 10/2014 | Zhou |
| 2015/0066824 A1 | 3/2015 | Harris |
| 2015/0203910 A1 | 7/2015 | Smith et al. |
| 2016/0110499 A1 | 4/2016 | Donnet |
| 2016/0326579 A1 | 11/2016 | Olejnik |
| 2017/0044601 A1 | 2/2017 | Crnogorac |
| 2017/0335387 A1 | 11/2017 | Brinza |
| 2018/0330051 A1 | 11/2018 | Hubbell |
| 2018/0363047 A1 | 12/2018 | Smith |
| 2019/0360034 A1 | 11/2019 | Zhou et al. |
| 2020/0199666 A1 | 6/2020 | Gatti-Lafranconi et al. |
| 2020/0372971 A1 | 11/2020 | Etzioni |
| 2020/0377937 A1 | 12/2020 | Pratt |
| 2020/0392584 A1 | 12/2020 | Almogy |
| 2021/0010075 A1 | 1/2021 | Oberstrass |
| 2021/0054442 A1 | 2/2021 | Pratt et al. |
| 2021/0147930 A1 | 5/2021 | Oberstrass et al. |
| 2021/0147931 A1 | 5/2021 | Oberstrass et al. |
| 2021/0366576 A1 | 11/2021 | Bartov et al. |
| 2022/0170089 A1 | 6/2022 | Pratt et al. |
| 2023/0060685 A1 | 3/2023 | Pratt et al. |
| 2023/0197197 A1 | 6/2023 | Bartov et al. |
| 2023/0313289 A1 | 10/2023 | Oberstrass et al. |
| 2023/0343416 A1 | 10/2023 | Etzioni et al. |
| 2024/0018599 A1 | 1/2024 | Barad et al. |
| 2024/0043918 A1 | 2/2024 | Barad et al. |
| 2024/0120025 A1 | 4/2024 | Etzioni et al. |
| 2024/0287483 A1 | 8/2024 | Mazur et al. |
| 2024/0309445 A1 | 9/2024 | Oberstrass et al. |
| 2025/0197928 A1 | 6/2025 | Pratt et al. |

FOREIGN PATENT DOCUMENTS

| | | |
|---|---|---|
| WO | 199844151 A1 | 10/1998 |
| WO | 2012134602 A2 | 10/2012 |
| WO | 2012166742 A2 | 12/2012 |
| WO | 2012166742 A3 | 4/2013 |
| WO | 2012134602 A3 | 12/2013 |
| WO | 2017/062863 A1 | 4/2017 |
| WO | 2019084158 A1 | 5/2019 |
| WO | 2019099886 A1 | 5/2019 |
| WO | 2019191003 A1 | 10/2019 |
| WO | 2020172197 A1 | 8/2020 |
| WO | 2020185790 A1 | 9/2020 |
| WO | 2020186243 A1 | 9/2020 |
| WO | 2020227137 A1 | 11/2020 |
| WO | 2020227143 A1 | 11/2020 |
| WO | 2020236630 A1 | 11/2020 |
| WO | 2020240025 A1 | 12/2020 |
| WO | 2021007495 A1 | 1/2021 |
| WO | 2022051296 A1 | 3/2022 |
| WO | 2022056296 A1 | 3/2022 |
| WO | 2022099271 A1 | 5/2022 |
| WO | 2022109574 A1 | 5/2022 |
| WO | 2022204685 A1 | 9/2022 |
| WO | 2023004421 A1 | 1/2023 |
| WO | 2023288319 A1 | 1/2023 |
| WO | 2023010069 A1 | 2/2023 |
| WO | 2023010131 A1 | 2/2023 |
| WO | 2023060091 A1 | 4/2023 |
| WO | 2023081653 A1 | 5/2023 |
| WO | 2023081883 A2 | 5/2023 |
| WO | 2023081883 A3 | 6/2023 |
| WO | 2023141430 A1 | 7/2023 |
| WO | 2023164505 A2 | 8/2023 |
| WO | 2023164505 A3 | 10/2023 |
| WO | 2024/102889 A1 | 5/2024 |

OTHER PUBLICATIONS

International Preliminary Report on Patentability, issued May 8, 2023, for PCT Application No. PCT/US2021/072218, filed Nov. 2021, 9 pages.

International Search Report and Written Opinion, mailed Mar. 2, 2022, for PCT Application No. PCT/US2021/072218, filed Nov. 3, 2021, 13 pages.

Mielczarek, M. et al. (2016). "Review Of Alignment And SNP Calling Algorithms For Next-Generation Sequencing Data," J. Appl. Genetics 57:71-79.

Miller, J.R. et al. (2010, e-pub. Mar. 6, 2010). "Assembly Algorithms For Next-Generation Sequencing Data," Genomics 95:315-327.

Mitra, R.B. et al. (2003). "Fluorescent in Situ Sequencing on Polymerase Colonies," Analytical Biochemistry 320:55-65.

Nielsen, R. et al. (Jun. 2011). "Genotype And SNP Calling From Next-Generation Sequencing Data," Nature Reviews Genetics 12(6):443-451, 20 pages.

Partial Supplementary European Search Report, dated Jul. 7, 2023, for European Patent Application No. 20801590.9, 19 pages.

Peng, Q. et al. (2019, e-pub. Mar. 18, 2019). "Targeted Single Primer Enrichment Sequencing with Single End Duplex-UMI," Scientific Reports 9(4810):1-10.

Poplin, R. et al. (Jul. 24, 2018, e-pub. Nov. 14, 2017). "Scaling Accurate Genetic Variant Discovery To Tens Of Thousands Of Samples," BioRxiv, located at a https://www.biorxiv.org/content/biorxiv/early/2017/11/14/201178.1.full.pdf last visited on Aug. 7, 2020, 22 pages.

Somervuo, P. et al. (2018). "BARCOSEL: A Tool for Selecting an Optimal Barcode Set for High-Throughput Sequencing," BMC Bioinformatics 19:257, 6 pages.

U.S. Appl. No. 18/035,075, filed May 2, 2023, by Omer, et al. (A copy of the U.S. Patent Application is not submitted herewith pursuant to the waiver of 37 C.F.R. § 1.98(a)(2)(iii) issued by the Office on Sep. 21, 2004).

U.S. Appl. No. 18/035,081, filed May 2, 2023, by Omer, et al. (A copy of the U.S. Patent Application is not submitted herewith pursuant to the waiver of 37 C.F.R. § 1.98(a)(2)(iii) issued by the Office on Sep. 21, 2004).

U.S. Appl. No. 18/281,930, filed Sep. 13, 2023, by Oberstrass et al. (A copy of the U.S. Patent Application is not submitted herewith pursuant to the waiver of 37 C.F.R. § 1.98(a)(2)(iii) issued by the Office on Sep. 21, 2004).

U.S. Appl. No. 18/362,754, filed Jul. 31, 2023, by Yoav, et al. (A copy of the U.S. Patent Application is not submitted herewith pursuant to the waiver of 37 C.F.R. § 1.98(a)(2)(iii) issued by the Office on Sep. 21, 2004).

Van Dijk, E.L. et al. (2018). "The Third Revolution in Sequencing Technology," Trends in Genetics 34(9):666-681.

Zerbino, D.R. et al. (2008, e-pub. Mar. 18, 2008). "Velvet: Algorithms For De Novo Short Read Assembly Using De Bruijn Graphs," Genome Research 18:821-829, 11 pages.

Zook, J. M. et al. (Apr. 1, 2019). "An Open Resource For Accurately Benchmarking Small Variant And Reference Calls," Nature Biotechnology 37:561-566, 14 pages.

* cited by examiner

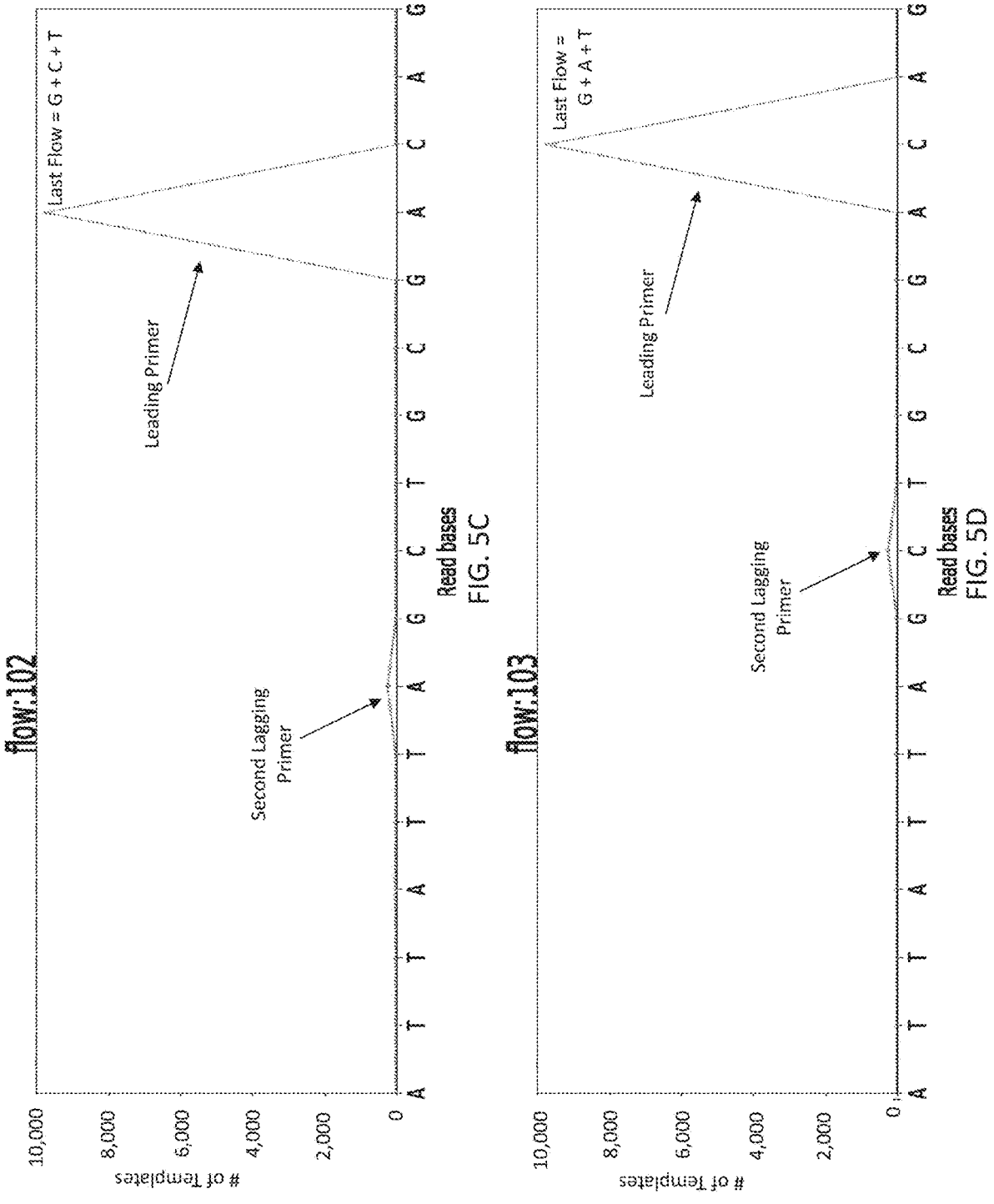

A NUCLEOTIDE FLOWS

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1
tccgcagcga tcactccatt actttg                                        26

<210> SEQ ID NO 2
<211> LENGTH: 36
<212> TYPE: DNA
<213> ORGANISM: Artificial Sequence
<220> FEATURE:
<223> OTHER INFORMATION: Synthetic Construct

<400> SEQUENCE: 2
agcgggtaga gggacgtgtg ccttgattca acctcg                             36
```

-continued

```
<210> SEQ ID NO 3
<211> LENGTH: 17
<212> TYPE: DNA
<213> ORGANISM: Artificial Sequence
<220> FEATURE:
<223> OTHER INFORMATION: Synthetic Construct

<400> SEQUENCE: 3
attattagct gcgacag                                                        17
```

1

METHODS AND SYSTEMS FOR PHASING SEQUENCING STRANDS AND LONG-RANGE SEQUENCING

CROSS-REFERENCE TO RELATED APPLICATION

This application is a national stage application under 35 U.S.C. § 371 of International Application No. PCT/US2021/072218, filed internationally on Nov. 3, 2021, which claims priority to and the benefit of U.S. Provisional Application No. 63/109,822, filed Nov. 4, 2020, each of which is incorporated herein by reference for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165272000600SEQLIST.txt, date recorded: May 2, 2023, size: 868 bytes).

FIELD OF THE INVENTION

Described herein are methods of sequencing a polynucle-otide, including long-range sequencing, and methods of phasing sequencing strands.

BACKGROUND

Next-generation sequencing (NGS) technology often relies on the generation of short sequencing reads. Paired-end technology has allowed for coupling of short sequencing reads with a gap in sequencing information between the paired ends. Using traditional paired-end sequencing, no (or very little) information is derived for the region between the 3' and 5' ends of a polynucleotide. Although the paired end sequencing data can be used for certain analytical purposes, it cannot be used to detect certain variants in the unse-quenced region of the polynucleotide. This information gap can omit important genetic information and risks incorrect alignment of the paired ends.

Long-range sequencing is often considered the next fron-tier in sequencing technology, and can allow for higher confidence large structural variant calling, haplotype phas-ing, and transcriptome analysis. See van Dijk et al., *The Third Revolution in Sequencing Technology*, Trends in Genetics, vol. 34, no. 9, pp. 666-681 (2018). However, read length using current technology remains limited, in part due to signal quality degradation as the sequencing reaction progresses. Additionally, current long-read sequencing tech-nology is expensive, slow, and prone to substantial sequenc-ing errors.

BRIEF SUMMARY OF THE INVENTION

Described herein are sequencing methods, including long-read sequencing methods, and methods of sequencing that can be used to synchronize sequencing primers within a sequencing cluster. The methods include the use of a re-phasing cycle between a first sequencing region and a second sequencing region. The re-phasing cycle synchro-nizes at least a portion of the sequencing primers, which can otherwise form leading and lagging strands when extended within the sequencing regions. By synchronizing the primers, a higher quality sequencing signal can be generated that provides more reliable sequencing data.

A method of synchronizing sequencing in a colony may include: (a) providing a sequencing colony comprising a plurality of copies of nucleic acid molecules having sequence identity, wherein each nucleic acid molecule of the plurality of copies comprises a first region, a second region, and a third region; (b) hybridizing a plurality of primers to the plurality of copies; (c) extending the plurality of primers through the first region by, in each flow step of a plurality of first flow cycles having a first predetermined number of flow steps, providing a first plurality of nucleotides of a single base type, wherein at least a portion of the first plurality of nucleotides is labeled; (d) extending, after the first prede-termined number of flow steps, the plurality of primers through the second region by, in each flow step of a plurality of second flow cycles, providing a second plurality of nucleotides comprising at least two base types; and (e) extending the plurality of primers through the third region by, in each flow step of a plurality of third flow cycles, providing a third plurality of nucleotides of a single base type, wherein at least a portion of the third plurality of nucleotides is labeled. The first predetermined number of flow steps may be between about 40 and about 500. The first predetermined number of flow steps may be associated with a predetermined sequencing signal threshold. In some implementations, the first predetermined number of flow steps is associated with an expected proportion of unsyn-chronized primers. For example, the expected proportion of unsynchronized primers may be between about 0.1 and about 0.5. In some implementations, the first predetermined number of sequencing flow steps is associated with an expected length of the first region.

In some implementations of the above methods, the plurality of third flow cycles has a second predetermined number of flow steps, the method further comprising: (f) extending, after the second predetermined number of flow steps, the plurality of primers through a fourth region of the plurality of copies by, in each flow step of a plurality of fourth flow cycles, providing a fourth plurality of nucleo-tides comprising at least two base types; and (g) extending the plurality of primers through a fifth region of the plurality of copies by, in each flow step of a plurality of fifth flow cycles, providing a fifth plurality of nucleotides of a single base type, wherein at least a portion of the fifth plurality of nucleotides is labeled. In some implementations, the first predetermined number of flow steps and the second prede-termined number of flow steps are the same. In some implementations, the second predetermined number of flow steps is less than the first predetermined number of flow steps.

In some implementations of the above method, the method further includes sequencing the fifth region by detecting the presence or absence of an incorporated labeled nucleotide while extending the primers through the fifth region.

In some implementations, a method of synchronizing sequencing, may include: (a) providing a sequencing colony comprising a plurality of copies of nucleic acid molecules having sequence identity, wherein each nucleic acid mol-ecule of the plurality of copies comprises a first region, a second region, and a third region; (b) hybridizing a plurality of primers to the plurality of copies; (c) extending the plurality of primers through the first region by, in each flow step of a plurality of first flow cycles, (i) providing a first plurality of nucleotides of a single base type, wherein at least a portion of the first plurality of nucleotides are labeled, and (ii) detecting a signal indicative of incorporation, or lack thereof, of a labeled nucleotide of the first plurality of nucleotides in the plurality of primers, until the signal falls below a first predetermined sequencing signal threshold; (d) extending, after the signal falls below the first predetermined sequencing signal threshold, the plurality of primers through the second region by, in each flow step of a plurality of second flow cycles, providing a second plurality of nucleotides comprising at least two base types; and (e) extending the plurality of primers through the third region by, in each flow step of a plurality of third flow cycles, providing a third plurality of nucleotides of a single base type, wherein at least a portion of the third plurality of nucleotides is labeled. The signal may be a sequencing signal intensity or a sequencing signal-to-noise ratio. In some implementations, the method further includes detecting one or more signals or sequencing signal-to-noise ratio as the primers are extended through the first region in (c).

In some implantations of the above method, the plurality of primers is extended through the third region until a second signal detected falls below a second predetermined sequencing signal threshold, the method further comprising: (f) extending, after the second signal falls below the second predetermined sequencing signal threshold, the plurality of primers through a fourth region of the plurality of copies by, in each flow step of a plurality of fourth flow cycles, providing a fourth plurality of nucleotides comprising at least two base types; and (g) extending the plurality of primers through a fifth region of the plurality of copies by, in each flow step of a plurality of fifth flow cycles, providing a fifth plurality of nucleotides of a single base type, wherein at least a portion of the fifth plurality of nucleotides is labeled. In some implementations, the first predetermined sequencing signal threshold and the second predetermined sequencing signal threshold are the same. In some implementations, the method further includes sequencing the fifth region by detecting the presence or absence of an incorporated labeled nucleotide while extending the primers through the fifth region.

In some implementations of the methods described herein, a mixture of three different base types is used in at least one flow step of the plurality of second flow cycles.

In some implementations of the methods described herein, one or more flow steps of the plurality of second flow cycles comprise 2 to 12 re-phasing flow steps.

In some implementations of the methods described herein, one or more flow steps of the plurality of second flow cycles comprise 3 or more re-phasing flow steps.

In some implementations of the methods described herein, one or more flow steps of the plurality of second flow cycles comprise 3 re-phasing flow steps.

In some implementations of the methods described herein, one or more flow steps of the plurality of second flow cycles comprise one or more of the following in any order: (i) a flow step comprising a mixture comprising A, C, and G nucleotides and omitting T nucleotides; (ii) a flow step comprising a mixture comprising T, C, and G nucleotides and omitting A nucleotides; (ii) a flow step comprising a mixture comprising T, A, and G nucleotides and omitting C nucleotides; and (iv) a flow step comprising a mixture comprising T, A, and C nucleotides and omitting G nucleotides.

In some implementations of the methods described herein, the method further comprises sequencing the first region by detecting the presence or absence of an incorporated labeled nucleotide while extending the primers through the first region.

In some implementations of the methods described herein, the method further comprises sequencing the third region by detecting the presence or absence of an incorporated labeled nucleotide while extending the primers through the third region.

In some implementations of the methods described herein, at least a portion of nucleotides provided in the plurality of second flow cycles are unlabeled.

In some implementations of the methods described herein, a first flow order of the plurality of first flow cycles and a third order of the plurality of third flow cycles are the same.

In some implementations of the methods described herein, a first flow order of the plurality of first flow cycles and a third order of the plurality of third flow cycles are different.

In some implementations of the methods described herein, the plurality of primers is extended through the first region by repeating a first flow order a plurality of times in the plurality of first flow cycles. In some implementations, the first flow order is repeated 2 times to about 50 times.

In some implementations of the methods described herein, the plurality of primers is extended through the third region by repeating a third flow order a plurality of times in the plurality of third flow cycles. In some implementations, the third flow order is repeated 2 times to about 50 times.

In some implementations of the methods described herein, the plurality of primers is extended through three or more separate regions of the plurality of copies using a plurality of re-phasing flow steps, and wherein sequencing data is generated for four or more separate regions of the polynucleotide copies.

In some implementations of the methods described herein, a distance between a start of the first region and an end of a final region of the plurality of copies for which sequencing data is generated is at least 300 bases in length.

A method of synchronizing sequencing primers within a sequencing cluster can include: hybridizing primers to poly-nucleotide copies within a sequencing cluster; extending the primers through a first region of the polynucleotide copies using labeled nucleotides according to a first region flow order for a predetermined number of sequencing flow steps or until a measured sequencing signal (e.g., a signal strength or a measured sequencing signal-to-noise ratio) falls below a predetermined sequencing signal threshold; extending, after the predetermined number of sequencing flow steps or the measured sequencing signal falls below the predetermined sequencing signal threshold, the primers through a second region of the polynucleotide copies using one or more re-phasing flow steps, wherein a mixture of at least two different types of nucleotide bases are used in each of the one or more re-phasing flow steps; and extending the primers through a third region of the polynucleotide copies using labeled nucleotides according to a third region flow order. At least a portion (or all) of nucleotides in the one or more re-phasing flow steps can be unlabeled. The sequencing cycle in the first region and the second region may be the same or different.

The method can further include generating sequencing data associated with a sequence of the first region by detecting the presence or absence of an incorporated labeled nucleotide while extending the primers through the first region and/or generating sequencing data associated with a sequence of the third region by detecting the presence or absence of an incorporated labeled nucleotide while extending the primers through the third region.

The process of synchronizing the primers can be repeated multiple times during sequencing after different sequencing regions. For example, the method may further include extending, after extending the primers through the third region for a second predetermined number of sequencing flow steps or a measured sequencing signal in the third region falls below the predetermined sequencing signal threshold, the primers through a fourth region of the poly-nucleotide copies using one or more re-phasing flow steps, wherein a mixture of at least two different types of nucleo-tide bases are used in each of the one or more re-phasing flow steps; and extending the primers through a fifth region of the polynucleotide copies using labeled nucleotides according to a fifth region flow order. The first predeter-mined number of sequencing flow steps and the second predetermined number of sequencing flow steps can be the same or different (for example, the second predetermined number may be less than the first predetermined number). The method may further include generating sequencing data associated with a sequence of the fifth region by detecting the presence or absence of an incorporated labeled nucleo-tide while extending the primers through the fifth region. This process may be continued such that the primers are extended through three or more separate regions of the polynucleotide copies using re-phasing flow steps, and sequencing data is generated for four or more separate regions of the polynucleotide copies. The distance between the start of the first region of the polynucleotide copies and the end of a final region of the polynucleotide copies for which sequencing data is generated can be at least 1000 bases in length.

In an example, the primers can be extended through the second region of the polynucleotide copies using the one or more re-phasing flow steps after the predetermined number of sequencing flow steps. The predetermined number of sequencing flows can be, for example, between about 40 and about 500, although other numbers of flows are possible. The predetermined number of sequencing flow steps can be associated with a predetermined sequencing signal threshold or predetermined sequencing signal-to-noise threshold. The predetermined number of sequencing flow steps can be associated with an expected proportion of unsynchronized primers (for example between about 0.1 and about 0.5). The predetermined number of sequencing flow steps can be associated with an expected length of the first region.

In another example, the primers can be extended through the second region of the polynucleotide copies using the one or more re-phasing flow steps after the measured sequencing signal falls below the predetermined sequencing signal threshold. For example, the measured sequencing signal can be determined in real time (i.e., as the primer is extended through the first region).

A mixture of three different types of nucleotide bases can be used in at least one of the one or more re-phasing flow steps. By way of example, the one or more re-phasing flow steps can include, one or more of and in any order: (i) a flow comprising a mixture comprising A, C, and G nucleotides and omitting T nucleotides; (ii) a flow comprising a mixture comprising T, A, and G nucleotides and omitting C nucleo-tides; (iii) a flow comprising a mixture comprising T, A, and C nucleotides and omitting G nucleotides; and (iv) and a flow comprising a mixture comprising T, C, and G nucleo-tides and omitting A nucleotides. In some implementations, the one or more re-phasing flows comprises 2 to 12 re-phasing flows, or 3 or more (or 3) re-phasing flows.

A method of generating a long-range sequencing read can include: hybridizing primers to polynucleotide copies within a sequencing cluster; and alternatingly generating sequenc-ing data and re-phrasing the primers across a plurality of sequencing regions and a plurality of re-phrasing regions, wherein: generating sequencing data for a sequencing region comprises extending the primers through the sequencing region using labeled nucleotides according to a sequencing flow order, and detecting the presence or absence of an incorporated labeled nucleotide while extending the primers through the sequencing region; and re-phrasing the primers comprises extending the primers through a re-phasing region using one or more re-phasing flows, wherein a mixture of at least two different types of nucleotide bases are used in each of the one or more re-phasing flows; wherein the distance between the start of a first sequencing region and the end of final sequencing region is at least 300 bases in length (for example about 300 bases to about 5,000 bases in length). The plurality of sequencing regions can include, for example, at least four sequencing regions, and the plurality of re-phrasing regions can include at last three re-phrasing regions. The sequencing regions may be, for example, between about 50 and about 500 bases in length. The one or more re-phasing flows may include between 2 and 12 re-phasing flows (such as 3) re-phasing flows. By way of example, the one or more re-phasing flows may include, any one or more of the following flows in any order: (i) a flow comprising a mixture comprising A, C, and G nucleotides and omitting T nucleotides; (ii) a flow comprising a mixture comprising T, A, and G nucleotides and omitting C nucleo-tides; (iii) a flow comprising a mixture comprising T, A, and C nucleotides and omitting G nucleotides; and (iv) a flow comprising a mixture comprising T, C, and G nucleotides and omitting A nucleotides. A mixture of three different types of nucleotide bases may be used in at least one of the one or more re-phasing flows. At least a portion (or all) of nucleotides in the one or more re-phasing flows may be unlabeled.

In a method of generating a long-range sequencing read, the primers may be extended through the sequencing region for a predetermined number of sequencing flows, for example between about 40 and about 200 sequencing flows. The predetermined number of sequencing flows may be associated with a predetermined sequencing signal thresh-old. The predetermined number of sequencing flows may be associated with an expected proportion of unsynchronized primers (for example between about 0.5 and about 0.9). The predetermined number of sequencing flows may be associ-ated with an expected length of the sequencing region.

In any of the methods describe above, the nucleotides used to extend the primers may be non-terminating nucleo-tides.

In any of the methods describe above, the sequencing flows may include a single type of nucleotide base.

In any of the methods describe above, at least a portion (or all) of the nucleotides used in the re-phasing flows are unlabeled.

BRIEF DESCRIPTION OF THE DRAWINGS

FIG. 5A-5E shows the number of primers extended against identical polynucleotide templates in another exemplary simulated sequencing protocol after 100 nucleotide flows (FIG. 5A), and re-phasing flows designed to synchronize primers within a sequencing cluster. The illustrated re-phasing flow cycle is a four-step order that includes nucleotide flow 101 (FIG. 5B), flow 102 (FIG. 5C), flow 103 (FIG. 5D), and flow 104 (FIG. 5E).

over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C, G, and T was used after every 96th flow). The mean and standard deviations are shown in the figure legend. The integral of the distribution for the control and re-phasing protocols is also shown.

Figure 6A:
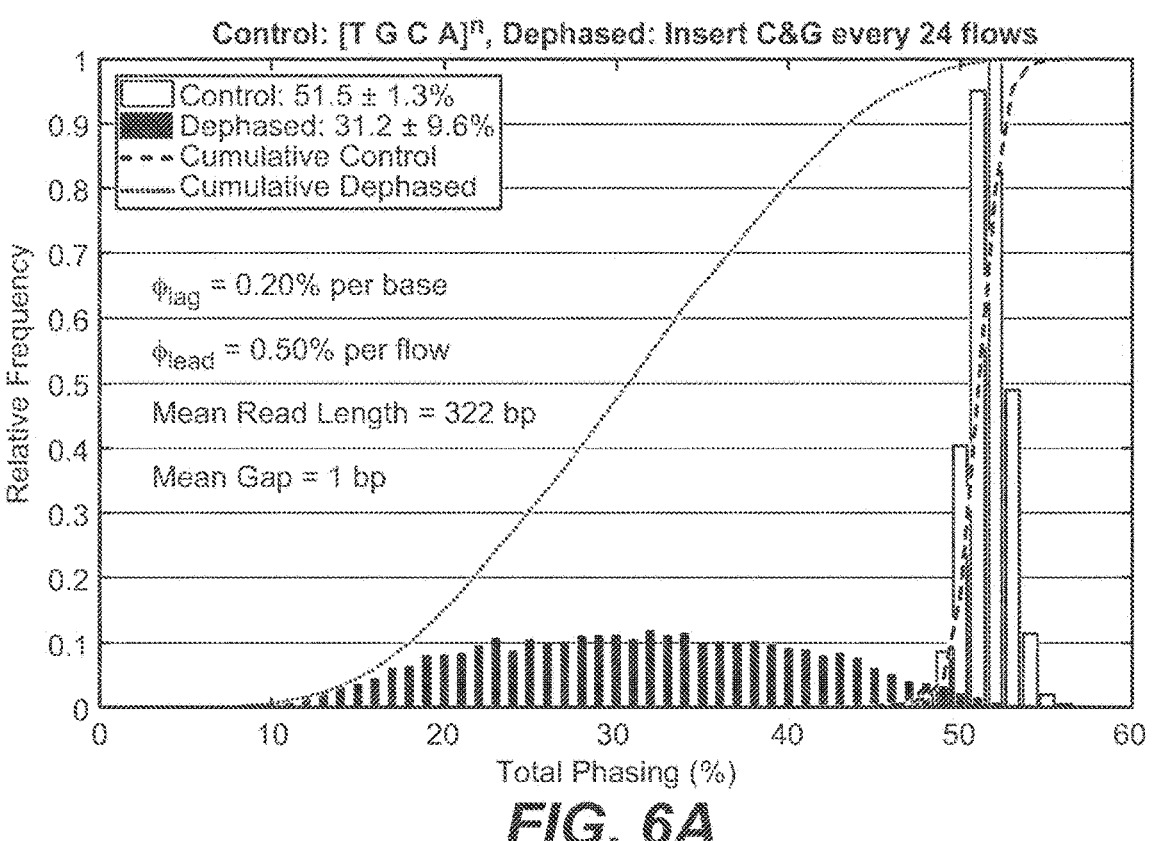
FIG. 6A shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C and G was used after every 24th flow). The mean and standard deviations are shown in the figure legend. The integral of the distribution for the control and re-phasing protocols is also shown.
Figure 6B:
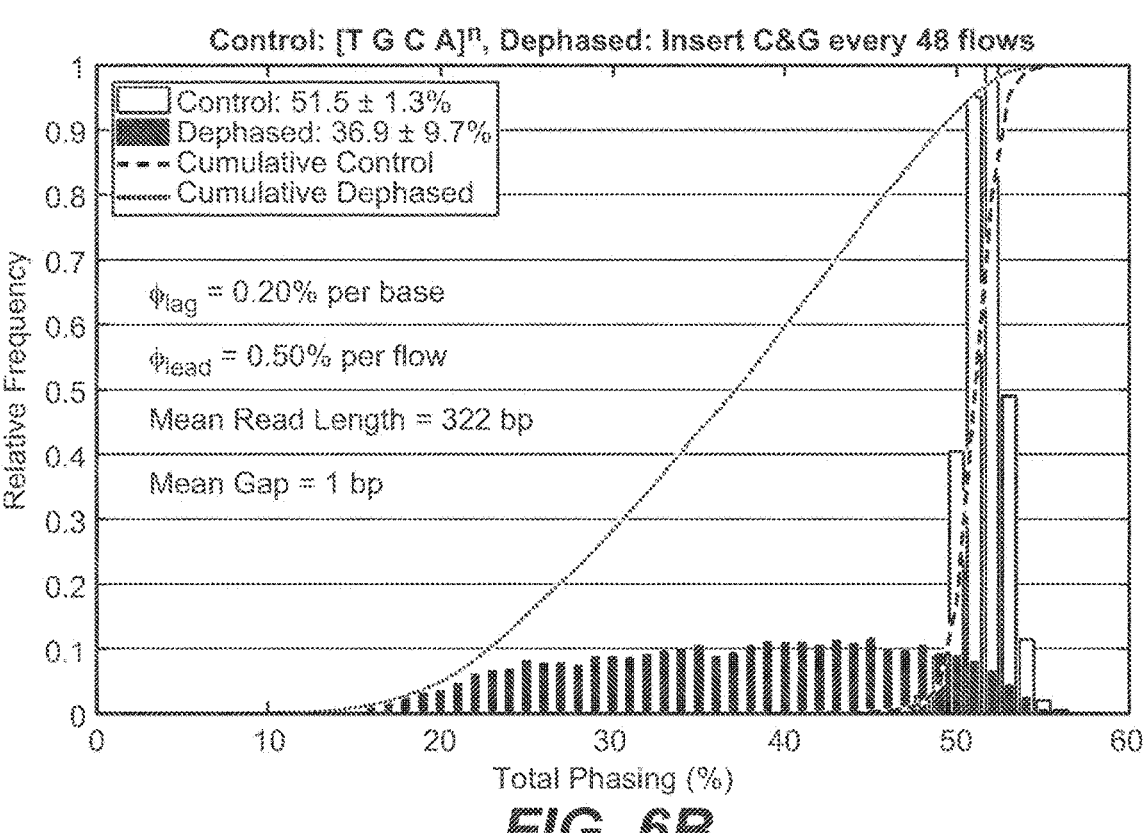
FIG. 6B shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C and G was used after every 48th flow). The mean and standard deviations are shown in the figure legend. The integral of the distribution for the control and re-phasing protocols is also shown.
Figure 6C:
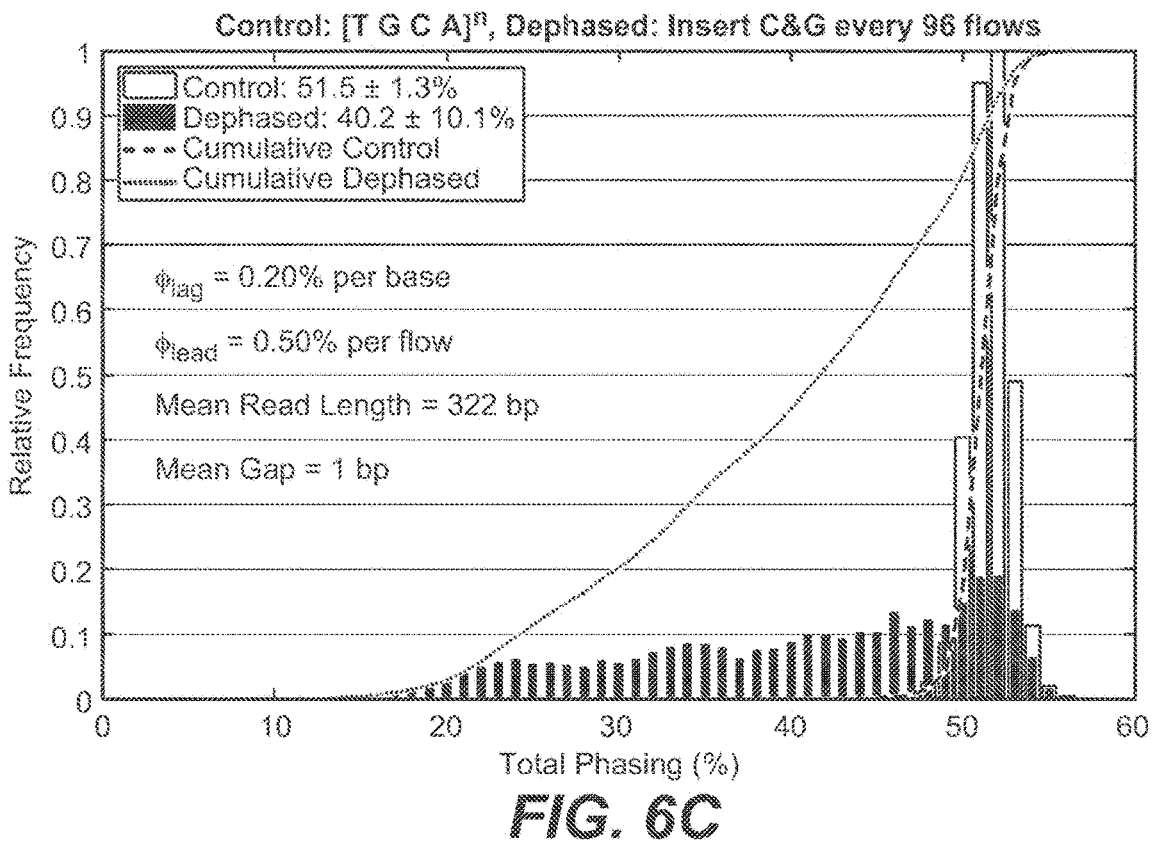
FIG. 6C shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C and G was used after every 96th flow). The mean and standard deviations are shown in the figure legend. The integral of the distribution for the control and re-phasing protocols is also shown
Figure 6D:
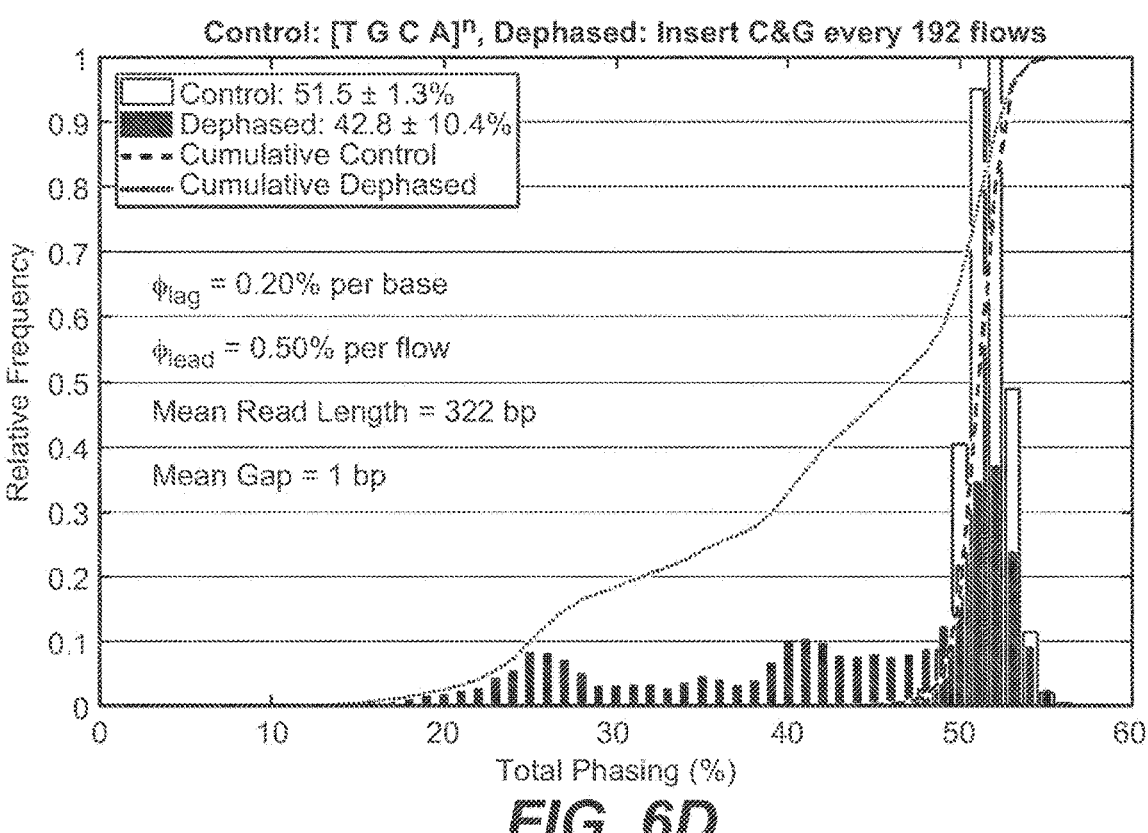
FIG. 6D shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C and G was used after every 192nd flow). The mean and standard deviations are shown in the figure legend. The integral of the distribution for the control and re-phasing protocols is also shown
Figure 6E:
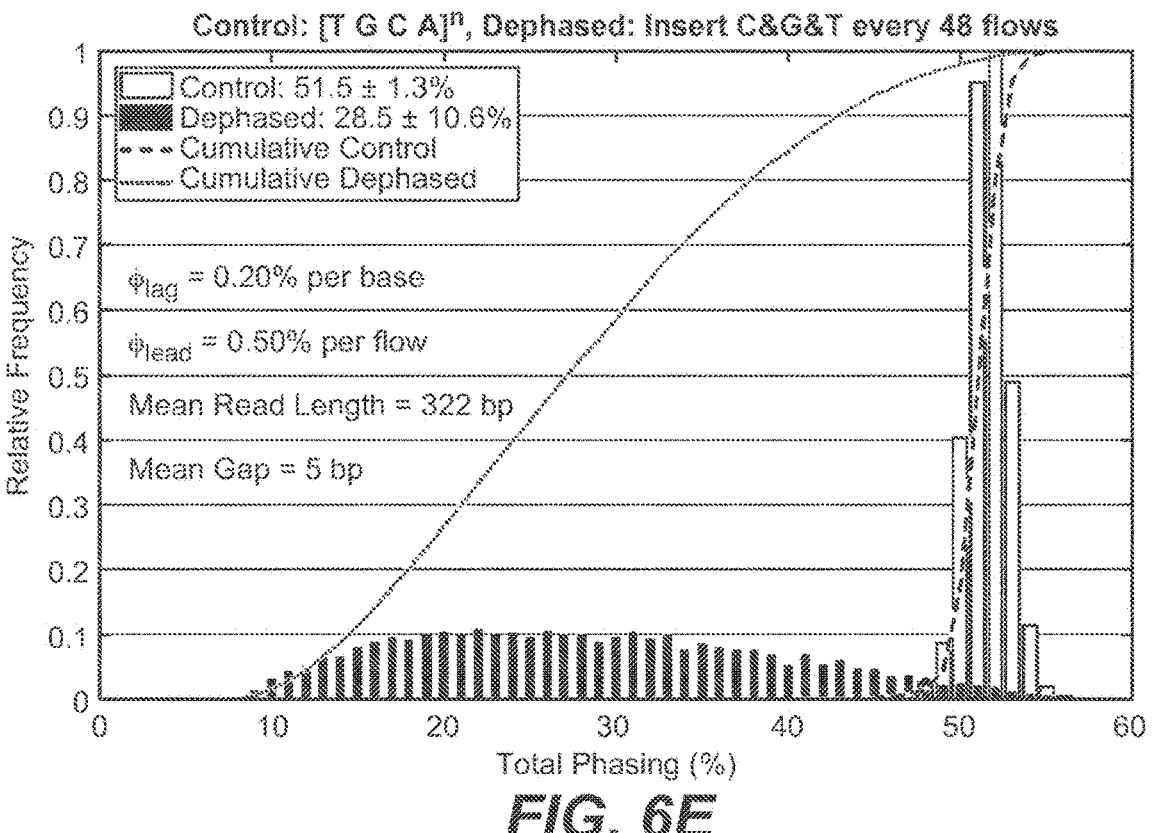
FIG. 6E shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a re-phasing flow containing a mixture of C, G, and T was used after every 48th flow). The mean and standard deviations are shown in the figure legend. The integral of the distribution for the control and re-phasing protocols is also shown.
Figure 6F:
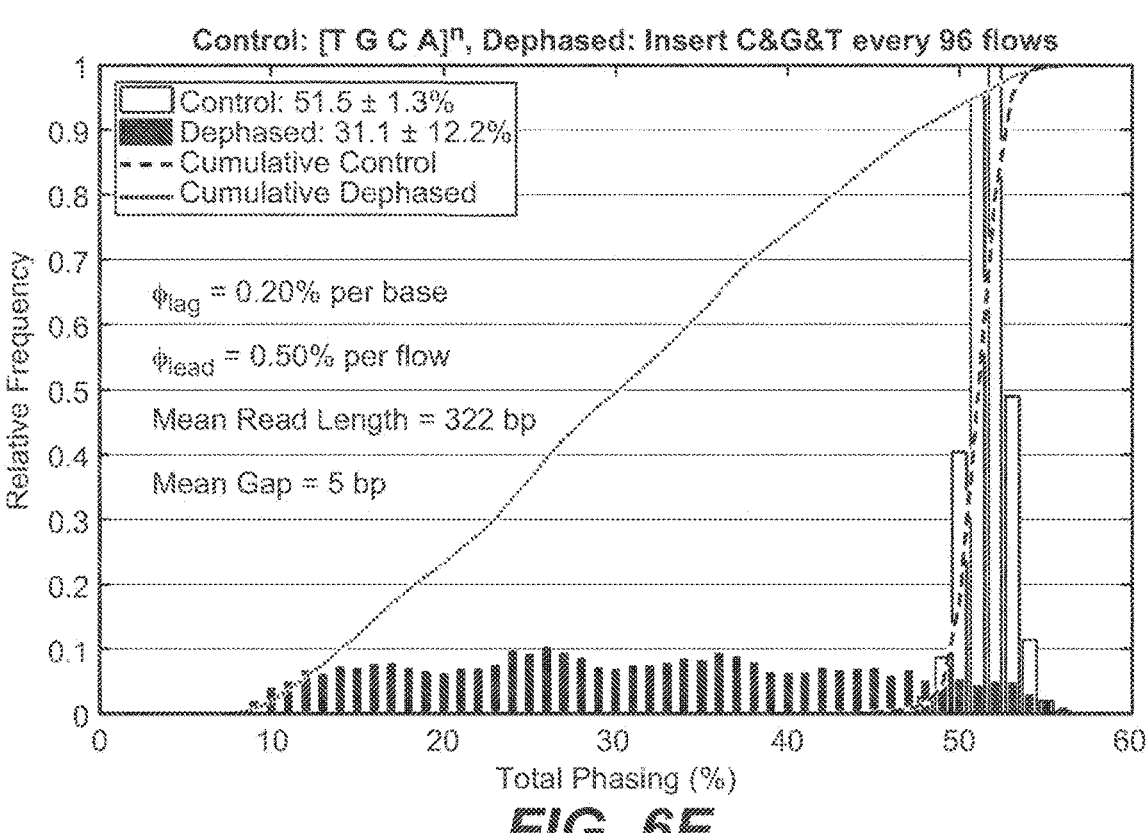
FIG. 6F shows the distribution of the sum of accumulated total phasing error (lag phasing error plus lead phasing error)
Figure 6G:
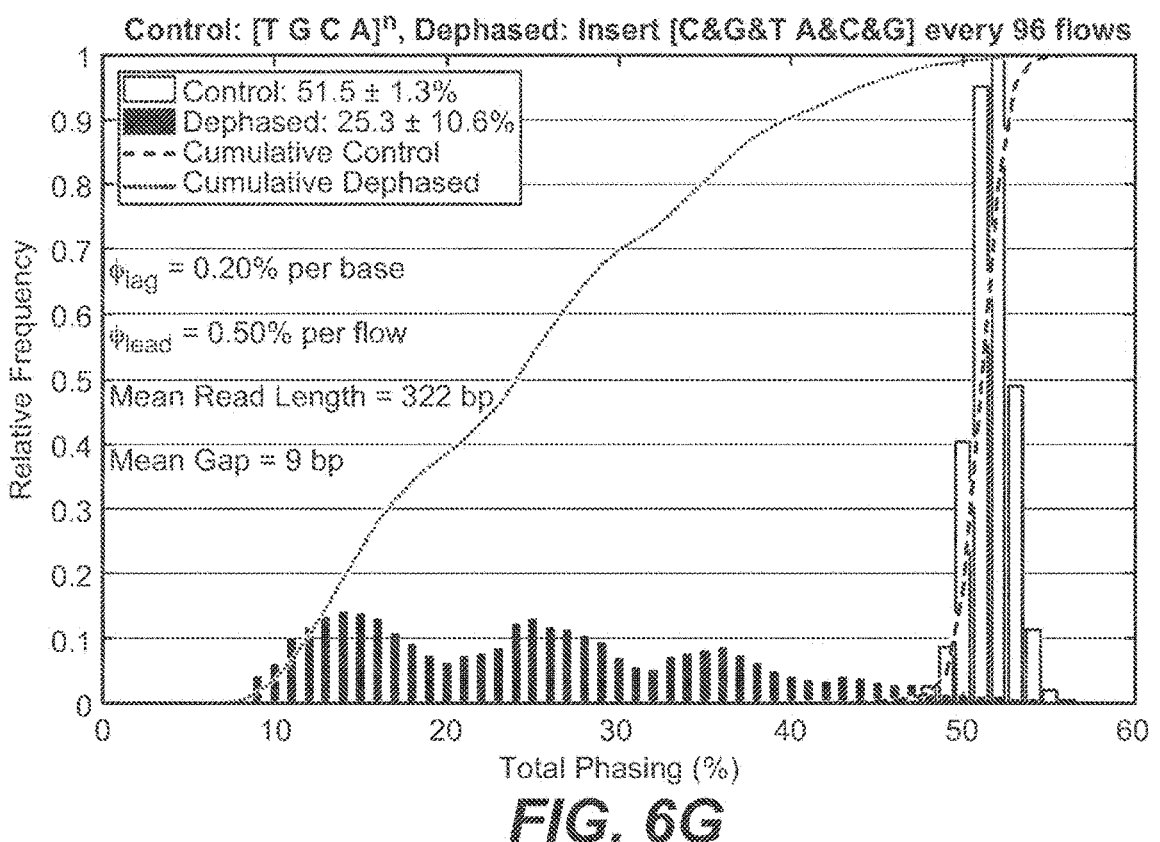

FIG. 6G shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a first re-phasing flow containing a mixture of C, G, and T and a second re-phasing flow containing a mixture of A, C, and G was used after every 96th flow). The mean and standard deviations are shown in the figure legend. The integral of the distribution for the control and re-phasing protocols is also shown.

Figure 6H:
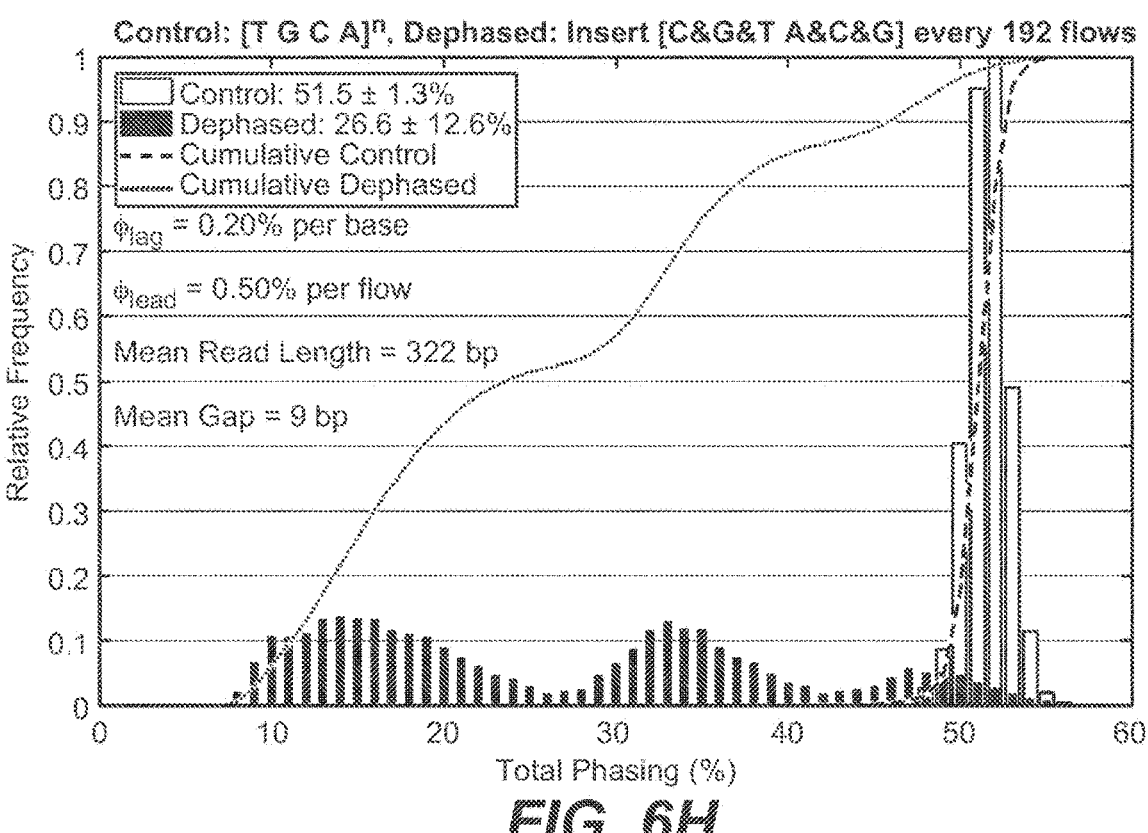

FIG. 6H shows the distribution of the sum of accumulated total phasing error (e.g., lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a first re-phasing flow containing a mixture of C, G, and T and a second re-phasing flow containing a mixture of A, C, and G were used after every 192nd flow). The mean and standard deviations are shown in the figure legend. The integral of the distributions for the control protocols (e.g., "cumulative control") and re-phasing protocol (e.g., "cumulative dephased") are also shown.

Figure 6I:
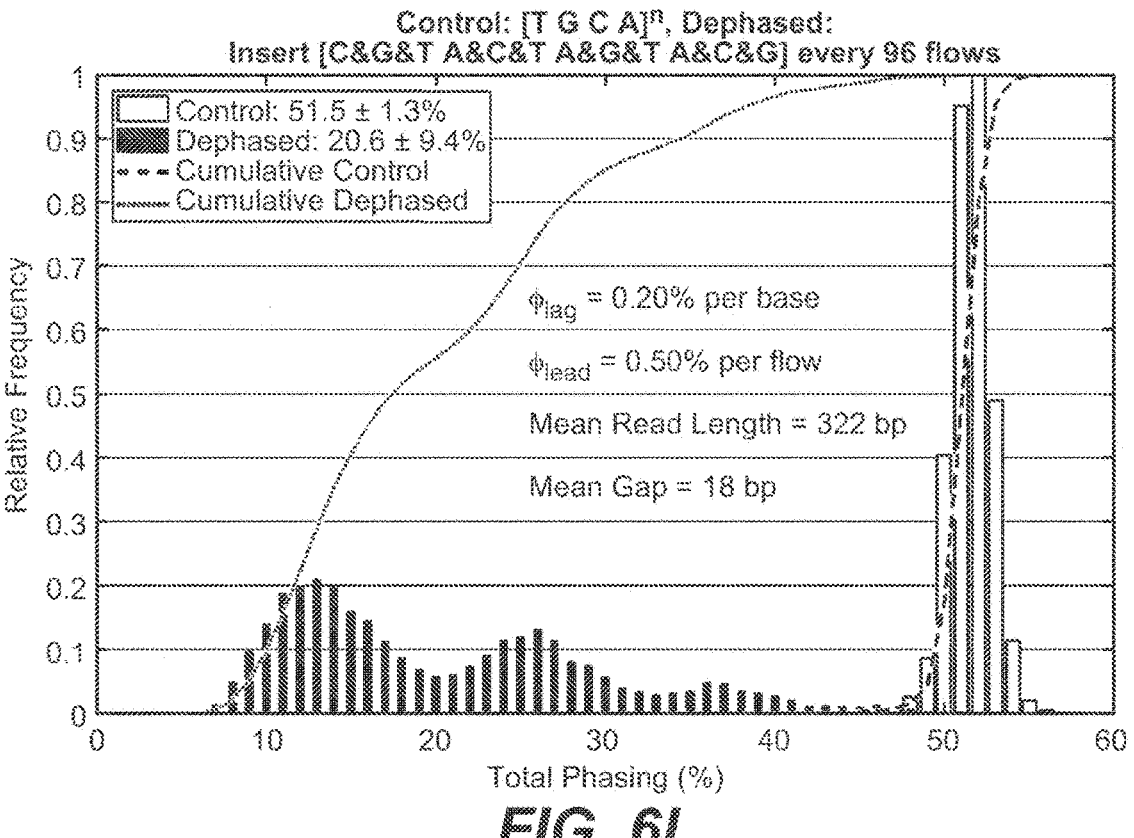

FIG. 6I shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a f first re-phasing flow containing a mixture of C, G, and T, a second re-phasing flow containing a mixture of A, C, and T, a third re-phasing flow containing a mixture of A, G, and T, and a fourth re-phrasing flow containing a mixture of A, C, and G was used after every 96th flow). The mean and standard deviations are shown in the figure legend. The integral of the distribution for the control and re-phasing protocols is also shown.

Figure 6J:
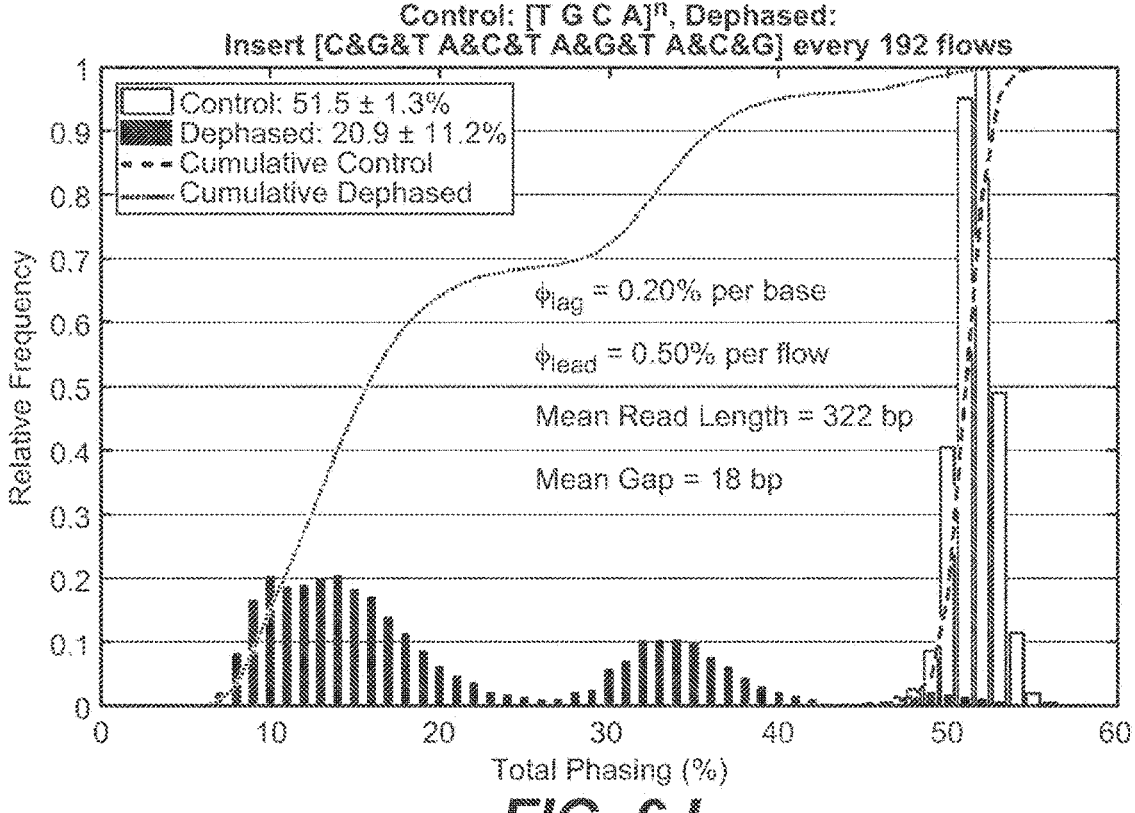

FIG. 6J shows the distribution of the sum of accumulated total phasing error (lag phasing error plus lead phasing error) over 10,000 simulated flowgrams for a control protocol (e.g., 105 rounds of a T-G-C-A flow cycle) or a re-phasing protocol (e.g., 105 rounds of a T-G-C-A flow cycle, wherein a f first re-phasing flow containing a mixture of C, G, and T, a second re-phasing flow containing a mixture of A, C, and T, a third re-phasing flow containing a mixture of A, G, and T, and a fourth re-phrasing flow containing a mixture of A, C, and G was used after every 192nd flow). The mean and standard deviations are shown in the figure legend. The integral of the distribution for the control and re-phasing protocols is also shown.

Figure 7A:
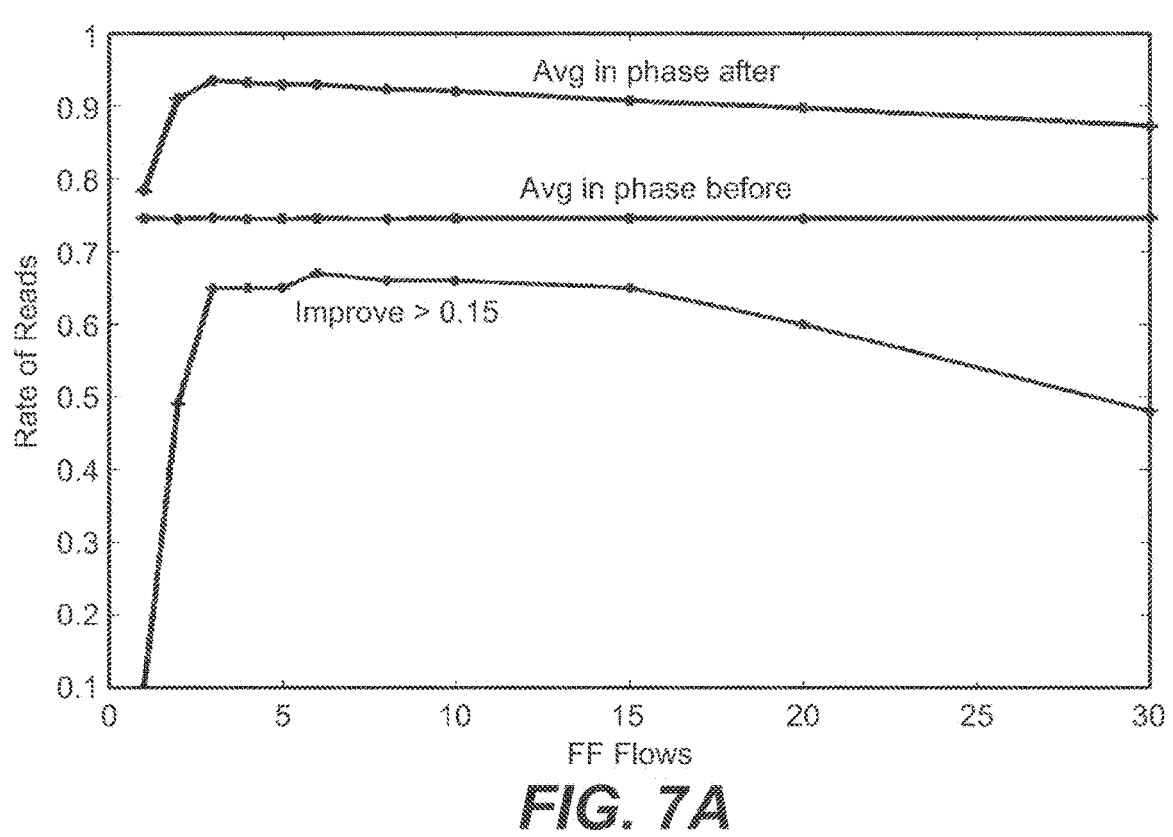

FIG. 7A shows simulated in-phase flow rate (before and after the re-phasing cycle) and secondary re-phasing efficiency of an exemplary polynucleotide when 1, 2, 3, 4, 5, 6, 8, 10, 15, 20, or 30 re-phasing flows were after simulated sequencing.

Figure 7B:
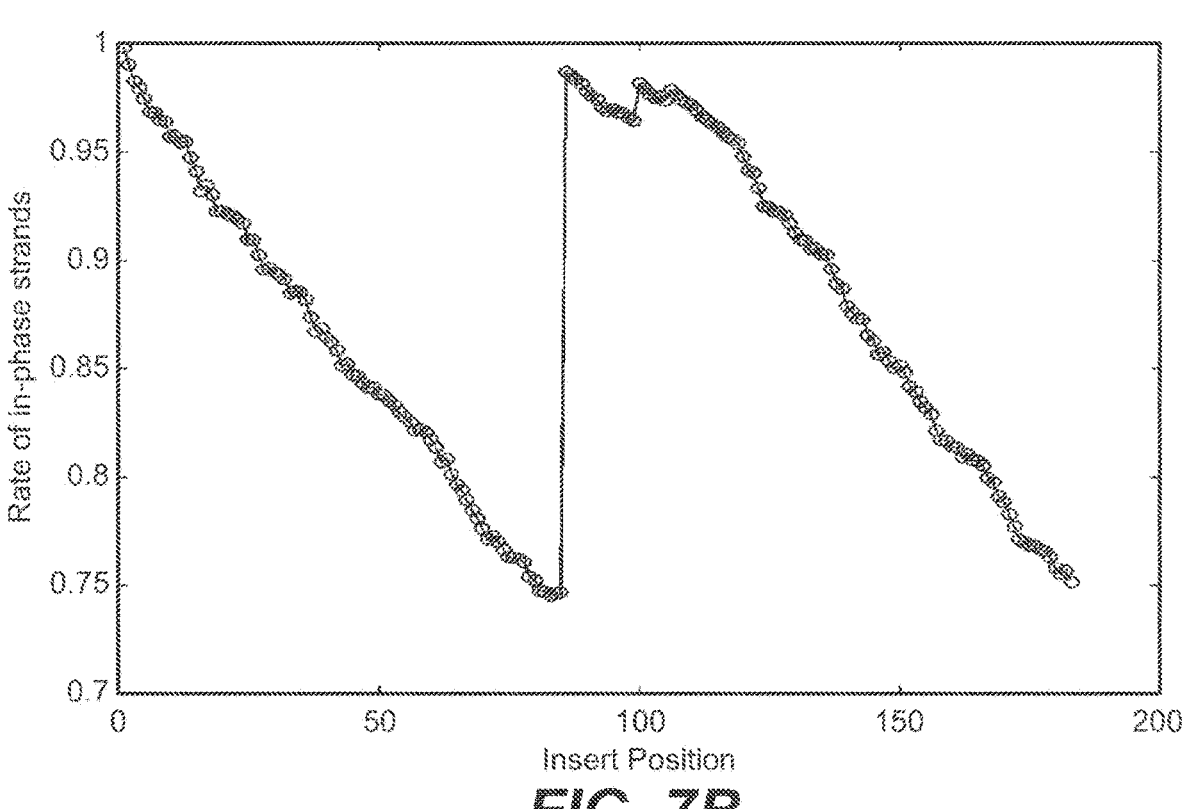

FIG. 7B shows an example simulation of the rate of in-phase sequencing primers as a function of polynucleotide position.

Figures 7C, 7D:
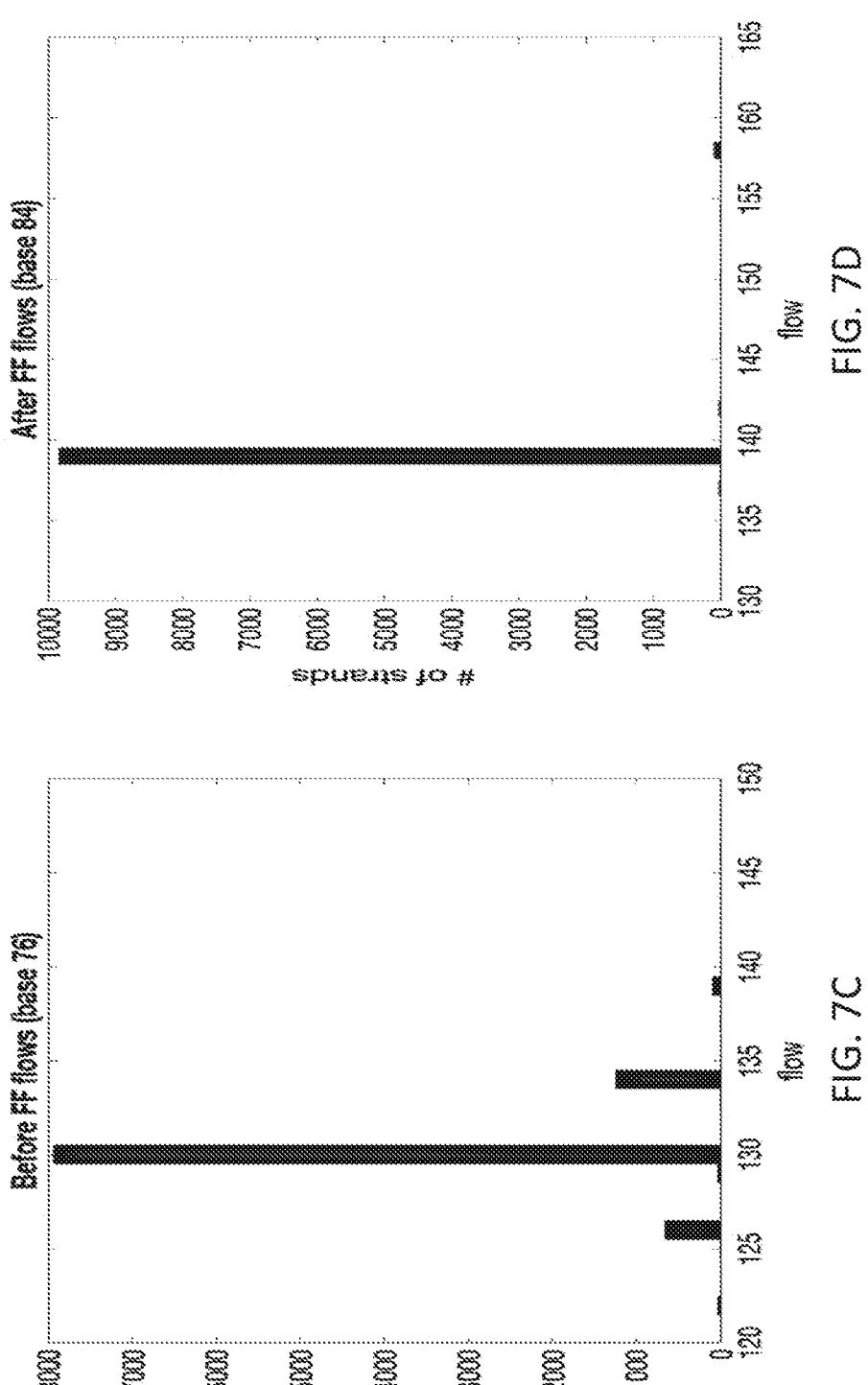

FIG. 7C shows the number of sequencing primers reaching base position 76 (before a simulated re-phasing cycle) as a function of flow number after simulated sequencing, and FIG. 7D shows the number of sequencing primers reaching base 84 (after a simulated re-phasing cycle) a function of flow number.

Figure 8A:
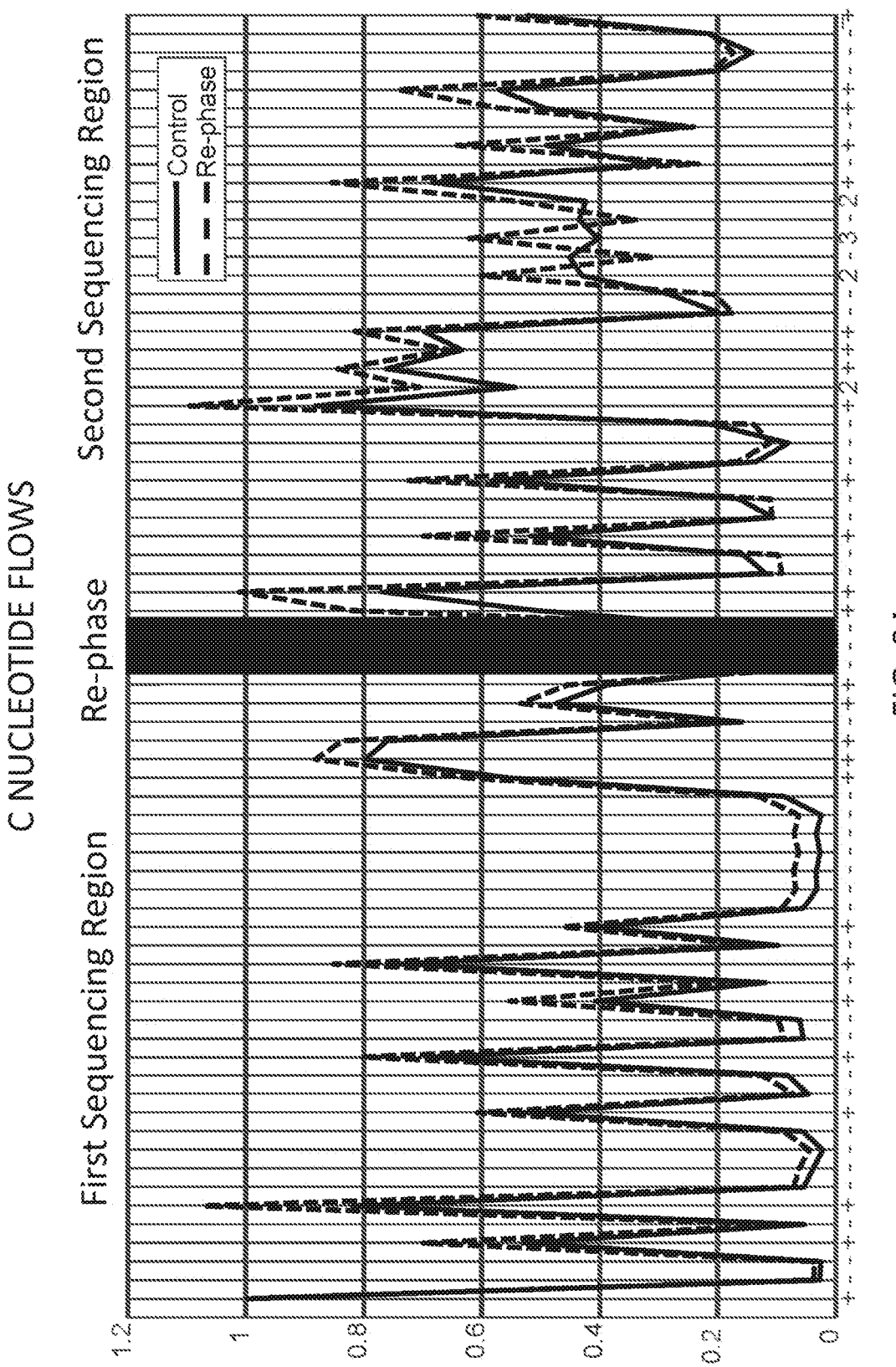
Figure 8B:
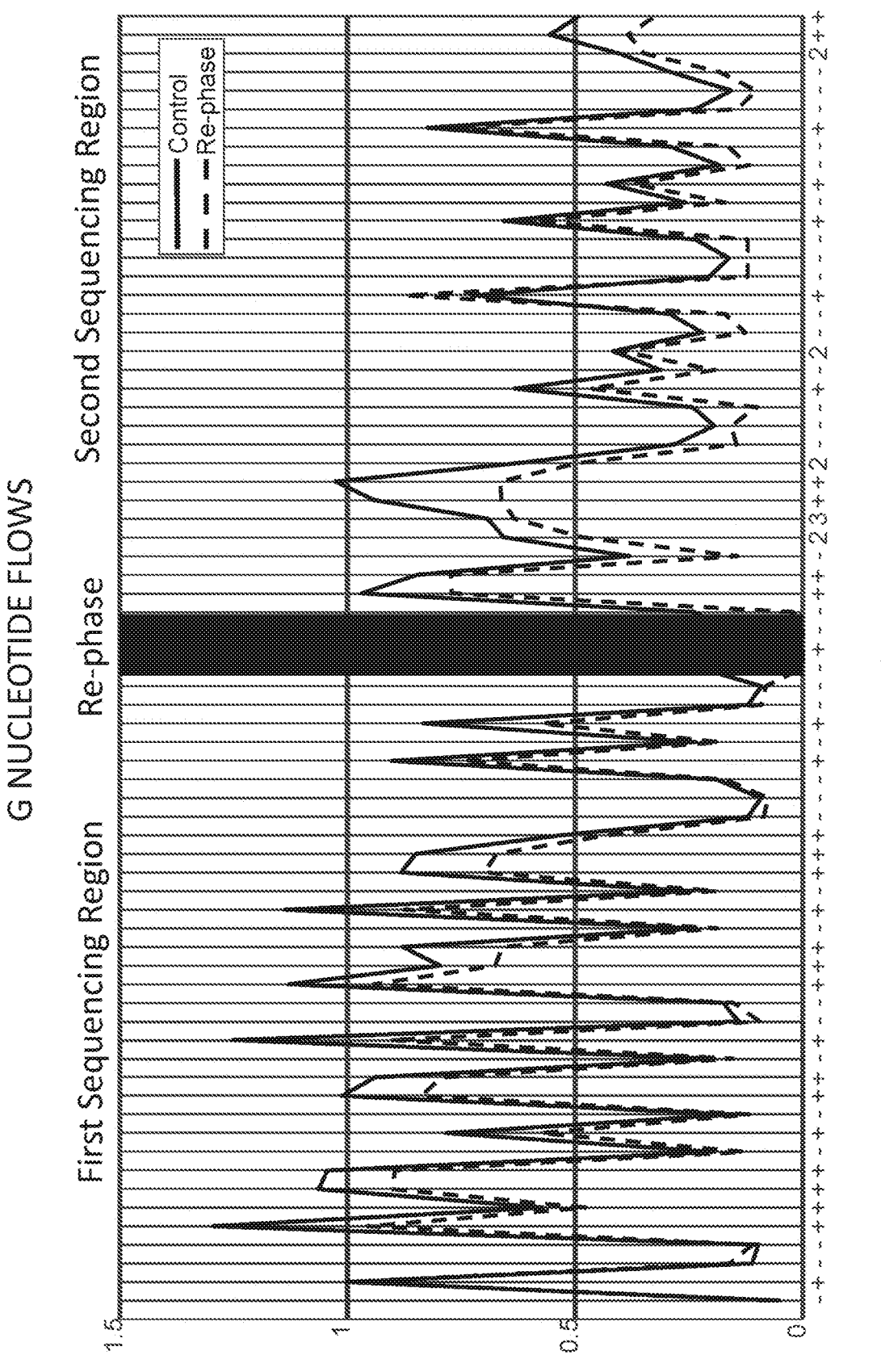
Figure 8C:
Figure 8D:
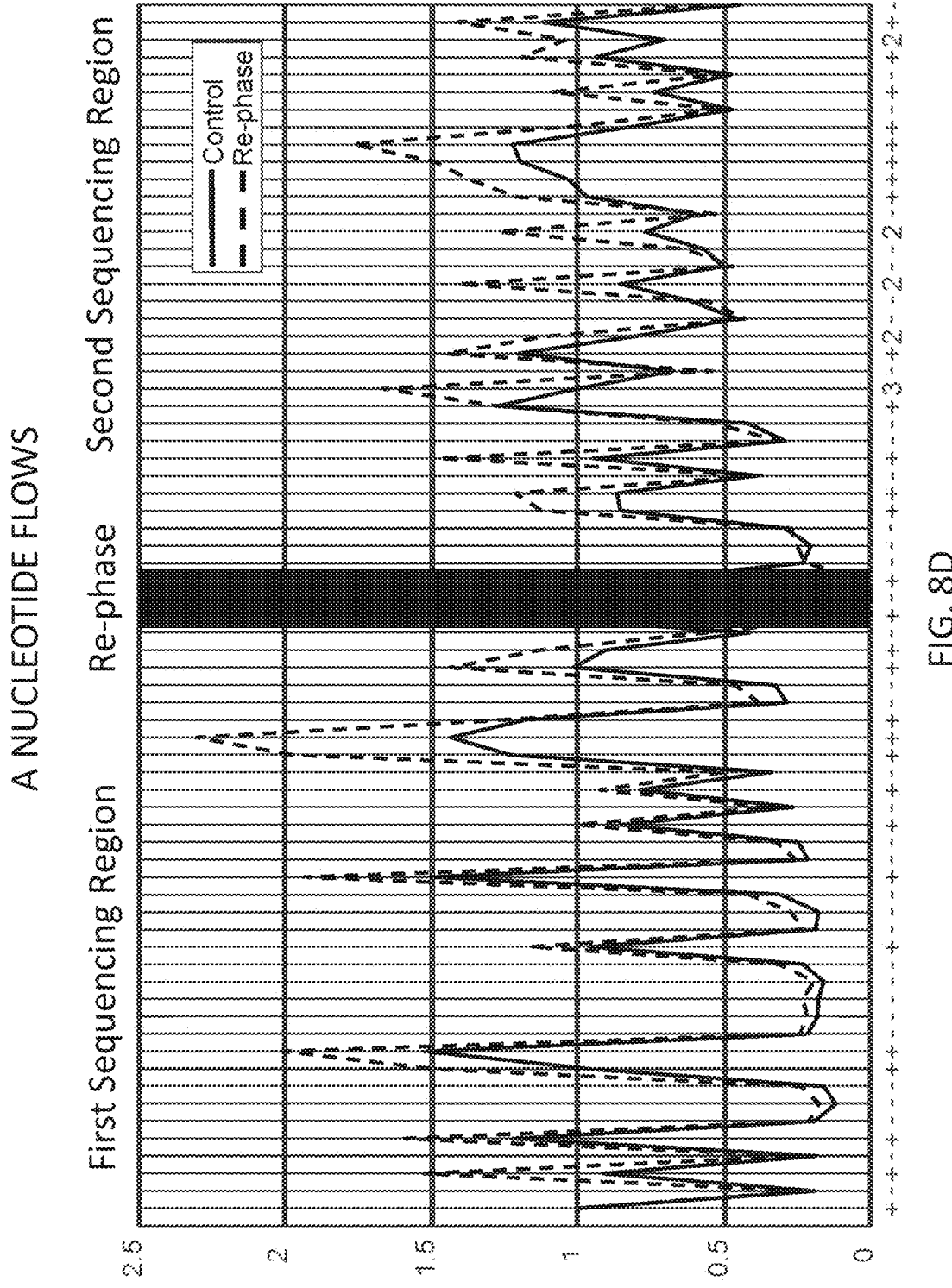

FIG. 8A shows sequencing data for C nucleotide flows for a polynucleotide sequenced using 34 sequencing cycles (each containing 4 sequencing flows), followed by a re-phasing cycle and an addition 34 sequencing flows for polynucleotide TF3. The data is overlaid with a sequencing data for C nucleotides for a polynucleotide having the same sequence, but without the re-phasing cycles. Similar sequencing data for G nucleotide flows (FIG. 8B), T nucleotide flows (FIG. 8C) and A nucleotide flows (FIG. 8D) is also shown.

Figure 9:
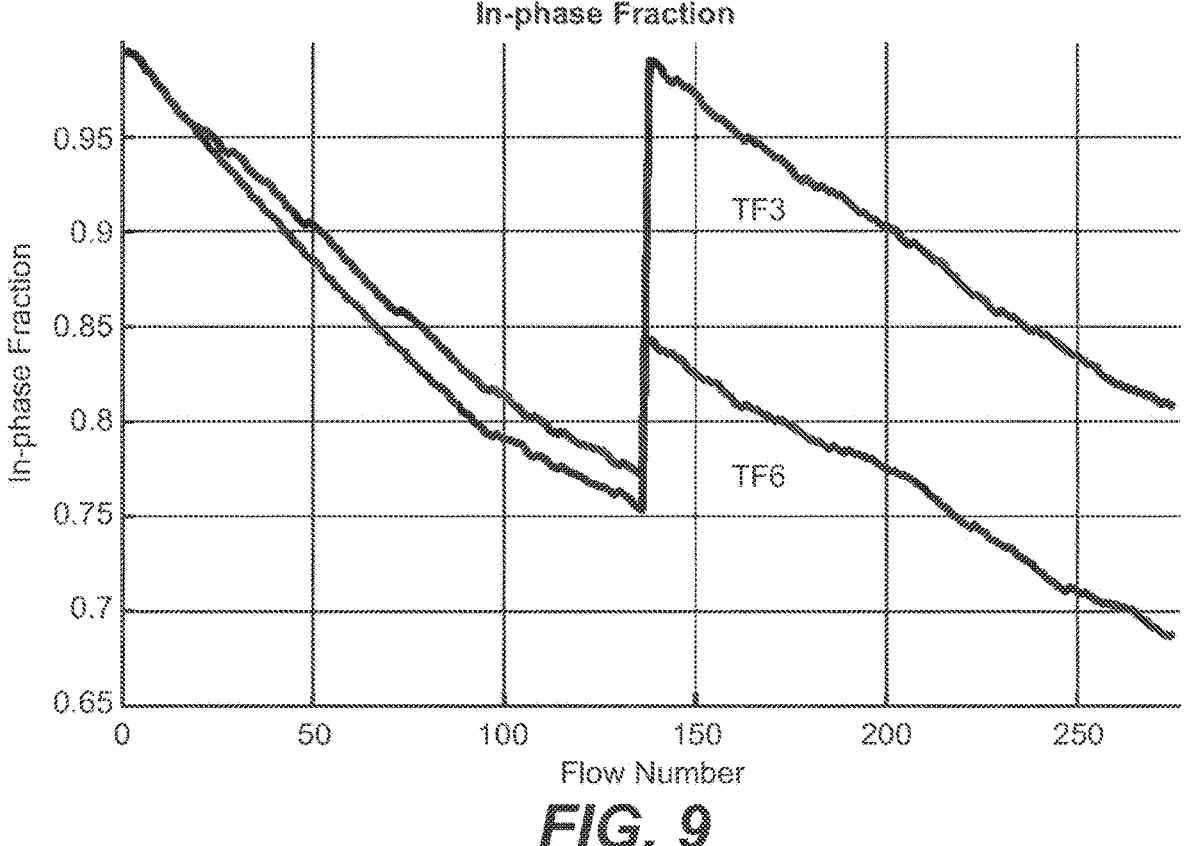

FIG. 9 compares the simulated fraction of in-phase sequencing primers against flow count for a sequencing cluster containing polynucleotide TF3 copies to a sequencing cluster containing polynucleotide TF6 copies. Re-phasing flows increased the fraction of in-phase sequencing primers for both sequences, but polynucleotide TF3 benefited from the re-phasing flows more than polynucleotide TF6.

Figure 10A:
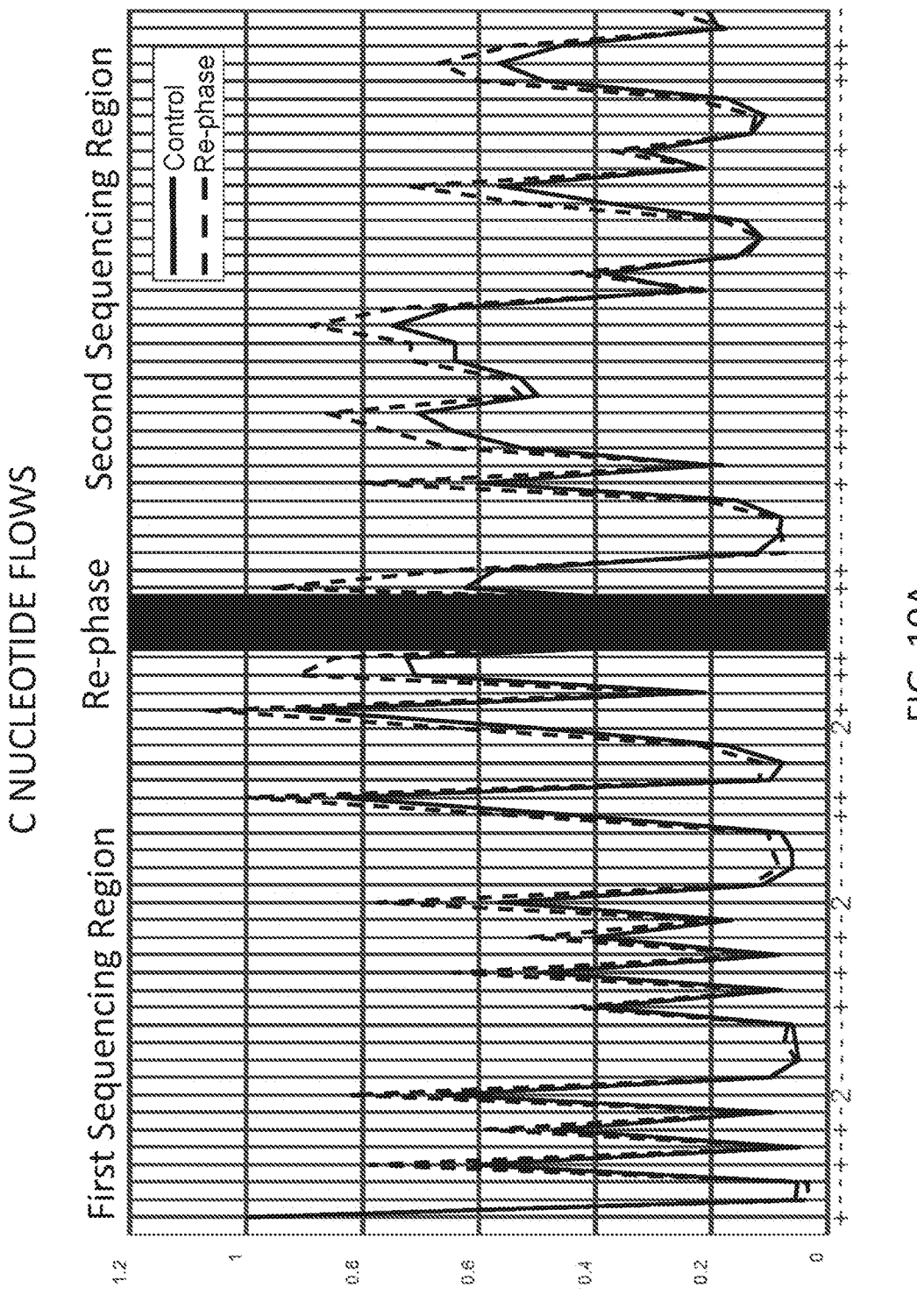

FIG. 10A shows sequencing data for C nucleotide flows for a polynucleotide sequenced using 34 sequencing cycles (each containing 4 sequencing flows), followed by a re-phasing cycle and an addition 34 sequencing flows for polynucleotide TF6. The data is overlaid with a sequencing data for C nucleotides for a polynucleotide having the same sequence, but without the re-phasing cycles. Similar sequencing data for G nucleotide flows (FIG. 10B), T nucleotide flows (FIG. 10C) and A nucleotide flows (FIG. 10D) is also shown.

DETAILED DESCRIPTION OF THE INVENTION

Described herein are methods of sequencing polynucleotides, including methods of synchronizing sequencing primers within a sequencing cluster (i.e., a sequencing colony). Using sequencing-by-synthesis methods, polynucleotides can copied (i.e., amplified) to form a sequencing cluster. Sequencing primers are hybridized to the polynucleotide copies within the sequencing cluster, and extended during the course of generating sequencing data. The polynucleotide/primer hybrids contacted with nucleotide flows according to a flow order, and incorporated into the extending sequencing primer strand according to the template strand (i.e., the polynucleotide in the starting cluster). At least a portion of the nucleotides in the flows are labeled, and incorporation of a nucleotide into the extending primer strand can be detected to generate sequencing data.

The chemical process of incorporating nucleotides into an extending prime is often imperfect, causing desynchronization among strands within a sequencing cluster. As the primer strands within the cluster extend, the primers can become out of phase, for example due to leading strands (caused by an over-incorporation of nucleotides in the extending sequencing primer) or lagging strands (caused by an under-incorporation of nucleotides into the extending sequencing primer). Desynchronization may result in signal degradation, and therefore reduced accuracy, when detecting the presence or absence of nucleotide incorporation into the extending primer as the read length increases.

Resynchronization can result in counteracting the signal loss, which allows for a longer effective read length. The methods described herein can include the use of one or more re-phasing flows, wherein a mixture of at least two different types of nucleotide bases are used in each of the one or more re-phasing flows. The re-phasing flows allow at least a portion of the sequencing strands to synchronize, resulting in a stronger signal when generating data within a sequenced region. This process of generating sequencing data by extending the primer through a sequencing region and re-phasing the sequencing primers, can be performed iteratively to generate a long-range sequencing read.

As further described herein, the more consecutive sequencing flows that are used prior to the one or more re-phasing flow, the more out of phase the sequencing primers become. The re-phasing flows can be used after a predetermined number of sequencing flows, or if the signal strength or signal-to-noise threshold falls below a predetermined signal strength threshold or predetermined signal-to-noise ratio threshold. The re-phasing flows can then increase the signal strength or signal-to-noise ratio when generating the sequencing data, providing more reliable sequencing data.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

A "flow cycle" refers to the order of separate nucleotide flow steps used to sequence a nucleic acid molecule using non-terminating nucleotides. The flow cycle may be divided into separate units termed a "flow." The flow cycle may be repeated a number of times to extend a sequencing primer. A "flow position" refers to the sequential position of a given separate nucleotide flow during the sequencing process.

The terms "individual," "patient," and "subject" are used synonymously, and refers to an animal including a human.

The term "label," as used herein, refers to a detectable moiety that is coupled to or may be coupled to another moiety, for example, a nucleotide or nucleotide analog. The label can emit a signal or alter a signal delivered to the label so that the presence or absence of the label can be detected. In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase, or protease). In some embodiments, the label is a fluorophore.

A "long-range sequencing read" is a sequencing read obtained from a single polynucleotide or cluster of polynucleotide copies that spans, from the first read base to the final read base, is at least 300 bases in length, regardless of read gaps between the first read base and the final read base.

The term "nucleotide," as used herein, generally refers to any nucleotide or nucleotide analog. The nucleotide may be naturally occurring (e.g., the canonical nucleotide bases A, G, T, U, C) or non-naturally occurring. The nucleotide analog may be a modified, synthesized or engineered nucleotide. The nucleotide analog may not be naturally occurring or may include a non-canonical base. The naturally occurring nucleotide may include a canonical base. The nucleotide analog may include a modified polyphosphate chain (e.g., triphosphate coupled to a fluorophore). The nucleotide analog may comprise a label. The nucleotide analog may be terminated (e.g., reversibly terminated). The nucleotide analog may comprise an alternative base. Non-standard nucleotides, nucleotide analogs, and/or modified analogs may include, but are not limited to, diaminopurine, 5-fluorouracil, 5-bromouracil, 5-chlorouracil, 5-iodouracil, hypoxanthine, xanthine, 4-acetylcytosine, 5-(carboxyhy-droxylmethyl)uracil, 5-carboxymethylaminomethyl-2-thiouridine, 5-carboxymethylaminomethyluracil, dihydrou-racil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methyl-guanine, 5-methylaminomethyluracil, 5-methoxyaminom-ethyl-2-thiouracil, beta-D-mannosylqueosine, 5'-methoxy-carboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methylu-racil, uracil-5-oxyacetic acid methylester, uracil-5-oxyacetic acid (v), 5-methyl-2-thiouracil, 3-(3-amino-3-N-2-carboxy-propyl) uracil, (acp3)w, 2,6-diaminopurine, ethynyl nucleo-tide bases, 1-propynyl nucleotide bases, azido nucleotide bases, phosphoroselenoate nucleic acids and the like. In some cases, nucleotides may include modifications in their phosphate moieties, including modifications to a triphos-phate moiety. Additional, non-limiting examples of modifi-cations include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modi-fications with selenium moieties (e.g., phosphoroselenoate nucleic acids). Nucleic acid molecules may also be modified at the base moiety (e.g., at one or more atoms that typically are available to form a hydrogen bond with a complemen-tary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow cova-lent attachment of amine reactive moieties, such as N-hy-droxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

A "non-terminating nucleotide" is a nucleic acid moiety that can be attached to a 3' end of a polynucleotide using a polymerase or transcriptase, and that can have another non-terminating nucleic acid attached to it using a poly-merase or transcriptase without the need to remove a pro-tecting group or reversible terminator from the nucleotide. Naturally occurring nucleic acids are a type of non-termi-nating nucleic acid. Non-terminating nucleic acids may be labeled or unlabeled.

The term "% sequence identity" may be used interchange-ably herein with the term "% identity" and may refer to the level of nucleotide sequence identity between two or more nucleotide sequences, when aligned using a sequence align-ment program. As used herein, 80% identity may be the same thing as 80% sequence identity determined by a defined algorithm and means that a given sequence is at least 80% identical to another length of another sequence. The % identity may be selected from, e.g., at least 60%, at least 65%, at least 70%, at least 75%, at least 80%, at least 85%, at least 90%, at least 95%, or at least 99% or more sequence identity to a given sequence. The % identity may be in the range of, e.g., about 60% to about 70%, about 70% to about 80%, about 80% to about 85%, about 85% to about 90%, about 90% to about 95%, or about 95% to about 99%.

The term "sequencing region" of a polynucleotide refers to a continuous sequenced segment. Multiple sequencing regions may be separated, for example, by a re-phasing region.

It is understood that aspects and variations of the inven-tion described herein include "consisting" and/or "consist-ing essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

Some of the analytical methods described herein include mapping sequences to a reference sequence, determining sequence information, and/or analyzing sequence informa-tion. It is well understood in the art that complementary sequences can be readily determined and/or analyzed, and that the description provided herein encompasses analytical methods performed in reference to a complementary sequence.

The section headings used herein are for organization purposes only and are not to be construed as limiting the subject matter described. The description is presented to enable one of ordinary skill in the art to make and use the invention and is provided in the context of a patent appli-cation and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The figures illustrate processes according to various embodiments. In the exemplary processes, some blocks are, optionally, combined, the order of some blocks is, option-ally, changed, and some blocks are, optionally, omitted. In some examples, additional steps may be performed in com-bination with the exemplary processes. Accordingly, the operations as illustrated (and described in greater detail below) are exemplary by nature and, as such, should not be viewed as limiting.

The disclosures of all publications, patents, and patent applications referred to herein are each hereby incorporated by reference in their entireties. To the extent that any reference incorporated by reference conflicts with the instant disclosure, the instant disclosure shall control.

Flow Sequencing

Sequencing data can be generated using a flow sequenc-ing method that includes extending a primer bound to a template polynucleotide molecule according to a predeter-mined flow order (which may be repeated in a plurality of flow cycles) where, in any given flow position, a single type of nucleotide is accessible to the extending primer. At least some of the nucleotides of the particular type can include a label, which upon incorporation of the labeled nucleotides into the extending primer renders a detectable signal. The resulting sequence by which such nucleotides are incorpo-rated into the extended primer should be the reverse comple-ment of the sequence of the template polynucleotide mol-ecule. In some embodiments, for example, sequencing data is generated using a flow sequencing method that includes extending a primer using labeled nucleotides, and detecting the presence or absence of a labeled nucleotide incorporated into the extending primer. Flow sequencing methods may also be referred to as "natural sequencing-by-synthesis," or "non-terminated sequencing-by-synthesis" methods. Exemplary methods are described in U.S. Pat. No. 8,772,473 and International Patent Application No. PCT/2020/031163, each of which is incorporated herein by reference in its entirety. While the following description is provided in reference to flow sequencing methods, it is understood that other sequencing methods may be used to sequence all or a portion of the sequenced region.

Flow sequencing includes the use of nucleotides to extend the primer hybridized to the polynucleotide. Nucleotides of a given base type (e.g., A, C, G, T, U, etc.) can be mixed with hybridized templates to extend the primer if a complementary base is present in the template strand. The nucleotides may be, for example, non-terminating nucleotides. When the nucleotides are non-terminating, more than one consecutive base can be incorporated into the extending primer strand if more than one consecutive complementary base is present in the template strand. The non-terminating nucleotides contrast with nucleotides having 3' reversible terminators, wherein a blocking group is generally removed before a successive nucleotide is attached. If no complementary base is present in the template strand, primer extension ceases until a nucleotide that is complementary to the next base in the template strand is introduced. At least a portion of the nucleotides can be labeled so that incorporation can be detected. Most commonly, only a single nucleotide type is introduced at a time (i.e., discretely added), although two or three different types of nucleotides may be simultaneously introduced in certain embodiments. This methodology can be contrasted with sequencing methods that use a reversible terminator, wherein primer extension is stopped after extension of every single base before the terminator is reversed to allow incorporation of the next succeeding base.

The nucleotides can be introduced at a determined order during the course of primer extension, which may be further divided into cycles. Nucleotides are added stepwise (i.e., in "flow steps"), which allows incorporation of the added nucleotide to the end of the sequencing primer of a complementary base in the template strand is present. During a flow step, a primer hybridized to the polynucleotide is extended using one or more nucleotides. A flow step may include a single base type or the simultaneous use (e.g., a mixture) of two or more different base types. The cycles may have the same order of nucleotides and number of different base types or a different order of nucleotides and/or a different number of different base types. Solely by way of example, the order of a flow cycle may be A-T-G-C, wherein A nucleobases are used in a first flow, T nucleobases are used in a second flow, G nucleobases are used in a third flow, and C nucleobases are used in a fourth flow, before the cycle is restarted beginning with A nucleobases in the first flow. Alternative orders may be readily contemplated by one skilled in the art. Between the introductions of different nucleotides, unincorporated nucleotides may be removed, for example by washing the sequencing platform with a wash fluid. For example, during sequencing, one or more labeled nucleotides can be incorporated into the extending primer, the hybridized template is washed, and a detector is used to detect a signal from the label of the nucleotide, which indicates whether the nucleotide has been incorporated into the extended primer.

A polymerase can be used to extend a sequencing primer by incorporating one or more nucleotides at the end of the primer in a template-dependent manner. In some embodiments, the polymerase is a DNA polymerase. The polymerase may be a naturally occurring polymerase or a synthetic (e.g., mutant) polymerase. The polymerase can be added at an initial step of primer extension, although supplemental polymerase may optionally be added during sequencing, for example with the stepwise addition of nucleotides or after a number of flow cycles. Exemplary polymerases include a DNA polymerase, an RNA polymerase, a thermostable polymerase, a wild-type polymerase, a modified polymerase, Bst DNA polymerase, Bst 2.0 DNA polymerase Bst 3.0 DNA polymerase, Bsu DNA polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase, and SeqAmp DNA polymerase.

The introduced nucleotides can include labeled nucleotides when determining the sequence of the template strand, and the presence or absence of an incorporated labeled nucleic acid can be detected to determine a sequence. The label may be, for example, an optically active label (e.g., a fluorescent label) or a radioactive label, and a signal emitted by or altered by the label can be detected using a detector. The presence or absence of a labeled nucleotide incorporated into a primer hybridized to a template polynucleotide can be detected, which allows for the determination of the sequence (for example, by generating a flowgram). In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. For example, the label may be cleaved after detection and before incorporation of the successive nucleotide(s). In some embodiments, the label (or linker) is attached to the nucleotide base, or to another site on the nucleotide that does not interfere with elongation of the nascent strand of DNA. In some embodiments, the linker comprises a disulfide or PEG-containing moiety.

Nucleotides used during a sequencing flow may include only labeled nucleotides, or may include a mixture of labeled and unlabeled nucleotides. For example, the portion of labeled nucleotides compared to total nucleotides may be about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 100%, about 95% or more, about 90% or more, about 80% or more about 70% or more, about 60% or more, about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about to about 0.025%, about 0.025% to about 0.05%, about 0.05% to about 0.1%, about to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

Sequencing data, such as a flowgram, can be generated based on the detection of an incorporated nucleotide and the order of nucleotide introduction. Take, for example, the flowing template sequences: CTG and CAG, and a repeating flow cycle of T-A-C-G (that is, sequential addition of T, A, C, and G nucleotides, which would be incorporated into the primer only if a complementary base is present in the template polynucleotide). A resulting flowgram is shown in Table 1, where 1 indicates incorporation of an introduced nucleotide and 0 indicates no incorporation of an introduced nucleotide. The flowgram can be used to determine the sequence of the template strand.

TABLE 1

| Sequence | Cycle 1 | | | | Cycle 2 | | | |
|---|---|---|---|---|---|---|---|---|
| | T | A | C | G | T | A | C | G |
| CTG | 0 | 0 | 0 | 1 | 0 | 1 | 1 | 0 |
| CAG | 0 | 0 | 0 | 1 | 1 | 0 | 1 | 0 |
| CCG | 0 | 0 | 0 | 2 | 0 | 0 | 1 | 0 |

The flowgram may be binary or non-binary. A binary flowgram detects the presence (1) or absence (0) of an incorporated nucleotide. A non-binary flowgram can more quantitatively determine a number of incorporated nucleotide from each stepwise introduction. For example, a sequence of CCG would incorporate two G bases, and any signal emitted by the labeled base would have a greater intensity as the incorporation of a single base. This is shown in Table 1. The non-binary flowgram also indicates the presence or absence of the base, but can provide additional information including the number of bases incorporated at the given step.

The number of sequencing flows or flow cycles can be increased or decreased to obtain the desired sequencing region length. Extension of the primer in the sequencing region can include one or more sequencing flows for stepwise extension of the primer using nucleotides having one or more different base types. For example, extension of the primer through any one of the sequencing regions may include between 1 and about 1000 sequencing flows, such as between 1 and about 10 sequencing flows, between about 10 and about 20 sequencing flows, between about 20 and about 50 sequencing flows, between about and about 100 sequencing flows, between about 100 and about 250 sequencing flows, between about 250 and about 500 sequencing flows, or between about 500 and about 1000 sequencing flows. The sequencing flows may be segmented into identical or different flow cycles. The number of bases incorporated into the primer in the sequencing region depends on the sequence of the sequencing region, and the flow cycle used to extend the primer in the sequencing region. For example, the sequencing region can be about 1 base to about 4000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, or about 2000 bases to about 4000 bases in length, or more, depending on the number of sequencing flows used in the sequencing region.

Prior to generating the sequencing data, the polynucleotide is hybridized to a sequencing primer to generate a hybridized template. The polynucleotide may be ligated to an adapter during sequencing library preparation. The adapter can include a hybridization sequence that hybridizes to the sequencing primer. For example, the hybridization sequence of the adapter may be a uniform sequence across a plurality of different polynucleotides, and the sequencing primer may be a uniform sequencing primer. This allows for multiplexed sequencing of different polynucleotides in a sequencing library.

The polynucleotide may be attached to a surface (such as a solid support) for sequencing. The polynucleotides may be amplified (for example, by bridge amplification or other amplification techniques) to generate polynucleotide sequencing clusters (i.e., sequencing colonies). The amplified polynucleotides within the cluster are substantially identical or complementary (some errors may be introduced during the amplification process such that a portion of the polynucleotides may not necessarily be identical to the original polynucleotide). That is, the each polynucleotide has sequence identity to a polynucleotide derived from (i.e., identity the polynucleotide or its complement) from the sample. Cluster formation allows for signal amplification so that the detector can accurately detect incorporation of labeled nucleotides for each colony. In some cases, the cluster is formed on a bead using emulsion PCR and the beads are distributed over a sequencing surface.

Examples for systems and methods for sequencing can be found in U.S. Pat. No. 10,344,328, International Publication No. WO 2019/099886, and International Publication No. WO 2020/186243, each of which is incorporated herein by reference in its entirety. In brief, an exemplary system can include a rotatable substrate that polynucleotides can be affixed to for sequencing. Polynucleotides from a sample can be attached to a support, such as a bead, and amplified on to the support to generate a plurality of polynucleotide copied (i.e., a sequencing cluster) on the support. The support, including the sequencing cluster, can then be attached to the rotatable substrate. In another variation, the polynucleotide for the sample is directly attached to the rotatable substrate and amplified on the substrate to generate the sequencing cluster. Reagents (such as wash buffers, primers, polymerase buffers, nucleotides in a sequencing flow or re-phasing flow, etc.) can be dispensed onto the rotatable substrate, for example proximal to the center of the rotatable substrate. The substrate can rotate, which causes the dispense reagents to flow outwardly, thereby contacting the sequencing cluster (and the polynucleotides within the sequencing cluster) with the reagent.

A given sequencing flow step can include one or more wash steps, one or more nucleotide dispensing steps, one or more sequencing signal detection steps, and one or more label cleavage steps. The amount of reagent and/or rotation speed of the rotatable substrate can vary depending on the desired incubation time. By way of example, a sequencing flow can include an initial wash, wherein a wash buffer is applied to the rotatable substrate rotates to flow the wash buffer across the surface of the rotatable substrate. The wash can be repeated one or more times, using the same or different amount of wash buffer, and the same or a different rotation speed of the rotatable substrate. A buffer containing nucleotides according to the sequencing flow is then dispensed on the rotatable substrate, and the substrate is rotate to flow the nucleotides across the substrate. According to some flow steps, a single nucleotide base type is used in the flow steps. Other flow steps may include the simultaneous use of two or more different types of nucleotide bases. If two or more different types of nucleotide bases are simultaneously used, the different type of nucleotide bases may be pre-mixed (i.e., before being dispensed onto the substrate), or may be dispensed separately onto the substrate and mixed on the substrate. Sequencing primers can be extended upon contact with the nucleotides in accordance with the template provided by the polynucleotide. A wash buffer can then be dispensed and the rotatable substrate rotated to wash away excess nucleotide. This wash step is optionally repeated one or more times using the same amount of wash buffer or a different amount, and by rotating the substrate at the same speed or a different speed. A sequencing signal can then be detected from the labeled nucleotides, for example by imaging the substrate.

The concentration of the nucleotides in different sequencing flows may be the same or different. For example, the concentration of T nucleotides in a T sequencing flow and C nucleotides in a C sequencing flow may be the same or different from the concentration of A nucleotides in an A nucleotide and/or G nucleotides in a G nucleotide flow. Different nucleotides can have different incorporation and/or over-incorporation rates, and the concentration of any given nucleotide may be selected by balancing the under- or over-incorporation of the nucleotide during sequencing (i.e., resulting in an acceptable number of leading or lagging primers). By way of example, the concentration of the nucleotides in the sequencing flow may be between about 0.1 μM and about 100 μM (for example, any one of about 0.1 μMm about 0.5 μM, about 1 μM, about 2 μM, about 3 μM, about 4 μM, about 5 μM, about 6 μM about 7 μM, about 8 μM, about 9 μM, about 10 μM, about 11 μM, about 12 μM, about 13 μM, about 14 μM, or about 15 μM, about 20 μM, about 25 μM, about 30 μM, about 40 μM, about 50 μM, about 60 μM, about 70 μM, about 80 μM, about 90 μM or about 100 μM, or any concentration between any of such concentrations).

After detecting the sequencing signal (e.g., by imaging), a cleavage buffer can then be applied to the substrate, and the substrate rotated to flow the cleavage buffer across the substrate and contact the sequencing clusters. The cleavage buffer contains reagent that cleave the label from the labeled nucleotides. The cleavage buffer can then be washed from the substrate one or more times by dispensing a wash buffer on the substrate and rotating the substrate. Optionally, the sequencing flow may include again dispensing the same nucleotide, which can help minimize lagging strands, which is subsequently washed using a wash buffer. A similar process is then repeated for the next sequencing flow.

The polynucleotide may be, in some embodiments, up to 100 bases (bp), 150 bp, 200 bp, 250 bp, 300 bp, 400 bp, 500 bp, 600 bp, 700 bp, 800 bp, 900 bp or 1,000 bp in length. In some embodiments, the length can be longer than 1,000 bp such as up to 1.1 kilobases (kb), 1.2 kb, 1.3 kb, 1.4 kb, 1.5 kb, 1.6 kb, 1.7 kb, 1.8 kb, 1.9 kb, or 2 kb or longer.

The polynucleotides used in the methods described herein may be obtained from any suitable biological source, for example a tissue sample, a blood sample, a serum sample, a cerebrospinal fluid sample, a plasma sample, a saliva sample, a fecal sample, or a urine sample. The polynucleotides may be DNA or RNA polynucleotides. In some embodiments, RNA polynucleotides are reverse transcribed into DNA polynucleotides prior to hybridizing the polynucleotide to the sequencing primer. In some embodiments, the polynucleotide is a cell-free DNA (cfDNA), such as a circulating tumor DNA (ctDNA) or a fetal cell-free DNA.

Libraries of the polynucleotides may be prepared through known methods. In some embodiments, the polynucleotides may be ligated to an adapter sequence. The adapter sequence may include a hybridization sequence that hybridized to the primer extended during the generated of the coupled sequencing read pair.

In some embodiments, the sequencing data is obtained without amplifying the nucleic acid molecules prior to establishing sequencing colonies (also referred to as sequencing clusters). Methods for generating sequencing colonies include bridge amplification or emulsion PCR. Methods that rely on shotgun sequencing and calling a consensus sequence generally label nucleic acid molecules using unique molecular identifiers (UMIs) and amplify the nucleic acid molecules to generate numerous copies of the same nucleic acid molecules that are independently sequenced. The amplified nucleic acid molecules can then be attached to a surface and bridge amplified to generate sequencing clusters that are independently sequenced. The UMIs can then be used to associate the independently sequenced nucleic acid molecules. However, the amplification process can introduce errors into the nucleic acid molecules, for example due to the limited fidelity of the DNA polymerase. In some embodiments, the nucleic acid molecules are not amplified prior to amplification to generate colonies for obtaining sequencing data. In some embodiments, the nucleic acid sequencing data is obtained without the use of unique molecular identifiers (UMIs).

Re-Phasing Sequencing Strands

The primer hybridized to the polynucleotide is extended through at least the first region (i.e., a sequencing region), a second region (i.e. a re-phasing region), and a third region (i.e., a second sequencing region) of the polynucleotide. Sequencing data associated with the sequence within the first region and/or the third region may be generated as discussed above. The primer is extended through the re-phasing region using one or more re-phasing flows containing at least two different types of nucleotide bases. The re-phasing flows may be used according to a re-phasing cycle comprising a plurality of re-phasing flows. Using re-phasing flows, at least a portion of the unsynchronized (leading or lagging) primers become resynched with the bulk of the extending sequencing primers, thereby generating a stronger sequencing signal when sequencing data is again collected in the subsequent sequencing region.

Figure 1:
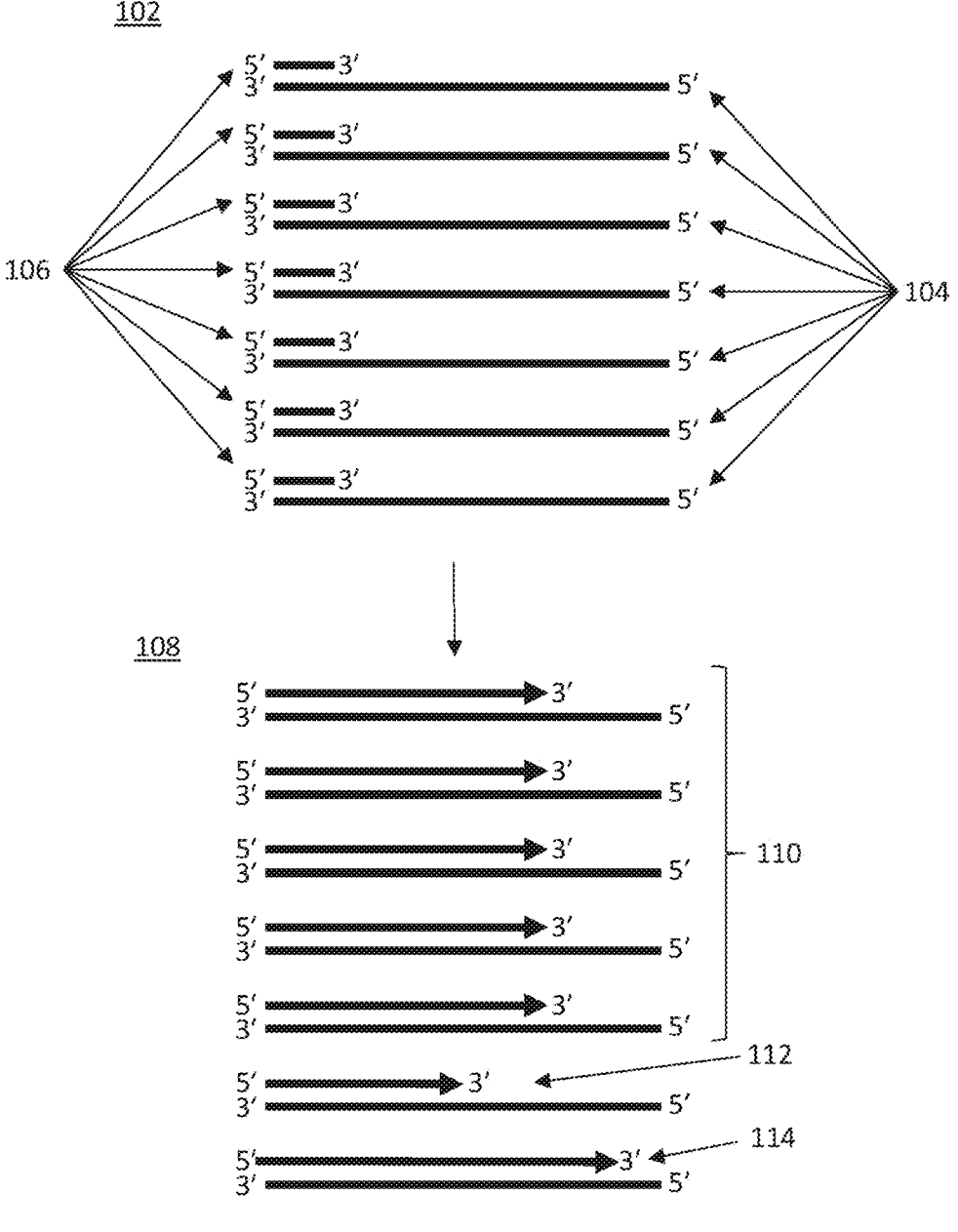
FIG. 1 shows flow sequencing of polynucleotides that can result in leading and lagging strands.

FIG. 1 illustrates flow sequencing of polynucleotides that can result in leading and lagging strands for which a re-phasing cycle would be beneficial. The top panel 102 shows a plurality of polynucleotide copies 104 hybridized to a sequencing primer 106. The sequencing primer 106 is extended during the flow sequencing process, with most primers incorporating nucleotides according to the template provided by the polynucleotide copies 104. The extended primers are shown in the bottom panel 108. As illustrated, most of the sequencing signal is coming from the synchronized primers 110, although some primers under-incorporated nucleotides (resulting in lagging strands 112) or over-incorporate nucleotides (resulting in leading strands 114).

During re-phasing, the nucleotides may be unlabeled (or a portion may be unlabeled) or labeled (or a portion may be labeled), or the nucleotides may include a mixture of labeled and unlabeled nucleotides. Further, detection of the incorporation of nucleotides after each re-phasing flow may be skipped. Optionally, the re-phasing flows may include labeled nucleotides (which may be at a proportion of total nucleotides used in the flow compared to the portion of labeled nucleotides used in a sequencing flow). If labeled nucleotides are used during the re-phasing cycle, signal can be detected at the end of the re-phasing cycle. The signal can be associated with base distance (i.e., the length of the re-phasing region) to determine or estimate the length of the re-phasing region.

As the primer is extended through the sequencing region, a sequencing signal (e.g., a signal strength or a signal-to-noise ratio) from the labeled nucleotides can decrease due to leading or lagging strands, and entering a re-phasing cycle can regain a significant portion of the signal strength. However, some sequencing data can be lost due to the re-phasing cycle. Too frequent re-phasing would result is significant data gaps, whereas infrequent re-phasing risks deterioration of the sequencing signal.

The re-phasing cycle (i.e., the use of the one or more re-phasing flows) can be initiated after a predetermined number of sequencing flows. That is, the primer can be extended through the sequencing region for a predetermined number of sequencing flows (or predetermined number of sequencing flow cycles, which corresponds to a predetermined number of sequencing flows when the sequencing flow cycle is set) using labeled nucleotides according to a sequencing cycle. The primer can then be extended through a re-phasing region using one or more re-phasing flows that includes the use of two or more different types of nucleotide bases before sequencing is re-initiated by extending the primer through a second sequencing region using labeled nucleotides according to the sequencing flow cycle. In some embodiments, the predetermined number of sequencing flows is between about 40 and about 200 (e.g., between about 40 and about 80, between about 80 and about 120, between about 120 and about 160, between about 160 and about 200, between about 200 and about 250, between about 250 and about 300, between about 300 and about 400, or between about 400 and about 500).

The predetermined number of sequencing flows prior to entering the re-phasing cycle can be selected based (i.e., be associated with) an expected sequencing signal (e.g., signal strength or signal-to-noise) loss. The sequencing signal is the signal detected from the labeled nucleotides. The expected sequencing signal loss may be empirically determined using similar control samples or by data simulation. An acceptable sequencing signal threshold can be set (for example, as acceptable to the user), and, given the sequencing signal loss expectation as sequencing progresses through the sequencing region of the polynucleotide, the expected number of sequencing flows that meets or crosses that threshold can be determined, which can used as the predetermined number of sequencing flows that triggers the re-phasing cycle.

Sequencing signal from the labeled nucleotides (e.g., signal strength and signal-to-noise ratios) are correlated with the proportion of unsynchronized primers, with a higher proportion of unsynchronized primers resulting in a lower sequencing signal. Unsynchronized primers are those primers that are not synchronized with the largest set of synchronized primers, for example due to leading or lagging primers. The predetermined number of sequencing flows used to extend the primer through the sequencing region before starting the re-phasing cycle can therefore be associated with an expected proportion of unsynchronized primers. The predetermined number of sequencing flows may be associated, for example, with a proportion of unsynchronized primers being about 0.1 to about 0.5 (for example, about 0.1 to about 0.2, about 0.2 to about 0.3, about 0.3 to about 0.4, or about 0.4 to about 0.5). Once the primer is extended through the sequencing region to the point at which the expected proportion of unsynchronized primers reaches a set threshold, the re-phasing cycle can be initiated.

The predetermined of sequencing flows prior to entering the re-phasing cycle may be associated with an expected length of the sequencing region. For example, it may be desirable to have a minimum length to the sequencing region before entering a re-phasing cycle. The re-phasing cycle can introduce gaps in the resulting sequencing data, and a continuous length of sequencing data may be advantageous for read alignments (e.g., for mapping the read to a reference sequence or to generate a consensus sequence). The expected number of sequenced bases per sequencing flow can be predicted by simulation using the sequencing flow cycle. For example, using a T-A-C-G flow cycle, the sequencing primer is extended in the sequencing region approximately 0.76 bases per flow assuming a random distribution of bases in proportion to their presence in the human genome. The primer can be extended through the re-phasing region according to a re-phasing cycle after and the primer has been extended through the sequencing region of an expected length based on the predetermined number of sequencing flows.

Optionally, the re-phasing cycle can be initiated using a real-time sequencing signal (e.g., signal strength or sequencing signal-to-noise ratio) measurement. As the primer is extended through the sequencing region and sequencing data is generated, the sequencing signal may deteriorate, for example due to out of phase sequencing primers. This can be monitored in real time (i.e., by measuring the sequencing signal or signal-to-noise ratio as the primer is extended through the sequencing region). When the sequencing signal falls below a predetermined threshold, re-phasing can be imitated.

The re-phasing flow cycle includes one or more re-phasing flows (e.g., between 2 and 12 re-phasing flows, or 1, 2, 3, 4, 5, 7, 8, 9, 10, 11, 12, or more re-phasing flows) that allow lagging and/or leads primers to synchronize with the larger portion of sequencing primers in the sequencing cluster. The re-phasing flows include a mixture of two or more (e.g., three) different types of nucleotide bases. In some embodiments, the re-phasing flow cycle comprises 1, 2, 3, 4, 5, or more re-phasing flows, each comprising two or three different types of nucleotide bases. In some embodiments, the re-phasing flow cycle comprises 3 re-phasing flows, each comprising two or three different types of nucleotide bases.

The re-phasing flow cycle is configured to increase the portion of synchronized extending primers after the re-phasing flow cycle. In some embodiments, the re-phasing flow cycle comprises, in any order, (i) a flow step comprising a mixture comprising A, C, and G nucleotides and omitting T (and/or U) nucleotides (also referred to as a "not T" (and/or "not U") step); (ii) a flow step comprising a mixture comprising T (and/or U), C, and G nucleotides and omitting A nucleotides (also referred to a "not A" step); (iii) a flow step comprising a mixture comprising T (and/or U), A, and G nucleotides and omitting C nucleotides (also referred to as a "not C" step); and (iv) a flow step comprising a mixture comprising T (and/or U), A, and C nucleotides and omitting G nucleotides (also referred to as a "not G" step).

In another example, the re-phasing flow cycle comprises three re-phasing flows. The re-phasing flows can include, for example, in any order, (i) a flow step comprising a mixture comprising A, C, and G nucleotides and omitting T (and/or U) nucleotides (also referred to as a "not T" (and/or "not U")

step); (ii) a flow step comprising a mixture comprising T (and/or U), A, and C nucleotides and omitting G nucleotides (also referred to as a "not G" step); and (iii) a flow step comprising a mixture comprising T (and/or U), A, and G nucleotides and omitting C nucleotides (also referred to as a "not C" step).

Other re-phasing flows can be determined. By way of example, in some embodiments, the re-phasing flows (in a re-phasing flow cycle) comprises, one or more of, in any order, (i) a flow step comprising a mixture comprising A and C nucleotides and omitting G and T (and/or U) nucleotides; (ii) a flow step comprising a mixture comprising T (and/or U) and G nucleotides, and omitting A and C nucleotides; (iii) a flow step comprising a mixture comprising A and G nucleotides and omitting T (and/or U) and C nucleotides; (iv) a flow step comprising a mixture comprising T (and/or U) and C nucleotides and omitting A and G nucleotides; (v) a flow step comprising a mixture comprising A and T (and/or U) nucleotides and omitting G and C nucleotides; (vi) a flow step comprising a mixture comprising C and G nucleotides and omitting A and T (and/or U) nucleotides; (vii) a flow step comprising a mixture comprising A, G, and C nucleotides and omitting T nucleotides; (viii) a flow step comprising a mixture comprising T (and/or U), A, and G nucleotides and omitting C nucleotides; (ix) a flow step comprising a mixture comprising C, T (and/or U), and A nucleotides and omitting G nucleotides; and/or (x) a flow step comprising a mixture of G, C, and T (and/or U) nucleotides and omitting A nucleotides.

Including a mixture of all four types of non-terminating nucleotides (i.e., a mixture comprising A, C, G, and T (and/or U)) can result in uncontrolled primer extension. However, a mixture of all four types of nucleotides, wherein three base types are non-terminating nucleotides and one base type includes a reversible terminator, can be used in a re-phasing flow cycle if the incubation time and concentration are controlled. For example, in some embodiments, the re-phasing flow cycle comprises (i) a flow step comprising a mixture comprising (or consisting of) non-terminating A nucleotides, non-terminating C nucleotides, non-terminating G nucleotides, and T (and/or U) nucleotides comprising a reversible terminator; or (ii) a flow step comprising a mixture comprising (or consisting of) non-terminating T (and/or U) nucleotides, non-terminating A nucleotides, non-terminating C nucleotides, and G nucleotides comprising a reversible terminator; or (iii) a flow step comprising a mixture comprising (or consisting of) non-terminating G nucleotides, non-terminating T (and/or U) nucleotides, non-terminating A nucleotides, and C nucleotides comprising a reversible terminator; or (iv) a flow step comprising a mixture comprising (or consisting of) non-terminating C nucleotides, non-terminating G nucleotides, non-terminating T (and/or) nucleotides, and A nucleotides comprising a reversible terminator. The primer is extended by incorporating nucleotides based on the template strand until a nucleotide comprising a reversible terminator is incorporated, which synchronizes extending primers within the sequencing cluster at the base with the reversible terminator. The reversible terminator can then be removed, and the sequencing process can then proceed with the synchronized primers.

A given re-phasing flow can include one or more wash steps and one or more nucleotide dispensing steps. The nucleotides in the re-phasing flows may be completely unlabeled, so no label cleavage or imaging is required. However, in some embodiments, a low concentration of labeled nucleotides may be used and signal detected and labels cleaved after the completion of the re-phasing cycle. The amount of reagent and/or rotation speed of the rotatable substrate can vary depending on the desired incubation time. By way of example, a sequencing flow can include an initial wash, wherein a wash buffer is applied to the rotatable substrate rotates to flow the wash buffer across the surface of the rotatable substrate. The wash can be repeated one or more times, using the same or different amount of wash buffer, and the same or a different rotation speed of the rotatable substrate. A buffer containing nucleotides according to the re-phasing flow (either a mixture of the two or more different nucleotide bases or as separately dispensed) is then dispensed on the rotatable substrate, and the substrate is rotate to flow the nucleotides across the substrate. Sequencing primers can be extended upon contact with the nucleotides in accordance with the template provided by the polynucleotide. A wash buffer can then be dispensed and the rotatable substrate rotated to wash away excess nucleotide. This wash step is optionally repeated one or more times using the same amount of wash buffer or a different amount, and by rotating the substrate at the same speed or a different speed. Optionally, the re-phasing flow may include again dispensing the same nucleotides, which is subsequently washed using a wash buffer. A similar process is then repeated for the next sequencing flow.

The concentration of nucleotides in the re-phasing flow (i.e., the sum of the concentration of each separate nucleotide base type in the re-phasing flow) can be higher than the concentration of nucleotides during a sequencing flow. This is because a higher number of nucleotides are generally incorporated during a re-phasing flow than a sequencing flow. In some embodiments, the concentration of nucleotides in the re-phasing flow is about 1.2×, about 1.5×, about 1.7×, about 2.0×, about 2.5×, about 3.0×, about 3.5×, about 4.0×, about 4.5×, or about 5.0×, or any value between these values, of the concentration of nucleotides in the sequencing flows. By way of example, the total concentration of the nucleotides in the re-phasing flow may be between about 0.1 μM and about 100 μM (for example, any one of about 0.1 μMm about 0.5 μM, about 1 μM, about 2 μM, about 3 μM, about 4 μM, about 5 μM, about 6 μM, about 7 μM about 8 μM, about 9 μM, about 10 μM, about 11 μM, about 12 μM, about 13 μM, about 14 μM, or about 15 μM, about 20 μM, about 25 μM, about 30 μM, about about 50 μM, about 60 μM, about 70 μM, about 80 μM, about 90 μM, or about 100 μM, or any concentration between any of such concentrations). The concentration of the different nucleotides used in a given re-phasing flow may be the same or different.

Figure 2:
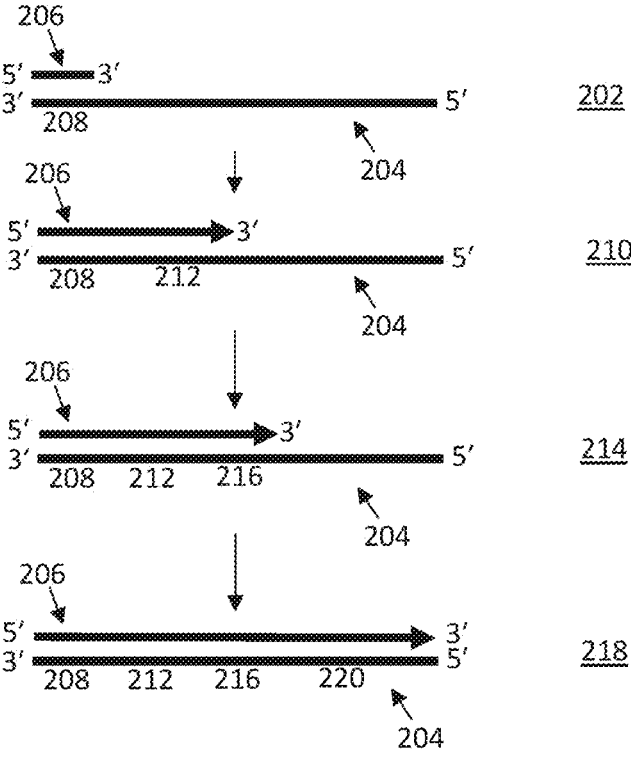
FIG. 2 a schematic of an exemplary method for sequenc-ing a polynucleotide with a re-phasing cycle.

FIG. 2 illustrates a schematic of an exemplary method for sequencing a polynucleotide with a re-phasing cycle. The figure shows only a single polynucleotide, and there does not explicitly show leading or lagging strands. However, when a number of copies of the polynucleotide are sequenced in parallel, leading and lagging strands can spontaneously result. At 202, a polynucleotide 204 is hybridized with a primer 206 to form a hybridized template. The polynucleotide can optionally include an adapter region 208, which may be ligated to the 3' of the target polynucleotide during sequencing library preparation. The adapter region 208 can include a hybridization region, and the primer 206 can hybridize to the hybridization region of the adapter region 208. At step 210, sequencing data for the first region 212 (i.e., the first sequencing region) of the polynucleotide 204 is generated by extending the primer 206 using labeled nucleotides, and detecting the presence or absence of an incorporated labeled nucleotide. The nucleotides used to extend the primer may further include unlabeled nucleotides, although labeled nucleotides are used to detect nucleotide incorporation for generating the sequencing data. The nucleotides can be added stepwise in one or more cycles according to a first region flow cycle to extend the primer 206 through the first region 212, and the hybridized template may be washed following a cycle step to remove unincorporated nucleotides prior to detecting the presence or absence of an incorporated labeled nucleotide. After a predetermined number of sequencing flows or when a measured sequencing signal falls below a predetermined sequencing signal threshold, a step 214 the primer 206 is extended through a second region 216 (i.e., a re-phasing region) of the polynucleotide 204 using one or more re-phasing flows. The re-phasing flows include a mixture of at least two different types of nucleotide bases, and can synchronize the primers. The primer can be extended in the re-phasing region without detecting the presence or absence of a label of a nucleotide. At step 218, sequencing data for the third region 220 (i.e., a second sequencing region) of the polynucleotide 204 is generated by extending the primer 206 using labeled nucleotides, and detecting the presence or absence of an incorporated labeled nucleotide. Generation of the sequencing data for the third region 220 may proceed in a similar manner as described for generating the sequencing data for the first region 212.

The sequencing process can alternate between the generating sequencing data form within a sequencing region of the polynucleotide and re-phasing within a re-phrasing region of the polynucleotide. For example, after the primer is extended through the third region (i.e., the second sequencing region), the primer can be extended through a fourth region (i.e., a second re-phasing region) using a re-phasing cycle, before being extended through a fifth region (i.e., a third sequencing region). The second re-phasing cycle may be triggered, for example, after a predetermined number of sequencing flows in the second sequencing region. The predetermined number of sequencing flows used to initiate the second re-phasing cycle need not be the same as the number of sequencing flows used to extend the primer within the first sequencing region and initiated the first re-phasing cycle. The second predetermined number of sequencing flows may be, for example, less than the first predetermined number of sequencing flows. This may be because re-phasing of leading and lagging strands might be incomplete, leading to lower initial sequencing signal when collecting sequencing data at the start of a later sequencing region than the start of a prior sequencing region. Therefore, the sequencing signal may fall below the threshold after few sequencing flows in a later segueing region than an earlier sequencing region. This can be iteratively performed for any number of sequencing regions and re-phasing regions to obtain long-range sequencing reads.

Primer extension using flow sequencing allows for long-range sequencing on the order of hundreds of bases in length. By including re-phasing cycles, the length of read can be significantly extended, as the re-phasing cycle allows for substantial signal strength recapture. Long-range sequencing can progress through numerous alternations of sequencing regions and re-phasing regions to extend the length of the sequencing read.

For example, the long-range sequencing ready can be generated by alternatingly generating sequencing data and re-phrasing the primers across a plurality of sequencing regions and a plurality of re-phrasing regions, wherein: generating sequencing data for a sequencing region comprises extending the primers through the sequencing region using labeled nucleotides according to a sequencing flow cycle, and detecting the presence or absence of an incorporated labeled nucleotide while extending the primers through the sequencing region; and re-phrasing the primers comprises extending the primers through a re-phasing region using one or more re-phasing flows, wherein a mixture of at least two different types of nucleotide bases are used in each of the one or more re-phasing flows.

The length of the long-range sequencing read (i.e., from the start of the first sequencing region to the end of the final sequencing region) may be at least 300 bases in length. For example, the length of the long-range sequencing read may be between about 300 to about 10,000 bases in length (such as between about 300 and about 600 bases in length, about 600 to about 1000 bases in length, about 1000 to about 2000 bases in length, about 2000 bases to about 3000 bases in length, about 3000 to about 4000 bases in length, about 4000 to about 5000 bases in length, about 5000 to about 6000 bases in length, about 6000 to about 7000 bases in length, about 7000 to about 8000 bases in length, about 8000 to about 9000 bases in length, or about 9000 to about 10,000 bases in length).

In some embodiments, the long-range sequencing read comprises 3, 4, 5, 6, 7, 8, 9, 10 or more sequencing regions, and 2, 3, 4, 5, 6, 7, 8, 9 or more re-phasing regions. In some embodiments, the long-range sequencing read is about 1000 bases in length or more (for example, about 1500 bases or more, 2000 bases or more, 3000 bases or more, 4000 bases or more, 7500 bases or more, about 10,000 bases or more, about 12,500 bases or more, about bases or more, or about 20,000 bases or more).

In some embodiments, the flow sequencing methods are used with rolling circle amplification (RCA) sequencing. RCA allows for formation of multiple copies of a nucleic acid molecule covalently attached in a linear sequence. See, for example, Dean et al., *Rapid Amplification of Plasmid and Phage DNA Using Phi29 DNA Polymerase and Multiply-Primed Rolling Circle Amplification*, Genome Research, vol. 11, pp. 1095-1099 (20001); and U.S. Pat. No. 5,714,320, the contents of each of which are incorporated herein by reference. RCA results in long polynucleotides, and the long-range sequencing methods described herein may be particularly beneficial for obtaining this sequencing data.

EXEMPLARY EMBODIMENTS

The following embodiments are exemplary and are not intended to limit the scope of the claimed invention.

Embodiment 1. A method of synchronizing sequencing primers within a sequencing cluster, comprising:

hybridizing primers to polynucleotide copies within a sequencing cluster;

extending the primers through a first region of the polynucleotide copies using nucleotides provided according to a first region flow order for a predetermined number of sequencing flows, wherein, during each sequencing flow in the first region flow order, a single type of nucleotide base is used and at least a portion of the nucleotides are labeled;

extending, after the predetermined number of sequencing flows, the primers through a second region of the polynucleotide copies using one or more re-phasing flows, wherein, during each of the one or more re-phasing flows, at least two different types of nucleotide bases are simultaneously used; and extending the primers through a third region of the polynucleotide copies using nucleotides provided according to a third region flow order comprising a plurality of sequencing flows, wherein, during each sequencing flow in the third region flow order, a single type of nucleotide base is used and at least a portion of the nucleotides are labeled.

Embodiment 2. The method of embodiment 1, wherein the predetermined number of sequencing flows is between about 40 and about 500.

Embodiment 3. The method of embodiment 1 or 2, wherein the predetermined number of sequencing flows is associated with a predetermined sequencing signal threshold.

Embodiment 4. The method of embodiment 1 or 2, wherein the predetermined number of sequencing flows is associated with an expected proportion of unsynchronized primers.

Embodiment 5. The method of embodiment 4, wherein the expected proportion of unsynchronized primers is between about 0.1 and about 0.5.

Embodiment 6. The method of embodiment 1 or 2, wherein the predetermined number of sequencing flows is associated with an expected length of the first region.

Embodiment 7. The method of any one of embodiments 1-6, further comprising:

extending, after the primers are extended through the third region for a second predetermined number of sequencing flows, the primers through a fourth region of the polynucleotide copies using one or more re-phasing flows, wherein, during each of the one or more re-phasing flows, at least two different types of nucleotide bases are simultaneously used; and extending the primers through a fifth region of the polynucleotide copies using nucleotides provided according to a fifth region flow order comprising a plurality of sequencing flows, wherein, during each sequencing flow in the fifth region flow order, a single type of nucleotide base is used and at least a portion of the nucleotides are labeled.

Embodiment 8. The method of embodiment 7, wherein the first predetermined number of sequencing flows and the second predetermined number of sequencing flows are the same.

Embodiment 9. The method of embodiment 7, wherein the second predetermined number of sequencing flows is less than the second predetermined number of sequencing flows.

Embodiment 10. The method of any one of embodiments 7-9, comprising generating sequencing data associated with a sequence of the fifth region by detecting the presence or absence of an incorporated labeled nucleotide while extending the primers through the fifth region.

Embodiment 11. A method of synchronizing sequencing primers within a sequencing cluster, comprising:

hybridizing primers to polynucleotide copies within a sequencing cluster;

extending the primers through a first region of the polynucleotide copies using nucleotides provided according to a first region flow order comprising a plurality of sequencing flows until a sequencing signal falls below a predetermined sequencing signal threshold, wherein, during each sequencing flow in the first region flow order, a single type of nucleotide base is used and at least a portion of the nucleotides are labeled;

extending, after the sequencing signal falls below the predetermined sequencing signal threshold, the primers through a second region of the polynucleotide copies using one or more re-phasing flows, wherein, during each of the one or more re-phasing flows, at least two different types of nucleotide bases are simultaneously used; and extending the primers through a third region of the polynucleotide copies using nucleotides provided according to a third region flow order comprising a plurality of sequencing flows, wherein, during each sequencing flow in the third region flow order, a single type of nucleotide base is used and at least a portion of the nucleotides are labeled.

Embodiment 12. The method of embodiment 11, wherein the sequencing signal is a sequencing signal intensity or a sequencing signal-to-noise ratio.

Embodiment 13. The method of embodiment 11 or 12, wherein the measured sequencing signal or measured sequencing signal-to-noise ratio is determined as the primer is extended through the first region.

Embodiment 14. The method of any one of embodiments 11-13, further comprising: extending, after the primers are extended through the third region until a second sequencing signal falls below a second sequencing signal threshold, the primers through a fourth region of the polynucleotide copies using one or more re-phasing flows, wherein, during each of the one or more re-phasing flows, at least two different types of nucleotide bases are simultaneously used; and extending the primers through a fifth region of the polynucleotide copies using nucleotides provided according to a fifth region flow order comprising a plurality of sequencing flows, wherein, during each sequencing flow in the fifth region flow order, a single type of nucleotide base is used and at least a portion of the nucleotides are labeled.

Embodiment 15. The method of embodiment 14, wherein the first sequencing signal threshold and the second sequencing signal threshold are the same.

Embodiment 16. The method of embodiment 14 or 15, comprising generating sequencing data associated with a sequence of the fifth region by detecting the presence or absence of an incorporated labeled nucleotide while extending the primers through the fifth region.

Embodiment 17. The method of any one of embodiments 1-16, wherein a mixture of three different types of nucleotide bases are used in at least one of the one or more re-phasing flows.

Embodiment 18. The method of any one of embodiments 1-17, wherein the one or more re-phasing flows comprises 2 to 12 re-phasing flows.

Embodiment 19. The method of any one of embodiments 1-18, wherein the one or more re-phasing flows comprises 3 or more re-phasing flows.

Embodiment 20. The method of any one of embodiments 1-19, wherein the one or more re-phasing flows comprises 3 re-phasing flows.

Embodiment 21. The method of any one of embodiments 1-20, wherein the one or more re-phasing flows comprises one or more of the following in any order:

(i) a flow comprising a mixture comprising A, C, and G nucleotides and omitting T nucleotides;

(ii) a flow comprising a mixture comprising T, C, and G nucleotides and omitting A nucleotides;

(ii) a flow comprising a mixture comprising T, A, and G nucleotides and omitting C nucleotides; and (iv) a flow comprising a mixture comprising T, A, and C nucleotides and omitting G nucleotides.

Embodiment 22. The method of any one of embodiments 1-21, comprising generating sequencing data associated with a sequence of the first region by detecting the presence or absence of an incorporated labeled nucleotide while extending the primers through the first region.

Embodiment 23. The method of any one of embodiments 1-21, comprising generating sequencing data associated with a sequence of the third region by detecting the presence or absence of an incorporated labeled nucleotide while extending the primers through the third region.

Embodiment 24. The method of any one of embodiments 1-23, wherein at least a portion of nucleotides in the one or more re-phasing flows are unlabeled.

Embodiment 25. The method of any one of embodiments 1-24, wherein nucleotides in the one or more re-phasing flows are unlabeled.

Embodiment 26. The method of any one of embodiments 1-25, wherein the first region flow order and the third region flow order are the same.

Embodiment 27. The method of any one of embodiments 1-25, wherein the first region flow order and the third region flow order are different.

Embodiment 28. The method of any one of embodiments 1-27, wherein the sequencing primer is extended through the first region of the polynucleotide by repeating the first region flow order a plurality of times.

Embodiment 29. The method of embodiment 28, wherein the first region flow order is repeated 2 times to about 50 times.

Embodiment 30. The method of any one of embodiments 1-29, wherein the sequencing primer is extended through the third region of the polynucleotide by repeating the third region flow order a plurality of times.

Embodiment 31. The method of embodiment 30, wherein the third region flow order is repeated 2 times to about 50 times.

Embodiment 32. The method of any one of embodiments 1-31, wherein primers are extended through three or more separate regions of the polynucleotide copies using re-phasing flows, and wherein sequencing data is generated for four or more separate regions of the polynucleotide copies.

Embodiment 33. The method of any one of embodiments 1-32, wherein the distance between the start of the first region of the polynucleotide copies and the end of a final region of the polynucleotide copies for which sequencing data is generated is at least 300 bases in length.

Embodiment 34. A method of generating a long-range sequencing read, comprising: hybridizing primers to poly-nucleotide copies within a sequencing cluster; and alternatingly generating sequencing data and re-phrasing the primers across a plurality of sequencing regions and a plurality of re-phrasing regions, wherein:
generating sequencing data for a sequencing region comprises extending the primers through the sequencing region using nucleotides provided according to a sequencing flow order, wherein, during each sequencing flow in the first region flow order, a single type of nucleotide base is used and at least a portion of the nucleotides are labeled, and detecting the presence or absence of an incorporated labeled nucleotide while extending the primers through the sequencing region; and
re-phrasing the primers comprises extending the primers through a re-phasing region using one or more re-phasing flows, wherein, during each of the one or more re-phasing flows, at least two different types of nucleotide bases are simultaneously used;
   wherein the distance between the start of a first sequencing region and the end of final sequencing region is at least 300 bases in length.

Embodiment 35. The method of embodiment 34, wherein the one or more re-phasing flows comprises between 2 and 12 re-phasing flows.

Embodiment 36. The method of embodiment 34 or 35, wherein the one or more re-phasing flows comprises 3 or more re-phasing flows.

Embodiment 37. The method of any one of embodiments 34-36, wherein the one or more re-phasing flows comprises 3 re-phasing flows.

Embodiment 38. The method of any one of embodiments 34-37, wherein the one or more re-phasing flows comprises one or more of the following in any order:

(i) a flow comprising a mixture comprising A, C, and G nucleotides and omitting T nucleotides;
   (ii) a flow comprising a mixture comprising T, C, and G nucleotides and omitting A nucleotides;
   (ii) a flow comprising a mixture comprising T, A, and G nucleotides and omitting C nucleotides; and
   (iv) a flow comprising a mixture comprising T, A, and C nucleotides and omitting G nucleotides.

Embodiment 39. The method of any one of embodiments 34-38, each sequencing region is between about 50 bases in length and about 500 bases in length.

Embodiment 40. The method of any one of embodiments 34-39, wherein the plurality of sequencing regions comprises at least four sequencing regions, and the plurality of re-phrasing regions comprises at last three re-phrasing regions.

Embodiment 41. The method of any one of embodiments 34-40, wherein the primers are extended through the sequencing region for a predetermined number of sequencing flows.

Embodiment 42. The method of embodiment 41, wherein the predetermined number of sequencing flows is between about 40 and about 200.

Embodiment 43. The method of embodiment 41 or 42, wherein the predetermined number of sequencing flows is associated with a predetermined sequencing signal threshold.

Embodiment 44. The method of embodiment 41 or 42, wherein the predetermined number of sequencing flows is associated with an expected proportion of unsynchronized primers.

Embodiment 45. The method of embodiment 44, wherein the expected proportion of unsynchronized primers is between about 0.5 and about 0.9.

Embodiment 46. The method of embodiment 41 or 42, wherein the predetermined number of sequencing flows is associated with an expected length of the sequencing region.

Embodiment 47. The method of any one of embodiments 34-40, wherein the primers are extended through the sequencing region until a sequencing signal falls below a predetermined sequencing signal threshold.

Embodiment 48. The method of any one of embodiments 34-47, wherein a mixture of three different types of nucleotide bases are used in at least one of the one or more re-phasing flows.

Embodiment 49. The method of any one of embodiments 34-48, wherein at least a portion of nucleotides in the one or more re-phasing flows are unlabeled.

Embodiment 50. The method of any one of embodiments 34-49, wherein nucleotides in the one or more re-phasing flows are unlabeled.

Embodiment 51. The method of any one of embodiments 34-50, wherein the distance between the start of a first sequencing region and the end of final sequencing region is between about 300 bases in length and about 5000 bases in length.

Embodiment 52. The method of any one of embodiments 1-51, wherein nucleotides used to extend the primers are non-terminating nucleotides.

Embodiment 53. The method of any one of embodiments 1-52, wherein at least a portion of the nucleotides used in the re-phasing flows are unlabeled.

Embodiment 54. The method of any one of embodiments 1-53, wherein nucleotides used in the re-phasing flows are unlabeled.

Embodiment 55. The method of any one of embodiments 1-54, wherein nucleotides used in the one or more re-phasing flows are used at a higher concentration than nucleotides used in the sequencing flows.

Embodiment 56. The method of any one of embodiments 1-55, wherein the polynucleotide copies are attached to a rotatable substrate.

Embodiment 57. A method of synchronizing sequencing in a colony, comprising:

(a) providing a sequencing colony comprising a plurality of copies of nucleic acid molecules, wherein each nucleic acid molecule of the plurality of copies comprises a first region, a second region, and a third region;

(b) hybridizing a plurality of primers to the plurality of copies;

(c) extending the plurality of primers through the first region by, in each flow step of a plurality of first flow cycles having a first predetermined number of flow steps, providing a first plurality of nucleotides of a single base type, wherein at least a portion of the first plurality of nucleotides is labeled;

(d) extending, after the first predetermined number of flow steps, the plurality of primers through the second region by, in each flow step of a plurality of second flow cycles, providing a second plurality of nucleotides comprising at least two base types; and (e) extending the plurality of primers through the third region by, in each flow step of a plurality of third flow cycles, providing a third plurality of nucleotides of a single base type, wherein at least a portion of the third plurality of nucleotides is labeled.

Embodiment 58. The method of embodiment 57, wherein the first predetermined number of flow steps is between about 40 and about 500.

Embodiment 59. The method of embodiment 57 or 58, wherein the first predetermined number of flow steps is associated with a predetermined sequencing signal threshold.

Embodiment 60. The method of embodiment 57 or 58, wherein the first predetermined number of flow steps is associated with an expected proportion of unsynchronized primers.

Embodiment 61. The method of embodiment 60, wherein the expected proportion of unsynchronized primers is between about 0.1 and about 0.5.

Embodiment 62. The method of embodiment 57 or 58, wherein the first predetermined number of sequencing flow steps is associated with an expected length of the first region.

Embodiment 63. The method of any one of embodiments 57-62, wherein the plurality of third flow cycles has a second predetermined number of flow steps, the method further comprising:

(f) extending, after the second predetermined number of flow steps, the plurality of primers through a fourth region of the plurality of copies by, in each flow step of a plurality of fourth flow cycles, providing a fourth plurality of nucleotides comprising at least two base types; and (g) extending the plurality of primers through a fifth region of the plurality of copies by, in each flow step of a plurality of fifth flow cycles, providing a fifth plurality of nucleotides of a single base type, wherein at least a portion of the fifth plurality of nucleotides is labeled.

Embodiment 64. The method of embodiment 63, wherein the first predetermined number of flow steps and the second predetermined number of flow steps are the same.

Embodiment 65. The method of embodiment 63, wherein the second predetermined number of flow steps is less than the first predetermined number of flow steps.

Embodiment 66. The method of any one of embodiments 63-65, comprising sequencing the fifth region by detecting the presence or absence of an incorporated labeled nucleotide while extending the primers through the fifth region.

Embodiment 67. A method of synchronizing sequencing, comprising:

(a) providing a sequencing colony comprising a plurality of copies of nucleic acid molecules, wherein each nucleic acid molecule of the plurality of copies comprises a first region, a second region, and a third region;

(b) hybridizing a plurality of primers to the plurality of copies;

(c) extending the plurality of primers through the first region by, in each flow step of a plurality of first flow cycles, (i) providing a first plurality of nucleotides of a single base type, wherein at least a portion of the first plurality of nucleotides are labeled, and (ii) detecting a signal indicative of incorporation, or lack thereof, of a labeled nucleotide of the first plurality of nucleotides in the plurality of primers, until the signal falls below a first predetermined sequencing signal threshold;

(d) extending, after the signal falls below the first predetermined sequencing signal threshold, the plurality of primers through the second region by, in each flow step of a plurality of second flow cycles, providing a second plurality of nucleotides comprising at least two base types; and (e) extending the plurality of primers through the third region by, in each flow step of a plurality of third flow cycles, providing a third plurality of nucleotides of a single base type, wherein at least a portion of the third plurality of nucleotides is labeled.

Embodiment 68. The method of embodiment 67, wherein the signal is a sequencing signal intensity or a sequencing signal-to-noise ratio.

Embodiment 69. The method of embodiment 68, further comprising detecting one or more signals or sequencing signal-to-noise ratio as the primers are extended through the first region in (c).

Embodiment 70. The method of any one of embodiments 67-69, wherein the plurality of primers is extended through the third region until a second signal detected falls below a second predetermined sequencing signal threshold, the method further comprising:

(f) extending, after the second signal falls below the second predetermined sequencing signal threshold, the plurality of primers through a fourth region of the plurality of copies by, in each flow step of a plurality of fourth flow cycles, providing a fourth plurality of nucleotides comprising at least two base types; and (g) extending the plurality of primers through a fifth region of the plurality of copies by, in each flow step of a plurality of fifth flow cycles, providing a fifth plurality of nucleotides of a single base type, wherein at least a portion of the fifth plurality of nucleotides is labeled.

Embodiment 71. The method of embodiment 70, wherein the first predetermined sequencing signal threshold and the second predetermined sequencing signal threshold are the same.

Embodiment 72. The method of embodiment 70 or 71, further comprising sequencing the fifth region by detecting the presence or absence of an incorporated labeled nucleotide while extending the primers through the fifth region.

Embodiment 73. The method of any one of embodiments 57-72, wherein a mixture of three different base types is used in at least one flow step of the plurality of second flow cycles.

Embodiment 74. The method of any one of embodiments 57-73, wherein one or more flow steps of the plurality of second flow cycles comprise 2 to 12 re-phasing flow steps.

Embodiment 75. The method of any one of embodiments 57-74, wherein one or more flow steps of the plurality of second flow cycles comprise 3 or more re-phasing flow steps.

Embodiment 76. The method of any one of embodiments 57-75, wherein one or more flow steps of the plurality of second flow cycles comprise 3 re-phasing flow steps.

Embodiment 77. The method of any one of embodiments 57-76, wherein one or more flow steps of the plurality of second flow cycles comprise one or more of the following in any order:

(i) a flow step comprising a mixture comprising A, C, and G nucleotides and omitting T nucleotides;

(ii) a flow step comprising a mixture comprising T, C, and G nucleotides and omitting A nucleotides;

(ii) a flow step comprising a mixture comprising T, A, and G nucleotides and omitting C nucleotides; and (iv) a flow step comprising a mixture comprising T, A, and C nucleotides and omitting G nucleotides.

Embodiment 78. The method of any one of embodiments 57-77, further comprising sequencing the first region by detecting the presence or absence of an incorporated labeled nucleotide while extending the primers through the first region.

Embodiment 79. The method of any one of embodiments 57-78, comprising sequencing the third region by detecting the presence or absence of an incorporated labeled nucleotide while extending the primers through the third region.

Embodiment 80. The method of any one of embodiments 57-79, wherein at least a portion of nucleotides provided in the plurality of second flow cycles are unlabeled.

Embodiment 81. The method of any one of embodiments 57-80, wherein a first flow order of the plurality of first flow cycles and a third order of the plurality of third flow cycles are the same.

Embodiment 82. The method of any one of embodiments 57-80, wherein a first flow order of the plurality of first flow cycles and a third order of the plurality of third flow cycles are different.

Embodiment 83. The method of any one of embodiments 57-82, wherein the plurality of primers is extended through the first region by repeating a first flow order a plurality of times in the plurality of first flow cycles.

Embodiment 84. The method of embodiment 83, wherein the first flow order is repeated 2 times to about 50 times.

Embodiment 85. The method of any one of embodiments 57-84, wherein the plurality of primers is extended through the third region by repeating a third flow order a plurality of times in the plurality of third flow cycles.

Embodiment 86. The method of embodiment 85, wherein the third flow order is repeated 2 times to about 50 times.

Embodiment 87. The method of any one of embodiments 57-86, wherein the plurality of primers is extended through three or more separate regions of the plurality of copies using a plurality of re-phasing flow steps, and wherein sequencing data is generated for four or more separate regions of the polynucleotide copies.

Embodiment 88. The method of any one of embodiments 57-87, wherein a distance between a start of the first region and an end of a final region of the plurality of copies for which sequencing data is generated is at least 300 bases in length.

EXAMPLES

The application may be better understood by reference to the following non-limiting examples, which is provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Figures 3A, 3B:
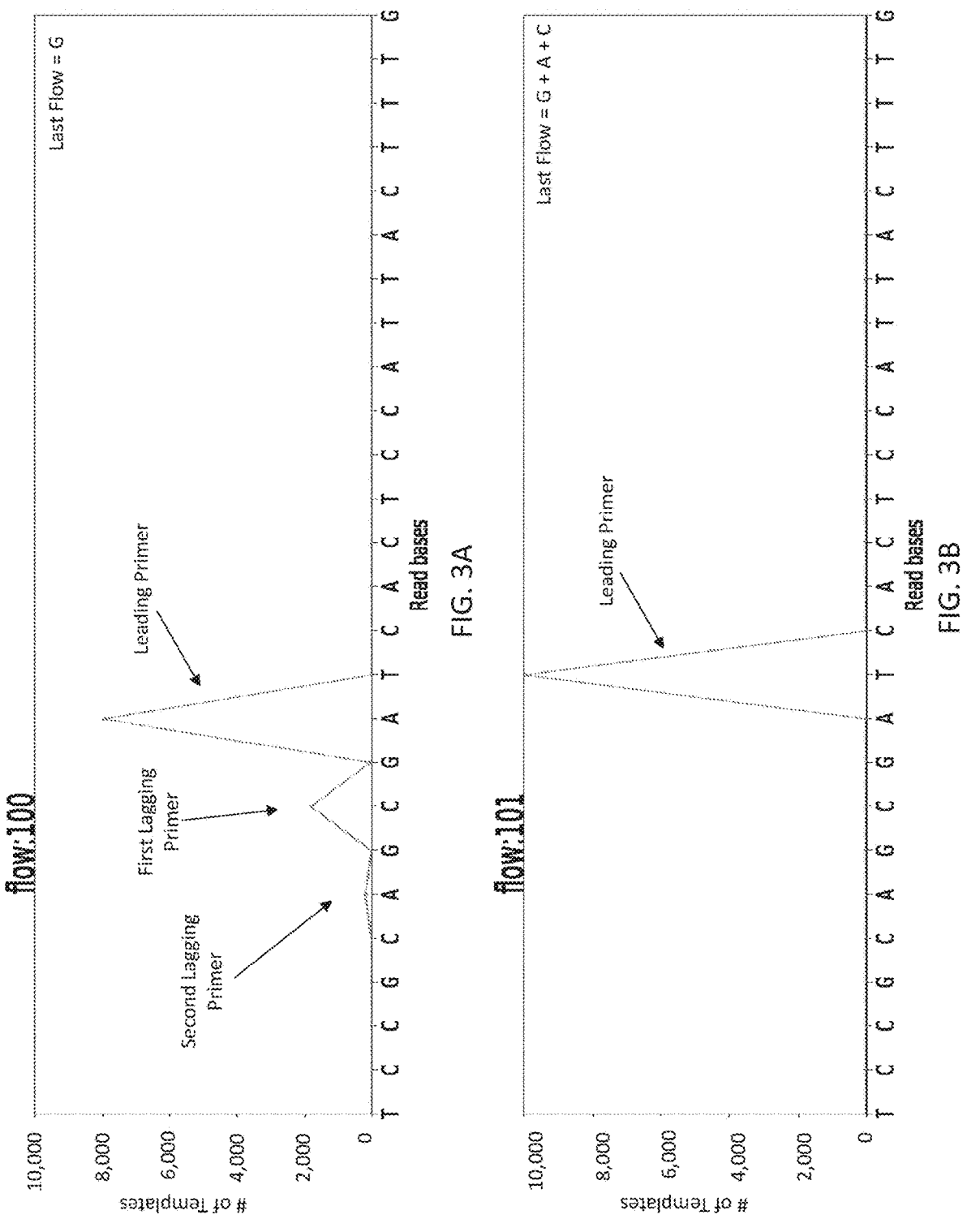
FIG. 3A-3E shows the number of primers extended against identical polynucleotide templates in an exemplary simulated sequencing protocol after 100 nucleotide flows (FIG. 3A), and re-phasing flows designed to synchronize primers within a sequencing cluster. The illustrated rephasing flow cycle is a four-step order that includes nucleotide flow 101 (FIG. 3B), flow 102 (FIG. 3C), flow 103 (FIG. 3D), and flow 104 (FIG. 3E).
Figures 3C, 3D:
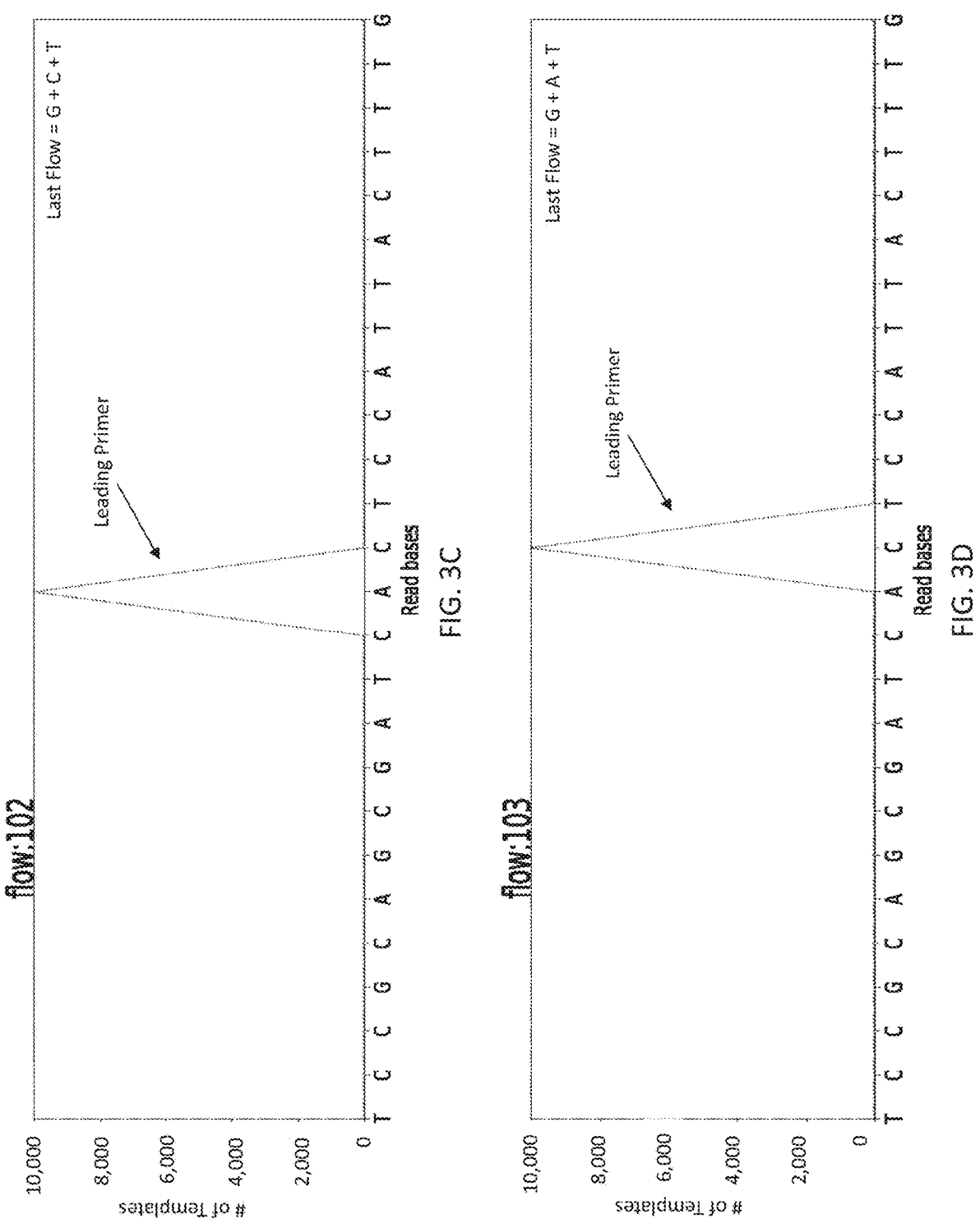
Figures 3E, 4A:
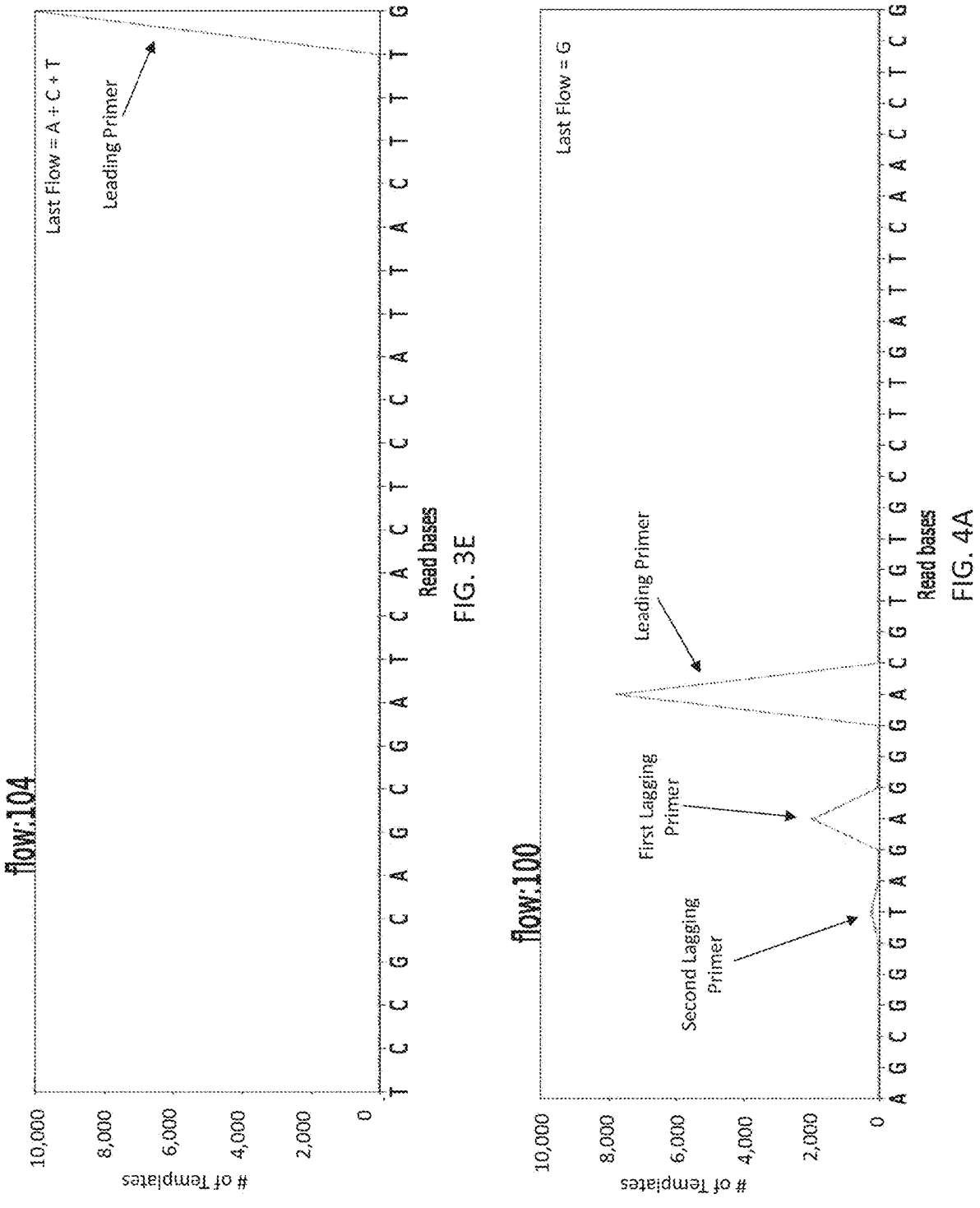
FIG. 4A-4E shows the number of primers extended against identical polynucleotide templates in another exemplary simulated sequencing protocol after 100 nucleotide flows (FIG. 4A), and re-phasing flows designed to synchronize primers within a sequencing cluster. The illustrated re-phasing flow cycle is a four-step order that includes nucleotide flow 101 (FIG. 4B), flow 102 (FIG. 4C), flow 103 (FIG. 4D), and flow 104 (FIG. 4E).
Figures 4B, 4C:
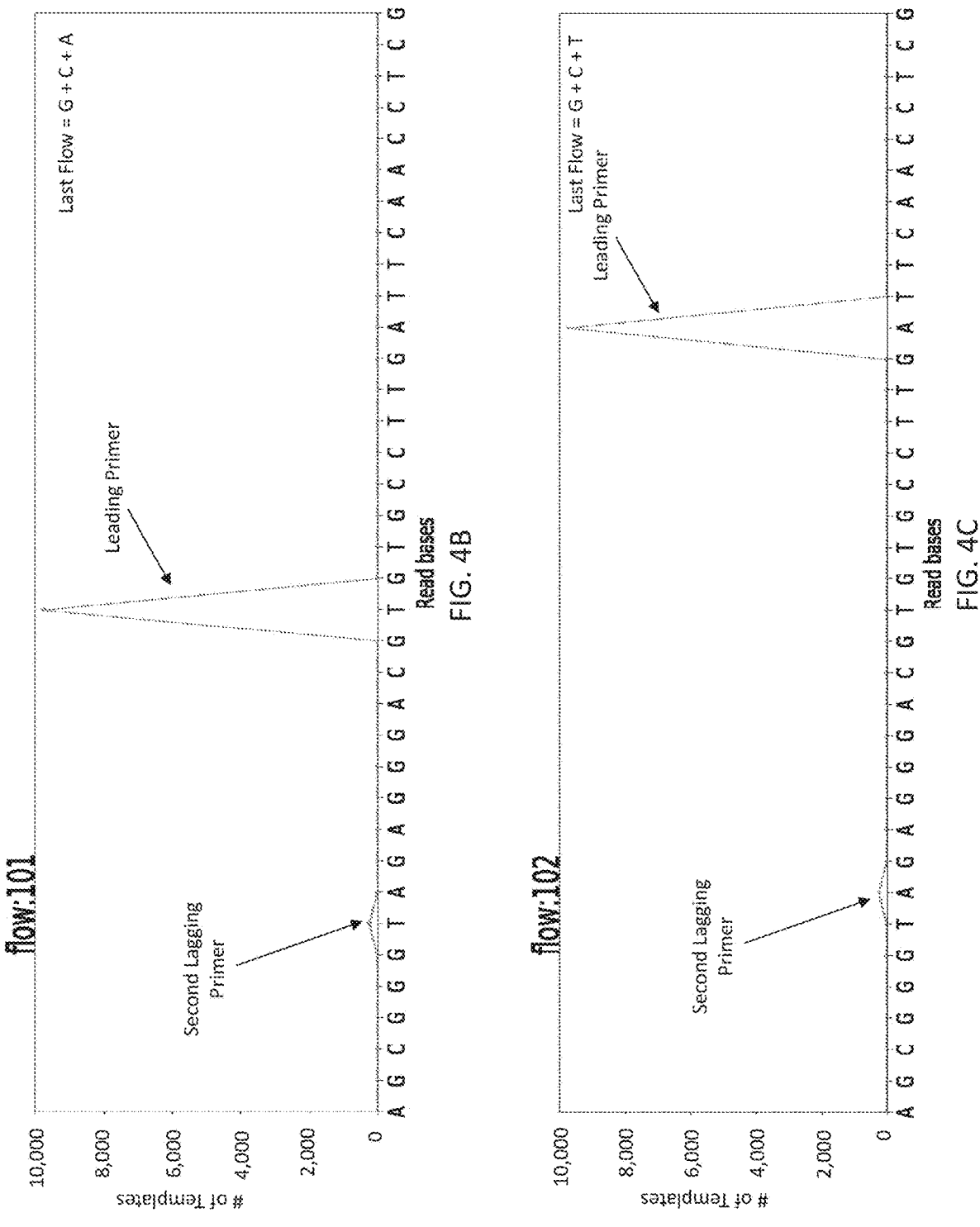
Figures 4D, 4E:
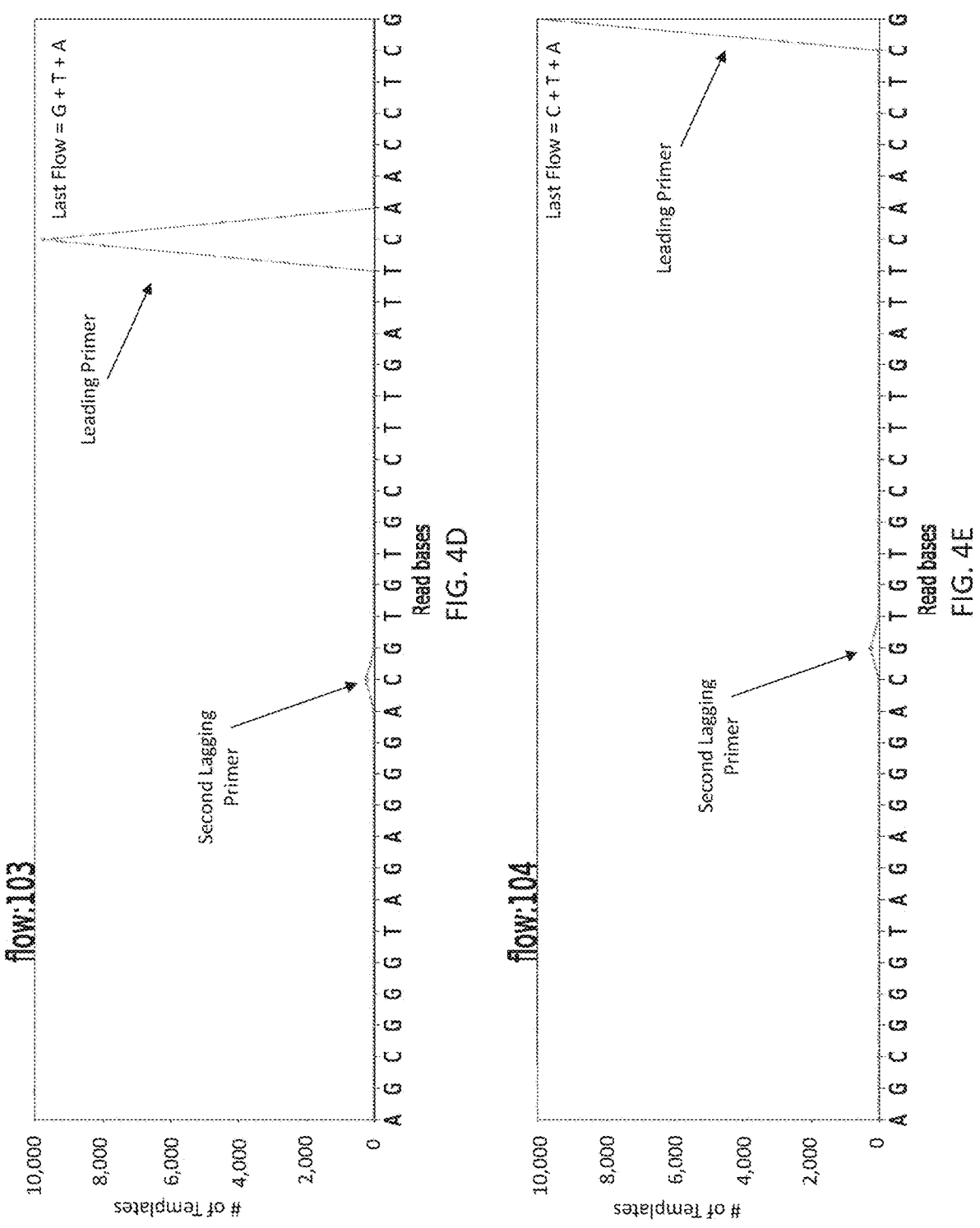
Figures 5A, 5B:
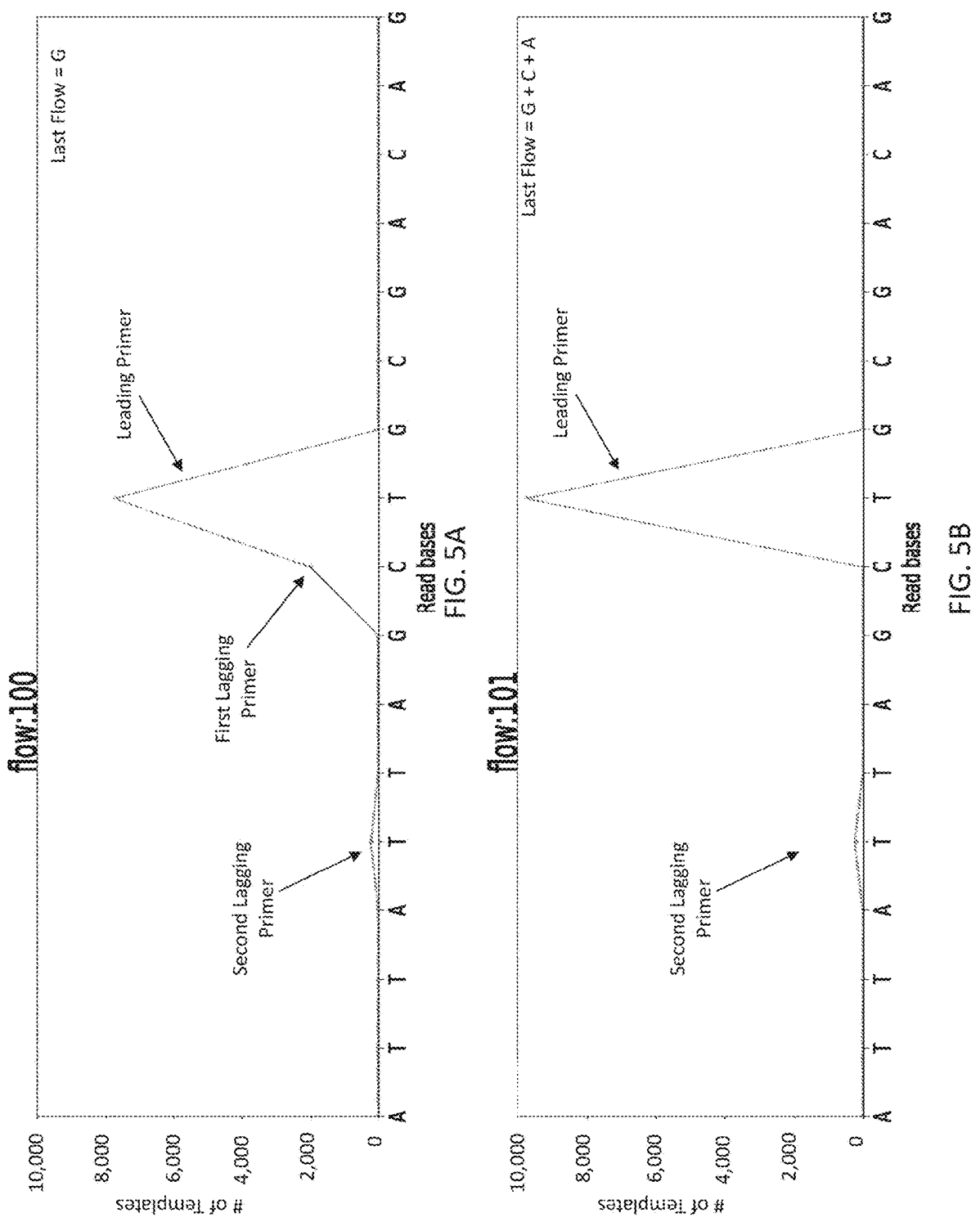
Figure 5E:
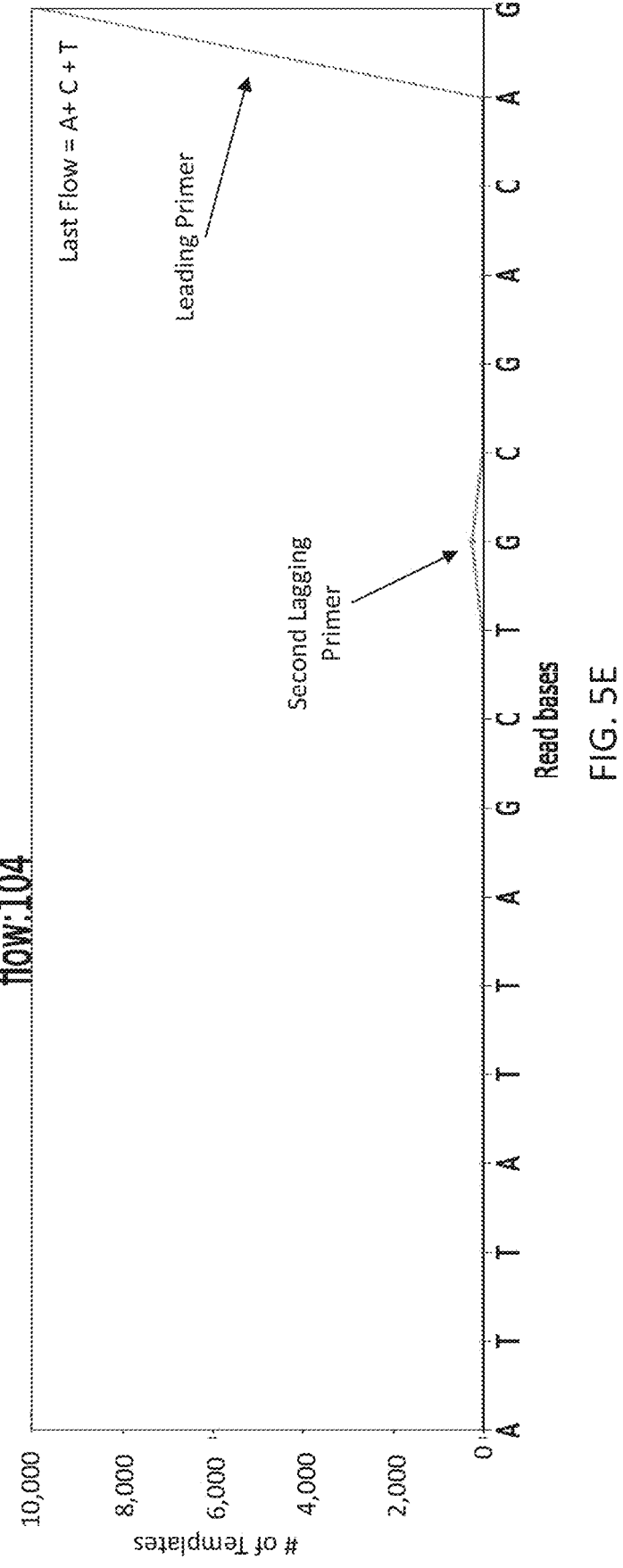

Sequencing-by-synthesis methods generally have imperfect incorporation of nucleotides into the extending primer. Over time, within a sequencing cluster, the primers can become desynchronized, resulting in degrading signal and lower confidence in making base incorporation calls. Primer desynchronization within a sequencing cluster was simulated by assuming a sequencing cluster with 10,000 identical template strands, and sequencing the template strands using non-terminating nucleotides assuming a flow cycle of A-C-T-G, wherein each flow has a single nucleotide. The probability of failed incorporation (i.e., a nucleotide did not incorporate into the extending primer strand when the template indicated the nucleotide should have been incorporated) was set to 0.5%. FIG. 3A shows the number of primers (strands) extended at each read base after 100 flow steps, with the 100th flow having a G non-terminating nucleotide. The sequencing cluster includes templates hybridized to a leading sequencing primer wherein the G nucleotide was incorporated into the extending primer such that the next expected incorporated nucleotide is an A, a first lagging primer wherein a G nucleotide was incorporated into the extending primer such that the next expected incorporated nucleotide is a C, and a second lagging primer no nucleotide was incorporated into the extending primer from the 100th flow. The first lagging primer and second lagging primer represent primers for which incorporation of an expected nucleotide into the extending primer failed at some point during the sequencing process. Synchronization of the extension primers using a re-phasing flow cycle. At flow 101, the primer was extended using a mixture of G, C, and A non-terminating nucleotides (FIG. 3B), which extended the first and second lagging primers until synchronized with the leading primer. Because flow 101 did not include a T nucleotide, it did not extend further. The simulated rephasing flow cycle continued with flow 102, which had a mixture of G, C, and T non-terminating nucleotides (FIG. 3C), flow 103, which had a mixture of G, T, and A non-terminating nucleotides (FIG. 3D), and flow 104, which had a mixture of T, A, and C non-terminating nucleotides (FIG. 3E).

The simulated re-phasing flow cycle was tested using additional sequences as seen in FIG. 4A-4E and FIG. 5A-5E. Other successful simulations were conducted using a re-phasing flow cycle and different template sequences.

Example 2

The effect of re-phasing using re-phasing flow steps having a mixture of two or three different nucleotide bases was studied using a simulated sequencing methodology. Approximately 10,000 synthetic (i.e., simulated) sequencing reads, each 600 bp in length, were generated by random start-site selection from a human genome. In a control group, simulated flowgrams were generated by in silico sequencing of the synthetic sequencing reads using 105 rounds of a T-G-C-A flow cycle (420 total flows). The probability of lag phasing (i.e., a fraction of nucleotides that did not incorporate into an extending primer strand when the template indicated the nucleotide should have been incorporated per nucleotide correctly incorporated) was set to 0.2%, and the probability of lead phasing (i.e., a fraction of sequencing reads wherein an extra nucleotide was incorporated into the extending primer after each flow) was set to 0.5%. The average read length for the control group was 322 bp 18 bp.

In a series of test groups, simulated flowgrams were generated by in silico sequencing of the synthetic sequencing reads using 105 rounds of a T-G-C-A flow cycle (420 total flows), except for one of the following conditions: (1) after every 24th flow, a re-phasing flow containing a mixture of C and G was inserted (FIG. 6A); (2) after every 48th flow, a re-phasing flow containing a mixture of C and G was inserted (FIG. 6B); (3) after every 96th flow, a re-phasing flow containing a mixture of C and G was inserted (FIG. 6C); (4) after every 192nd flow, a re-phasing flow containing a mixture of C and G was inserted (FIG. 6D); (5) after every 48th flow, a re-phasing flow containing a mixture of C, G, and T was inserted, followed by a single A flow (to avoid redundant flow) before reverting back to the T-G-C-A cycle according to the control protocol (FIG. 6E); (6) after every 96th flow, a re-phasing flow containing a mixture of C, G, and T was inserted, followed by a single A flow (to avoid redundant flow) before reverting back to the T-G-C-A cycle according to the control protocol (FIG. 6F); (7) after every 96th flow, a re-phasing flow containing a mixture of C, G, and T was inserted, followed by a re-phasing flow containing a mixture of A, C, and G (FIG. 6G); (8) after every 192nd flow, a re-phasing flow containing a mixture of C, G, and T was inserted, followed by a re-phasing flow containing a mixture of A, C, and G (FIG. 6I); (9) after every 96th flow, a re-phasing flow containing a mixture of C, G, and T was inserted, followed by a re-phasing flow containing a mixture of A, C, and T, followed by a re-phasing flow containing a mixture of A, G, and T followed by a re-phasing flow containing a mixture of A, C, and G (FIG. 6I); or (10) after every 192nd flow, a re-phasing flow containing a mixture of C, G, and T was inserted, followed by a re-phasing flow containing a mixture of A, C, and T, followed by a re-phasing flow containing a mixture of A, G, and T followed by a re-phasing flow containing a mixture of A, C, and G (FIG. 6J).

The use of any of the tested re-phasing flows resulted in a substantial decrease in total phasing error (i.e., the sum of the fraction of strands having a lag phasing error and the fraction of strands having a lead phasing error, relative to a nominally sequenced strand where no lag or lead error was introduced) after the full round of in silico sequencing, compared to the control, with minimal loss of sequencing data. FIGS. 6A-6J show the distribution of the sum of total phasing error for the control protocol and each respective re-phasing flow protocol. Using a re-phasing flow containing a mixture of C and G after every 24th flow reduced the mean total accumulated phasing error to 31.2±9.6% (compared to 51.5±1.3% control) (FIG. 6A), after every 48th flow reduced the mean total accumulated phasing error to 36.9±9.7% (FIG. 6B), after every 96th flow reduced the mean total accumulated phasing error to 40.2±10.1% (FIG. 6C), and after every 192nd flow reduced the mean total accumulated phasing error to 42.8±10.4% (FIG. 6D), while only generating a ~1 bp mean primer extension (i.e., sequencing gap) per re-phasing flow. Using a re-phasing flow containing a mixture of C, G, and T after every 48th flow reduced the mean total accumulated phasing error to 28.5±10.6% (FIG. 6E), and after every 96th flow reduced the mean total accumulated phasing error to 31.1±12.2% (FIG. 6F), while only generating a ~5 bp mean primer extension per re-phasing flow. Using a first re-phasing flow containing a mixture of C, G, and T and a second re-phasing flow containing a mixture of A, C, and G after every 96th flow reduced the mean total accumulated phasing error to 25.3±10.6% (FIG. 6G), and after every 192nd flow reduced the mean total accumulated phasing error to 26.6±12.6% (FIG. 6H), while only generating a ~9 bp mean primer extension per re-phasing doublet flow. Using a first re-phasing flow containing a mixture of C, G, and T, a second re-phasing flow containing a mixture of A, C, and T, a third re-phasing flow containing a mixture of A, G, and T, and a fourth re-phrasing flow containing a mixture of A, C, and G after every 96th flow reduced the mean total accumulated phasing error to 20.6±9.4% (FIG. 6I), and after every 192nd flow reduced the mean total accumulated phasing error to 20.9±11.2% (FIG. 6J), while only generating ~18 bp mean primer extension per re-phasing quadruplet flow.

Example 3

The effect of re-phasing using re-phasing flow steps having a mixture of two or three different nucleotide bases was studied using a simulated sequencing methodology. Approximately 10,000 synthetic (i.e., simulated) identical polynucleotides 500 bp in length were generated by random start-site selection from a human genome (hg38). The probability of lag phasing (i.e., a fraction of nucleotides that did not incorporate into an extending primer strand when the template indicated the nucleotide should have been incorporated per nucleotide correctly incorporated) was set to 0.2%, and the probability of lead phasing (i.e., a fraction of sequencing reads wherein an extra nucleotide was incorporated into the extending primer after each flow) was set to 0.2%.

Simulated sequencing was performed by extending a sequencing primer for 34 sequencing cycles (each sequencing cycle containing 4 sequencing flows in the order of T-G-C-A), before entering a re-phasing cycle ((not-T)-(not-G)-(not-C)), which was followed by another 34 sequencing cycles (each sequencing cycle containing 4 sequencing flows in the order of T-G-C-A). After each flow, the location of the end of the primer was recorded. The phasing rate per flow was measured as the proportion of sequencing primers (out of the where the end of the primer was located at the expected position if there were no lagging or leading events. Re-phasing efficiency was measured by comparing the average in-phase rate before and after the re-phasing cycle. Secondary re-phasing efficiency was also measured as the rate at which the re-phasing efficiency exceeded 0.15. The greatest improvement was observed when three re-phrasing flows were used according to a re-phasing cycle of (not-T)-(not-G)-(not-C), which an average in-phase rate after the re-phasing cycle of and a fraction of 0.66 of inserts gaining 0.15 increase of re-phasing benefit.

The expected re-phasing efficiency may be simulated for any given sequence, and a given re-phasing cycle may be more or less efficient depending on the sequence of the polynucleotide. If a sequence of a polynucleotide is known (that is, known a priori), a re-phasing cycle can be selected to obtain a desired efficiency of re-phasing.

FIG. 7A shows the in-phase flow rate (before and after the re-phasing cycle) and secondary re-phasing efficiency of an exemplary polynucleotide when 1, 2, 3, 4, 5, 6, 8, 10, 15, 20, or 30 re-phasing flows were used according to the (not-T)-(not-G)-(not-C) cycle.

FIG. 7B shows an example simulation of the rate of in-phase sequencing primers as a function of polynucleotide position. As the sequencing progresses, the proportion of in-phase primers decreases until the re-phasing cycle is initiated. FIG. 7C shows the number of sequencing primers reaching base position 76 (before the re-phasing cycle) as a function of flow number, and FIG. 7D shows the number of sequencing primers reaching base 84 (after the re-phasing cycle) a function of flow number. As can be seen from these figures, the re-phasing cycle provides a substantial increase in the number of in-phase sequencing primers.

Example 4

A polynucleotide (TF3) was amplified on a bead and sequencing data was collected for 34 sequencing cycles, each sequencing cycle containing four sequencing flows according to an order of T-G-C-A. The sequencing cycles were followed by a re-phasing cycle containing three triplet flows according to (not-T)-(not-G)-(not-C). The re-phasing cycle was then followed by additional collection of sequencing data for 34 sequencing cycles, each sequencing cycle containing four sequencing flows according to an order of T-G-C-A.

FIG. 8A shows sequencing data for sequencing flows containing C nucleotides. Data for a control polynucleotide where no re-phasing cycle was used is overlaid for comparison. The Y-axis shows signal strength, and the X-axis indicates each flow used to extend the sequencing primer (a "+" indicates an expected signal for a C nucleotide, a "−" indicates no expected signal for a C nucleotide, and an integer indicates a homopolymer with consecutive C nucleotides incorporated). The sequencing signal for both runs was similar prior to re-phasing. The sequencing data collected after re-phrasing shows an increase in the difference between the presence and absence of a C nucleotide signal, which is particularly pronounced over homopolymer, compared to the control signal. Similar sequencing data for sequencing flows containing only G nucleotides (FIG. 8B), T nucleotides (FIG. 8C), and A nucleotides (FIG. 8D) was also collected. A simulation was used to visualize sequencing primers within a sequencing cluster using numerous copies of the polynucleotide within the cluster, assuming a set over-incorporation and under-incorporation rate.

Figure 10B:
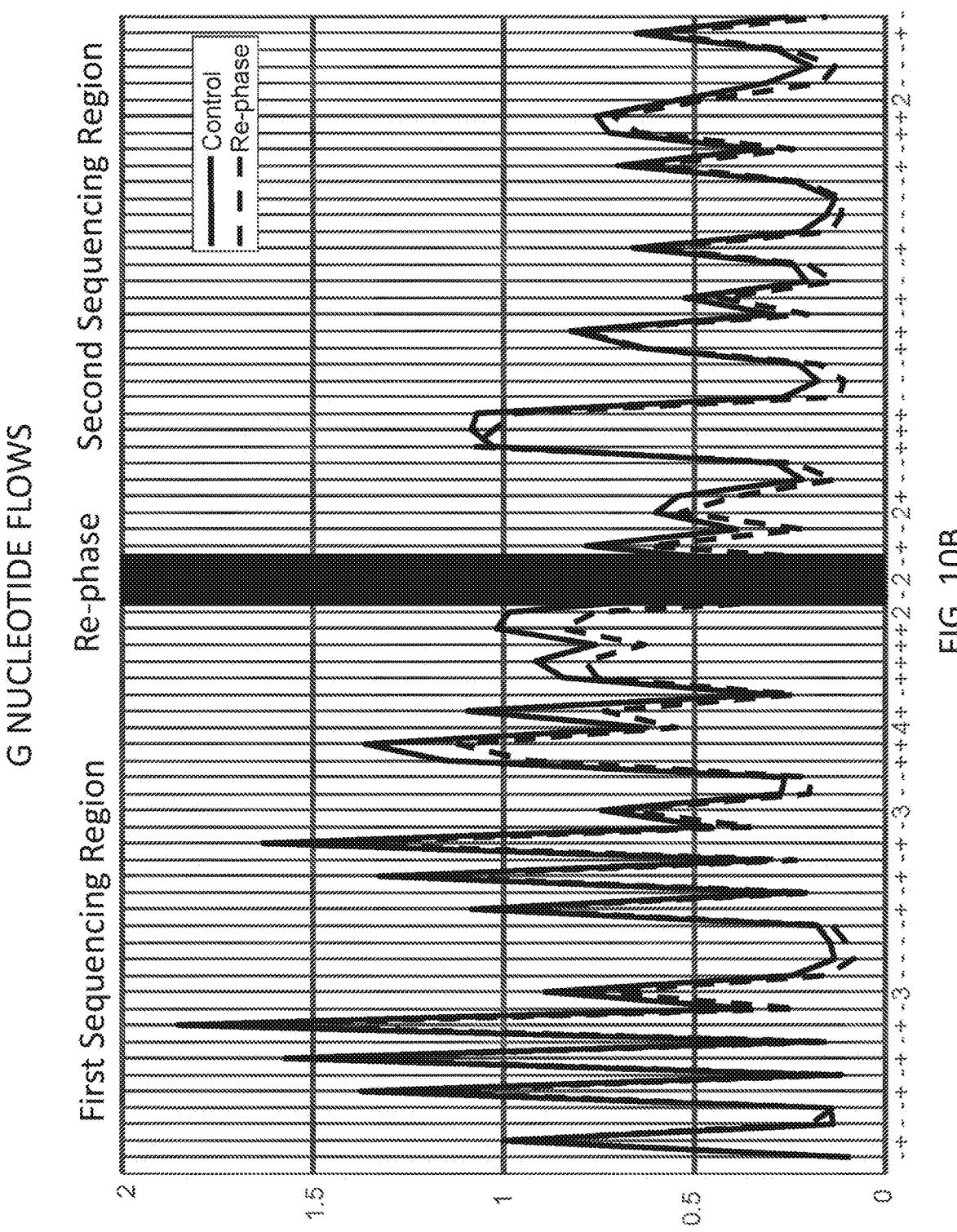
Figure 10C:
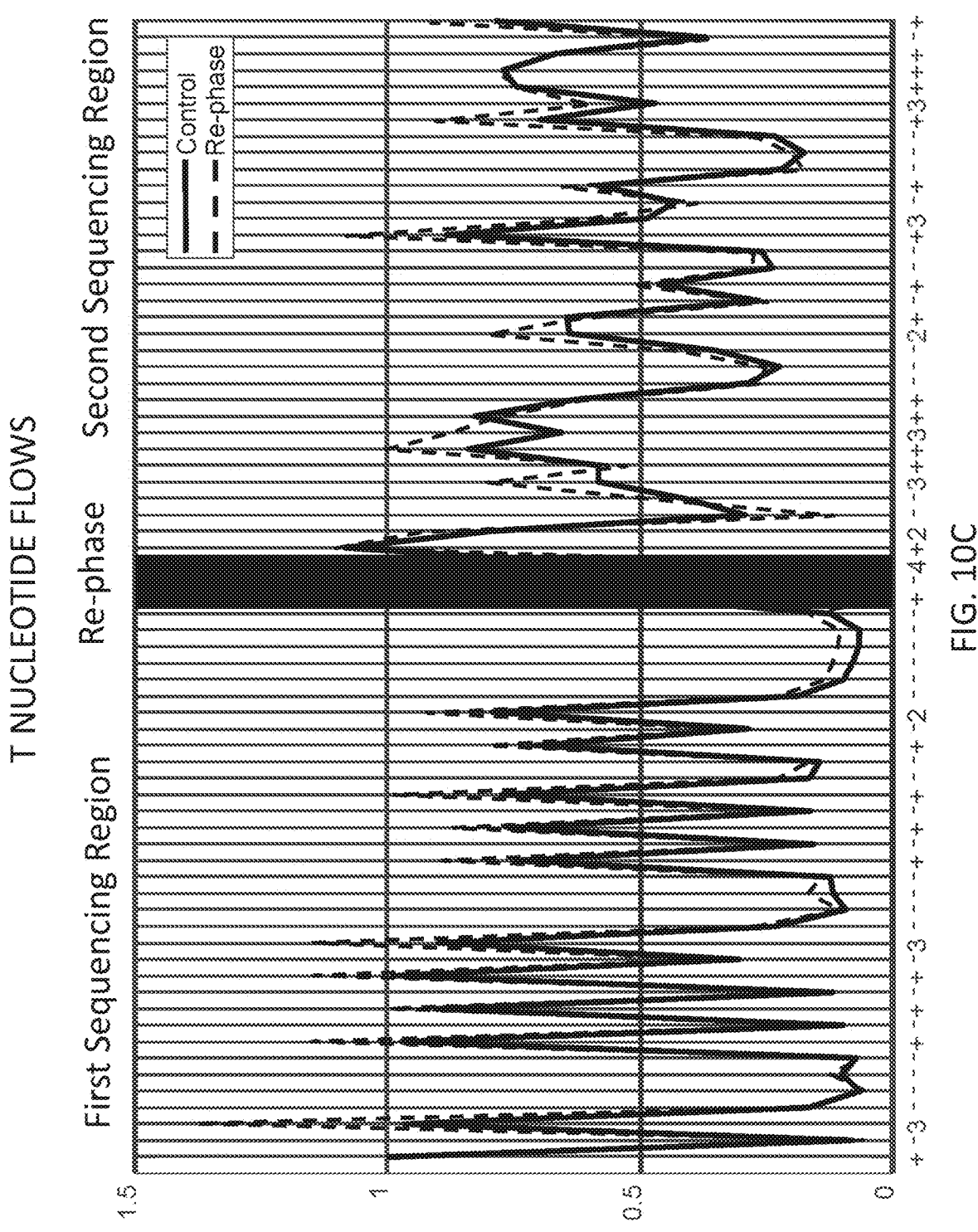
Figure 10D:
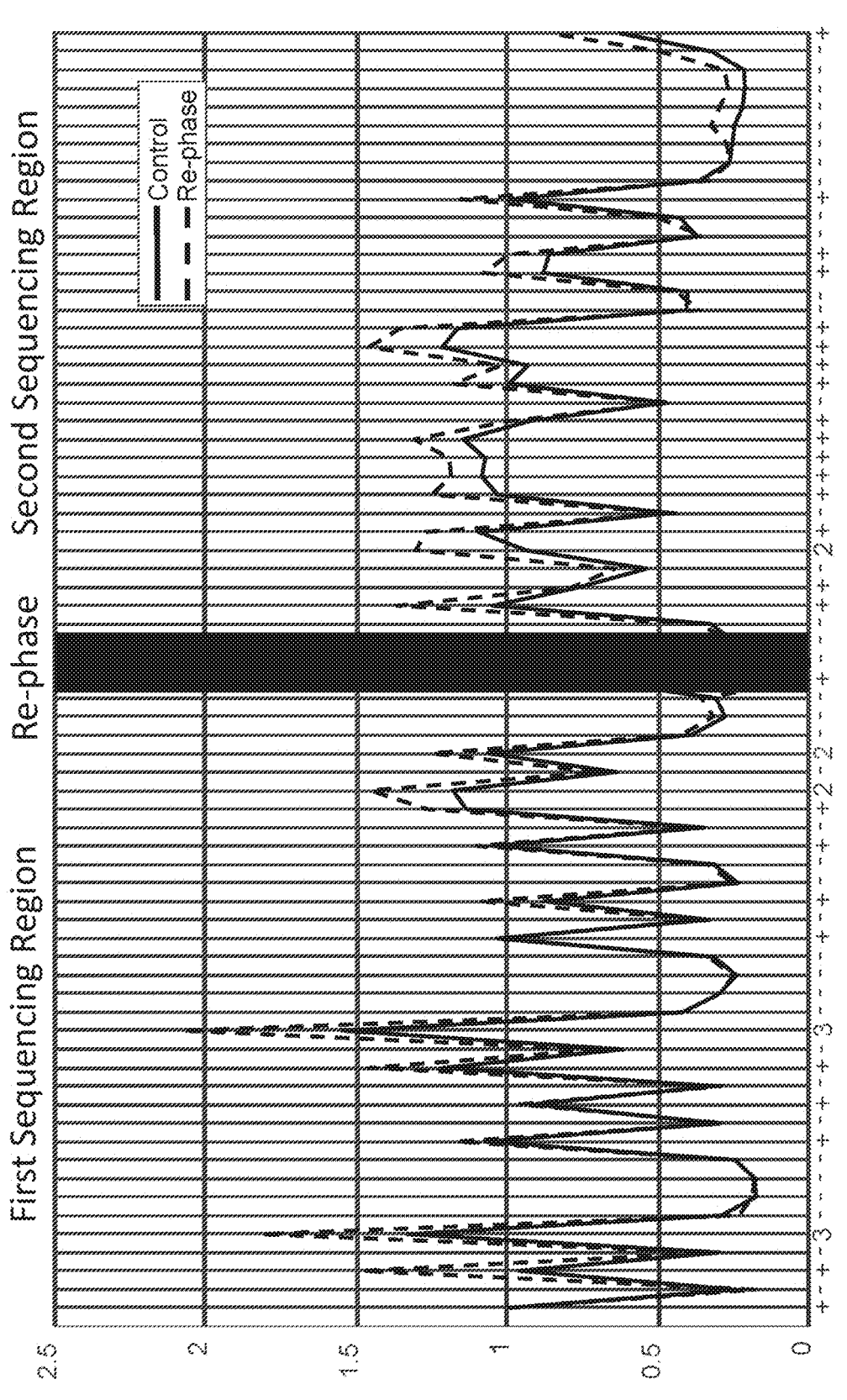

Sequencing data for an additional polynucleotide (TF6) was obtained using a similar process, as shown in FIG. 10A (C nucleotides), FIG. 10B, (G nucleotides), FIG. 10C (T nucleotides), and FIG. 10D (A nucleotides). The re-phasing benefit is less pronounced for the TF6 polynucleotide, although is still apparent. This demonstrates that the re-phasing benefit can be applied to different sequences. Further, the phasing benefit can be simulated for any particular sequence.

A comparison between a simulated re-phrasing benefit provided to the TF3 polynucleotide and the TF6 polynucleotide is shown in FIG. 9. The re-phasing cycles improve the fraction of in-phase sequencing primers, but the TF3 sequence received greater benefit compared to the TF6 sequence.

---

What is claimed is:

1. A method of synchronizing sequencing in a colony, comprising:

(a) providing a sequencing colony comprising a plurality of copies of nucleic acid molecules each having sequence identity to a polynucleotide derived from a sample, wherein each nucleic acid molecule of the plurality of copies comprises a first region, a second region, and a third region;

(b) hybridizing a plurality of primers to the plurality of copies;

(c) extending the plurality of primers through the first region by, in each flow step of a plurality of first flow cycles having a first predetermined number of flow steps, providing a first plurality of nucleotides of a single base type, wherein at least a portion of the first plurality of nucleotides is labeled;

(d) extending, after the first predetermined number of flow steps, the plurality of primers through the second region by, in each flow step of a plurality of second flow cycles, providing a second plurality of nucleotides comprising at least two base types; and (e) extending the plurality of primers through the third region by, in each flow step of a plurality of third flow cycles, providing a third plurality of nucleotides of a single base type, wherein at least a portion of the third plurality of nucleotides is labeled.

2. The method of claim 1, wherein the first predetermined number of flow steps is between about 40 and about 500.

3. The method of claim 1, wherein the first predetermined number of flow steps is associated with a predetermined sequencing signal threshold.

4. The method of claim 1, wherein the first predetermined number of sequencing flow steps is associated with an expected length of the first region.

5. The method of claim 1, wherein the plurality of third flow cycles has a second predetermined number of flow steps, the method further comprising:

(f) extending, after the second predetermined number of flow steps, the plurality of primers through a fourth region of the plurality of copies by, in each flow step of a plurality of fourth flow cycles, providing a fourth plurality of nucleotides comprising at least two base types; and (g) extending the plurality of primers through a fifth region of the plurality of copies by, in each flow step of a plurality of fifth flow cycles, providing a fifth plurality of nucleotides of a single base type, wherein at least a portion of the fifth plurality of nucleotides is labeled.

6. The method of claim 5, wherein the first predetermined number of flow steps and the second predetermined number of flow steps are the same.

7. The method of claim 1, wherein a mixture of three different base types is used in at least one flow step of the plurality of second flow cycles.

8. The method of claim 1, wherein one or more flow steps of the plurality of second flow cycles comprise 2 to 12 re-phasing flow steps.

9. The method of claim 1, wherein one or more flow steps of the plurality of second flow cycles comprise one or more of the following in any order:

(i) a flow step comprising a mixture comprising A, C, and G nucleotides and omitting T nucleotides;

(ii) a flow step comprising a mixture comprising T, C, and G nucleotides and omitting A nucleotides;

(ii) a flow step comprising a mixture comprising T, A, and G nucleotides and omitting C nucleotides; and (iv) a flow step comprising a mixture comprising T, A, and C nucleotides and omitting G nucleotides.

10. The method of claim 1, further comprising sequencing the first region by detecting the presence or absence of an incorporated labeled nucleotide while extending the primers through the first region.

11. The method of claim 1, wherein at least a portion of nucleotides provided in the plurality of second flow cycles are unlabeled.

12. The method of claim 1, wherein a first flow order of the plurality of first flow cycles and a third flow order of the plurality of third flow cycles are the same.

13. The method of claim 1, wherein a first flow order of the plurality of first flow cycles and a third flow order of the plurality of third flow cycles are different.

14. The method of claim 1, wherein the plurality of primers is extended through the first region by repeating a first flow order a plurality of times in the plurality of first flow cycles.

15. The method of claim 14, wherein the first flow order is repeated 2 times to about 50 times.

16. The method of claim 1, wherein a distance between a start of the first region and an end of a final region of the plurality of copies for which sequencing data is generated is at least 300 bases in length.

17. The method of claim 1, wherein the sequencing colony is produced by rolling circle amplification of a template nucleic acid molecule, and the sequencing colony comprises multiple copies of the template nucleic acid molecule covalently attached in a linear sequence.

18. The method of claim 1, wherein nucleotides provided in the extending (c) comprise a mixture of labeled and unlabeled nucleotides.

19. The method of claim 1, wherein nucleotides provided in the extending (d) are non-terminated.

20. The method of claim 10, wherein flow steps of the plurality of first flow cycles further comprise (i) detection of a signal from a label of an incorporated labeled nucleotide and (ii) cleavage of the label.

*     *     *     *     *